United States Patent [19]

Tamura et al.

[11] Patent Number: 5,656,645
[45] Date of Patent: Aug. 12, 1997

[54] AROMATIC HETEROCYCLIC DERIVATIVES AS ENZYME INHIBITORS

[75] Inventors: Susan Yoshiko Tamura; Joseph Edward Semple; William Charles Ripka, all of San Diego; Robert John Ardecky, Encinitas; Yu Ge, San Diego; Stephen H. Carpenter, San Diego; Terence K. Brunck, San Diego, all of Calif.

[73] Assignee: Corvas International, Inc., San Diego, Calif.

[21] Appl. No.: 484,506

[22] Filed: Jun. 7, 1995

Related U.S. Application Data

[63] Continuation-in-part of Ser. No. 356,833, Dec. 13, 1994.
[51] Int. Cl.[6] .................. A61K 31/44; A61K 31/505; C07D 213/64; C07D 233/32; C07D 233/40
[52] U.S. Cl. .................. 514/349; 514/274; 544/309; 544/319; 546/292
[58] Field of Search .................. 546/292; 544/319, 544/309; 514/274, 349

[56] References Cited

U.S. PATENT DOCUMENTS

| 4,399,065 | 8/1983 | Bajusz | 530/331 |
| 5,371,072 | 12/1994 | Webb et al. | 514/18 |
| 5,492,895 | 2/1996 | Vlasuk et al. | 514/18 |

FOREIGN PATENT DOCUMENTS 0509769 10/1992 European Pat. Off. .
0528633 2/1993 European Pat. Off. .

OTHER PUBLICATIONS

Coughlin, P. et al Proc. Natl. Acad. Sci. USA, 1993, 90 (20), 9417–21, see abstract.
Aldrich Chemical Company, Inc. Catalog (1995) p. 283.
Bachem California Catalog (1993–1994) p. 121.
Bachem Bioscience Catalog (1995) p. 721.
Williams et al., "1-(((7,7-Dimethyl-2(S)-2(S)-amino-4-(methylsulfonyl)butyramido)bicyclo[2.2.1]-heptan-1(S)-yl)methyl)sulfonyl)-4-(2-methylphenyl)piperazine (L-368,889): An Orally Bioavailable, Non-Peptide Oxytocin Antagonist with Potential Utility for Managing Preterm Labor," *J. Med. Chem.* 37:565–571 (1994).
Damewood et al., "Nonpeptidic Inhibitors of Human Leukoycyte Elastase. 2. Design, Synthesis, and in vitro Activity of a Series of 3-Amino-6-arylopyridine-2-one Trifluoromethyl Ketones," *J. Med. Chem.* 37:3303–3312 (1994).
Skiles et al., "Elastase Inhibitors Containing Conbformationally Restricted Lactams as $P_3$–$P_2$ Dipeptide Replacements," *Bioorg. Med. Chem. Lett.* 3(4):773–779 (1993).

*Primary Examiner*—C. Warren Ivy
*Assistant Examiner*—Garth M. Dahlen
*Attorney, Agent, or Firm*—Lyon & Lyon

[57] ABSTRACT

The present invention discloses heterocyclic aromatic peptide aldehydes which have an oxopyrimidine or oxopyridine group and an argininal tail which are potent and specific inhibitors of thrombin, their pharmaceutically acceptable salts, pharmaceutically acceptable compositions thereof, and methods of using them as therapeutic agents for disease states in mammals characterized by abnormal thrombosis.

31 Claims, 12 Drawing Sheets i) $K_2CO_3$, DMF, $BrCH_2CO_2$-t-Bu; ii) LiOH, THF; iii) $Et_3N$, DPPA, dioxane, Δ; BnOH, Δ; iv) $H_2$, Pd/C; v) $R_1SO_2Cl$, collidine; vi) TFA i) NaH, DMF, BrCH$_2$CO$_2$t-Bu; ii) LiOH, THF; iii) Et$_3$N, DPPA, dioxane, Δ; BnOH, Δ;
iv) H$_2$, Pd/C; v) R$_1$SO$_2$Cl, NMM; vi) TFA i) $K_2CO_3$, $R_7X$, DMSO; ii) NaH, $BrCH_2CO_2$t-Bu; iii) $H_2$, 10% Pd/C; iv) $R_1SO_2Cl$, NMM;
v) trifluoroacetic acid i) 2 equiv. LDA; R₈X; 50% H₂SO4; iii) Et₃N, DPPA, dioxane, Δ; BnOH, Δ; iv) NaH, DMF, BrCH₂CO₂t-Bu,
v) H₂, Pd/C; vi) R₁SO₂Cl, collidine; vii) TFA i) LiN(TMS)₂; TMSCl; LiN(TMS)₂; benzaldehyde; ii) LiN(TMS)₂, ethyl bromoacetate;
iii) Ac₂O, 10% Pd/C, H₂, iv) LiOH

AROMATIC HETEROCYCLIC DERIVATIVES AS ENZYME INHIBITORS

CROSS REFERENCE TO RELATED APPLICATION

This application is a continuation-in-part of U.S. Ser. No. 08/356,833, filed Dec. 13, 1994 pending, the disclosure of which is incorporated herein by reference.

TECHNICAL FIELDS

In one aspect, the present invention relates to compounds which are potent and specific inhibitors of thrombin. In another aspect, the present invention relates to novel peptide aldehydes, their pharmaceutically acceptable salts, and pharmaceutically acceptable compositions thereof which are useful as potent and specific inhibitors of blood coagulation in vitro and in vivo in mammals. In yet another aspect, the invention relates to methods of using these inhibitors as therapeutic agents for disease states in mammals characterized by abnormal thrombosis.

BACKGROUND

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix which is required for the stabilization of the primary hemostatic plug. The interaction and propagation of the activation reactions occurs through the extrinsic and intrinsic pathways of coagulation.

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic Mechanisms", Disorders of Hemostasis, pp. 27–29, Grune & Stratton, inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, Id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et al., "Surface-Dependent Reactions of the Vitamin K-Dependent Enzyme Complexes", Blood, 76: 1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", J. Clin. invest., 71: 1383–1391(1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., Arch. Biochem. Biophys., 105: 58 (1964). Beyond its direct role in the formation and stabilization of fibrin rich clots, the enzyme has been reported to have profound bioregulatory effects on a number of cellular components within the vasculature and blood. Shuman, M. A., Ann. NY Acad. Sci., 405: 349 (1986).

It is believed that thrombin is the most potent agonist of platelet activation, and it has been demonstrated to be the primary pathophysiologic-mediator of platelet-dependent arterial thrombus formation. Edit, J. F. et al., J. Clin. Invest., 84: 18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., Platelets in Biology and Pathology, pp 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., Blood, 77: 2641 (1991). This positive feedback process results in the local generation of large concentrations of thrombin within the vicinity of the thrombus which supports further thrombus growth and extension. Mann, K. G. et al., Blood, 76: 1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., Biochemistry, 27: 769 (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., Science, 235: 1348 (1987). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., Proc. Natl. Acad. Sci. U.S.A., 72: 131 (1975). The direct interaction of thrombin with vascular smooth muscle also results in vasoconstriction. Walz, D. A. et al., Proc. Soc. Expl. Biol. Med., 180: 518 (1985). Thrombin acts as a direct secretagogue inducing the release of a number of bioactive substances from vascular endothelial cells including tissue plasminogen activator. Levin, E. G. et al., Thromb. Haemost., 56: 115 (1986). In addition to these direct effects on vascular cells, the enzyme can indirectly elaborate potent mitogenic activity on vascular smooth muscle cells by the release of several potent growth factors (e.g., platelet-derived growth factor and epidermal growth factor) from platelet a-granules following thrombin-induced activation. Ross, R., N. Engl. J. Med., 314: 408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., Thrombosis in Cardiovascular Disorder, p. 327, W. B. Saunders Co. (Fuster, V. and Verstraete, M. edit. 1991); Califf, R. M. and Wilierson, J. T., Id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., J. Am. Coll. Cardiol., 67: 3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., J. Am. Coll. Cardiol., 17: 2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aα chain of fibrinogen, which is the primary physiological substrate for thrombin, is reported to contain a glycine residue in this position while the cleavage site on the Bβ chain contains a serine, as shown below:

P4   P3   P2   P1   P1'
Gly—Gly—Val—Arg/Gly    Fibrinogen Aα Chain
Phe—Ser—Ala—Arg/Gly    Fibrinogen Bβ Chain Peptidyl derivatives having an uncharged residue in the P3 position are said to bind to the active site of thrombin and thereby inhibit the conversion of fibrinogen to fibrin and inhibit cellular activation. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., Symposia Biologica Hungarica, 25: 277 (1984), Bajusz, S. et al, J. Med. Chem., 33: 1729 (1990) and Bajusz, S. et al., Int. J. Peptide Protein Res. 12: 217 (1970); Kettner, C. and Shaw, E., Methods Enzymol., 80: 826 (1987), Kettner, C. et al., EP 293,881 (published Dec. 7, 1988), Kettner, C., et al., J. Biol. Chem., 265: 18209 (1990). These molecules have been reported to be potent anticoagulants in the prevention of platelet-rich arterial thrombosis. Kelly, A. B. et al., Thromb. Haemostas., 65: 736 at abstract 257 (1991). Other peptidyl aldehydes have been proposed or reported as inhibitors of thrombin. Bey, P. et al., EP 363,284 (published Apr. 11, 1990) and Balasubramanian, N. et al., EP 526,877 (published Feb. 10, 1993).

Peptidyl compounds which are said to be active site inhibitors of thrombin but which differ in structure from those containing a uncharged amino acid in the P3 recognition subsite have been reported.

The compound, Argatroban (also called 2R,4R-4-methyl-1-[N-2-(3-methyl-1,2,3,4-tetrahydro-8-quinolinesulfonyl)-L-argininal]-2-piperdinecarboxylic acid), is also reported to bind directly to the active site of thrombin and has been thought to be the most potent and selective compound in the class of non-peptidyl inhibitors of this enzyme. Okamoto, S. et al., Biochem. Biophys. Res. Commun., 101: 440 (1981). Argatroban has been reported to be a potent antithrombotic agent in several experimental models of acute arterial thrombosis. Jang, I. K. et al., in both Circulation, 81: 219 (1990) and Circ. Res., 67: 1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., Thromb. Haemostas., 66: 141 (1991). Hirudin is reported to be a 65 amino acid polypeptide originally isolated from leech salivary gland extracts. It is said to be one of the most potent inhibitors of thrombin known. Marki, W. E. and Wallis, R. B., Thromb. Haemostas., 64: 344 (1990). It has been reported to inhibit thrombinbybinding to both its anion-binding exo-site and to its catalytic active site which are distinct and physically distant from each other. Rydel, T. J. et al., Science, 249:277 (1990). Hirudin has been reported to be a potent antithrombotic agent in vivo. Markwardt, F. et al., Pharmazie, 43: 202 (1988); Kelly, A. B. et al., Blood, 77: 1 (1991). In addition to its antithrombotic effects, hirudin has been reported to also effectively inhibit smooth muscle proliferation and the associated restenosis following mechanical damage to a atherosclerotic rabbit femoral artery. Sarembock, I. J. et al., Circulation, 84: 232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., J. Biol. Chem., 264: 8692 (1989); Naski, M. C. et al., J. Biol. Chem., 265: 13484 (1990). Based on x-ray crystallographic analysis, it has been reported that the region of hirudin represented byhirugen binds directly to the exo site of thrombin. Skrzypczak-Jankun, E. et al., Thromb. Haemostas., 65: 830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, L. W. et al., J. Biol. Chem, 266:16977 (1991). Hirugen also is reported to block thrombin-mediated platelet aggregation. Jakubowski, J. A. and Maraganore, J. M., Blood, 75: 399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., Biochemistry, 29: 7095 (1990). The hirulogs have been reported to be an effective antithrombotic agents in preventing both fibrin-rich and platelet-rich thrombosis. Maraganone, J. M. et al., Thromb. Haemostas., 65: 651 at abstract 17 (1991).

Certain benzamidines have been reported to inhibit thrombin though non-selectively. 4-amidinophenylpyruvic acid (APPA) has been reported to be a thrombin inhibitor with low toxicity and favorable pharmacokinetics. However, this compound was reported to be non-selective, inhibiting trypsin, plasmin and kallikrein. Markwardt et al., Thromb. Res., 1:243–52 (1972). Other benzamidine-derived structures which have been reported to inhibit thrombin include the cylic amides of $N^\alpha$-substituted 4-amidinophenylalanine and 2-amino-5-(4-amidinophenyl)-1-valeric acid. The inhibitory constant displayed by these compounds was reported to be in the micromolar range. Markwardt et al., Thromb. Res., 17:425–31 (1980). Moreover, derivatives of 4-amidinophenylalanine whose a-amino group is linked to the arylsulfonyl residue via an w-aminoalkylcarboxylic acid as spacer have also been assessed for their inhibitory effect. Among these $N^\alpha$-(2-naphthylsulphonylglycyl)-4-amidinophenylalanine piperidide (a-NAPAP) has been reported to possess an affinity for thrombin ($K_i=6\times10^{-9}M$). Banner et al., J. Biol. Chem., 266:20085 (1991) and Sturzebecher et al., Thromb. Res., 29:635–42 (1983).

Certain bis-benzamidines have been reported to inhibit thrombin. The antithrombin activity of bis-benzamidines was reported to increase with the length and bulkiness of the central chain. However, these compounds were reported to be generally toxic in the micromolar range where they are also inhibitory. Geratz et al., Thromb. Diath. Haemorrh., 29:154–67 (1973); Geratz et al., J. Med. Chem., 16:970–5 (1973); Geratz et al., J. Med. Chem., 19:634–9 (1976); Walsmann et al., Acta Biol. Med. Germ., 35:K1–8 (1976); and Hauptmann et al., Acta Biol. Med. Germ., 35:635–44 (1976).

Certain amidino-bearing aromatic ring structures such a beta-naphthamidines have been reported to possess modest antithrombin and anticoagulant activity. This class of compounds include the non-selective 6-amidino-2-naphthyl-4-guanidinobenzoate dimethanesulfonate (FUT 175). Fuji et al., Biochim. Biophys. Acta, 661:342–5 (1981); and Hitomi et al., Haemostasis, 15:164–8 (1985).

Certain phenylguanidines have been reported to inhibit thrombin. Derivatives of 4-guanidinophenylalanine with inhibitory constants in the micromolar range have been reported to inhibit thrombin. This class includes the $N^\alpha$-tosylated and dansylated 4-guanidino phenylalanine piperidides. Claeson et al., Thromb. Haemostas., 50:53 (1983). Another compound, [ethyl p-(6-guanidinohexanoyloxy)benzoate]methane sulfonate (FOY) was reported to be a non-selective competitive inhibitor of thrombin. Ohno et al., Thromb. Res., 19:579–588 (1980).

SUMMARY OF THE INVENTION

The present invention is directed to novel peptide aldehyde compounds having arginine or arginine mimics at $P_1$ and pyridone, pyrimidone, or uracil groups as part of the peptide backbone. These compounds are potent inhibitors of thrombin in vivo and in vitro.

Thus, in one aspect, the present invention is directed to compounds of the formula:

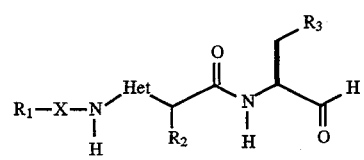

wherein (a) X is selected from the group consisting of —S(O)$_2$—, —N(R')—S(O)$_2$—, —(C=O)—, —OC(=O)—, —NH—C(=O)—, —P(O)(R")— and a direct link, wherein R' is hydrogen, alkyl of 1 to about 4 carbon atoms, aryl of about 6 to about 14 carbon atoms or aralkyl of about 6 to about 16 carbon atoms, and R" is NR', OR', R', or SR', with the proviso that R" is not NH, OH, H, or SH, and;

(b) $R_1$ is selected from the group consisting of:
  (1) alkyl of 1 to about 12 carbon atoms,
  (2) alkyl of 1 to about 3 carbon atoms substituted with cyclic alkyl of about 5 to about 8 carbon atoms, which optionally is substituted in the ring carbons with hydroxyl, amino, guanidino, amidino, or alkoxyl or alkyl each of 1 to about 3 carbons,
  (3) cyclic alkyl of 3 to about 15 carbon atoms, which optionally is substituted in the ring carbons with hydroxyl, amino, guanidino, amidino, or alkoxyl or alkyl each of 1 to about 3 carbons,
  (4) heterocycloalkyl of 4 to about 10 ring atoms with the ring atoms selected from carbon and heteroatoms, wherein the heteroatoms are selected from the group consisting of oxygen, nitrogen, and $S(O)_i$, where i is 0, 1 or 2, optionally substituted in the ring carbons with hydroxyl, alkoxyl or alkyl each of 1 to about 3 carbons, amino, guanidino, or amidino,
  (5) heterocyclo of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, optionally substituted in the ring carbons with hydroxyl, alkoxyl or alkyl each of 1 to about 3 carbons, amino, guanidino, or amidino,
  (6) alkenyl of about 3 to about 6 carbon atoms which is optionally substituted with cyclic alkyl of about 5 to about 8 carbon atoms, which optionally is substituted in the ring carbons with hydroxyl, amino, guanidino, amidino, or alkoxyl or alkyl of 1 to about 3 carbons,
  (7) aryl of about 6 to about 14 carbon atoms which is optionally mono-, di- or tri-substituted with $Y_1$, $Y_2$, and/or $Y_3$, respectively,
  (8) heteroaryl of 5 to 14 atoms with the ring atoms selected from carbon and heteroatoms, wherein the heteroatoms are selected from oxygen, nitrogen, and $S(O)_i$, wherein i is 0, 1 or 2, optionally mono-, di- or tri-substituted with $Y_1$, $Y_2$, and/or $Y_3$, respectively,
  (9) aralkyl of about 7 to about 15 carbon atoms which is optionally mono-, di-, or tri-substituted in the aryl ring with $Y_1$, $Y_2$, and/or $Y_3$, respectively,
  (10) heteroaralkyl of 6 to 11 atoms with the ring atoms selected from carbon and heteroatoms, wherein the heteroatoms are selected from oxygen, nitrogen, and $S(O)_i$, wherein i is 0, 1 or 2, optionally mono-, di- or tri-substituted with $Y_1$, $Y_2$, and/or $Y_3$, respectively,
  (11) aralkenyl of about 8 to about 15 carbon atoms which is optionally mono-, di-, or tri-substituted in the aryl ring with $Y_1$, $Y_2$, and/or $Y_3$, respectively,
  (12) heteroaralkenyl of 7 to 12 atoms with the ring atoms selected from carbon and heteroatoms, wherein the heteroatoms are selected from oxygen, nitrogen, and $S(O)_i$, wherein i is 0, 1 or 2, optionally mono-, di- or tri-substituted with $Y_1$, $Y_2$, and/or $Y_3$, respectively,

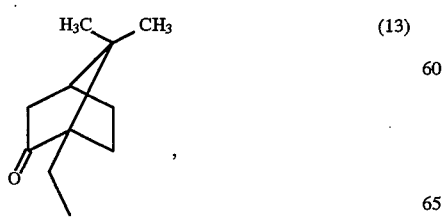
(13)

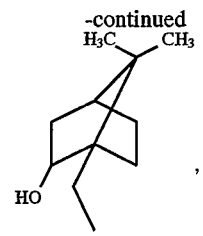
(14)

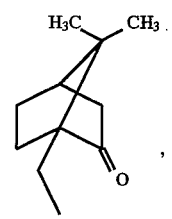
(15)

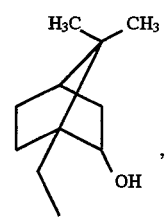
(16)

(17) perfluoroalkyl of 1 to about 12 carbon atoms,
(18) perfluoroaryl of about 6 to about 14 carbon atoms,
(19) perfluoroaralkyl of about 7 to about 15 carbon atoms,
(20) hydrogen, and
(21)

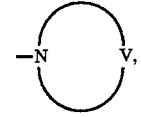

wherein

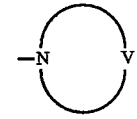

is a 5 to 7 member heterocycle of 3 to 6 ring carbon atoms, where V is —$CH_2$—, —O—, —S(=O)—, —$S(O)_2$— or —S—, wherein $Y_1$, $Y_2$, and $Y_3$ are
  (i) independently selected from the group consisting of hydrogen, halogen, cyano, tetrazolyl, amino, guanidino, amidino, methylamino, and methylguanidino, —$CF_3$, —$CF_2H$, —$CF_2CF_3$, —$CH(CF_3)_2$, —$C(OH)(CF_3)_2$, $OCF_3$, $OCF_2CF_3$, —$OC(O)NH_2$, —$OC(O)NHZ_1$, —$OC(O)NZ_1Z_2$, —$NHC(O)Z_1$, —$NHC(O)NH_2$, $NHC(O)NZ_1$, —$NHC(O)NZ_1Z_2$, —$C(O)$ OH, —$C(O)NH_2$, —$C(O)NHZ_1$, —$C(O)OZ_1$, —$P(O)_3H$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, and —$NZ_1Z_2$, wherein m is 0, 1 or 2, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or (ii) $Y_1$ and $Y_2$ are selected together to be —$OC(Z_3)$ $(Z_4)O$, wherein $Z_3$ and $Z_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms.

(c) $R_2$ is selected from the group consisting of hydrogen, alkyl of 1 to about 4 carbon atoms, and alkenyl of about 2 to about 4 carbon atoms.

(d) $R_3$ is selected from the group consisting of

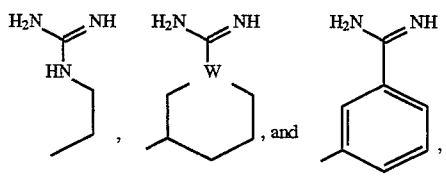

where W is nitrogen or carbon;

(e) Het is selected from the group consisting of

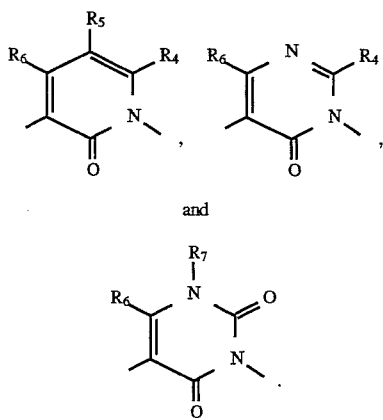

wherein (1) $R_4$ is selected from the group consisting of $R_1$, —$OR_1$, —$NHR_1$, —$S(O)_nR_1$, and halogen, wherein n is 0, 1 or 2, and $R_1$ is independently selected and as defined above, (2) $R_5$ is selected from the group consisting of $R_1$, —$OR_1$, —$NHR_1$, —$S(O)_nR_1$, and halogen, wherein n is 0, 1 or 2, and $R_1$ is independently selected and as defined above, (3) $R_6$ is selected from the group consisting of $R_1$, —$OR_1$, —$NHR_1$, —$S(O)_nR_1$, and halogen, wherein n is 0, 1 or 2, and independently selected and $R_1$ is as defined above, and (4) $R_7$ is independently selected from the $R_1$ group of substituents, as defined above.

Peptidyl arginine aldehydes have been reported to exist in equilibrium structures in aqueous solutions. Bajusz, S., et al., J. Med. Chem., 33: 1729 (1990). These structures, as shown below, include the arginine aldehyde, A, aldehyde hydrate, B, and two amino cyclol forms, C and D. The R group would represent the remainder of a given compound embodied in the present invention. The peptide aldehydes of the present invention include within their definition all the equilibrium forms.

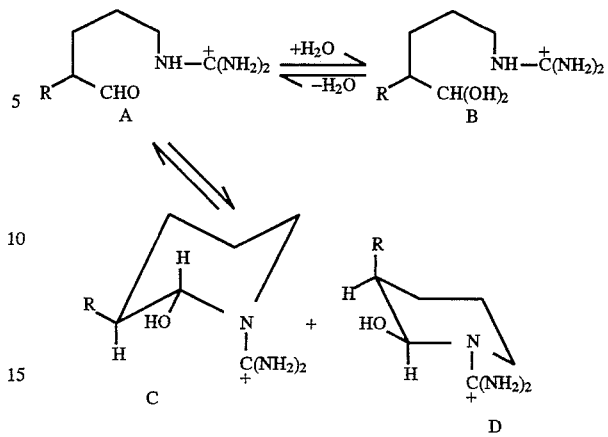

Among other factors, the present invention is based on our finding that the novel compounds of our invention are active as selective inhibitors of thrombin. In particular, we have found that certain of the preferred compounds of the present invention exhibit advantageous selectivity in that they are very potent inhibitors of thrombin but are inactive or significantly less active, (several orders of magnitude less) in inhibiting plasmin and are significantly less active in inhibiting trypsin. This selectivity for inhibition of thrombin gives these compounds a therapeutic advantage in treating or preventing thrombosis in a mammal suspected of having a condition characterized by abnormal thrombosis.

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound of the present invention or pharmaceutical composition comprising such a compound.

Definitions

In accordance with the present invention and as used herein, the following terms are defined to have following meanings, unless explicitly stated otherwise:

The term "alkenyl" refers to unsaturated aliphatic groups having at least one double bond.

The term "alkyl" refers to saturated aliphatic groups including straight-chain, branched-chain and cyclic groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aralkenyl" refers to an alkenyl group substituted with an aryl group.

The term "aralkyl" refers to an alkyl group substituted with an aryl group. Suitable aralkyl groups include benzyl, picolyl, and the like, all of which may be optionally substituted.

The term "aryl" refers to aromatic groups which have at least one ring having a conjugated pi electron system and includes carbocyclic aryl, heterocyclic aryl and biaryl groups, all of which maybe optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is H or a carbon containing substituent; or (2)

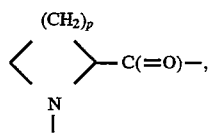

wherein p is 1, 2 or 3 representing the azetidinecarboxylic acid, proline or pipecolic acid residues, respectively.

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, nitro, and cyano. Substituted naphthyl refers to 1- or 2-naphthyl substituted by lower alkyl, lower alkoxy, or halogen.

"Cycloalkenyl" refers to a cyclic alkenyl group. Suitable cycloalkenyl groups include, for example, cyclopentenyl and cyclohexenyl.

"Cycloalkyl" refers to a cyclic alkyl group. Suitable cycloalkyl groups include, for example, cyclohexyl, cyclopropyl, cyclopentyl, and cycloheptyl.

"Cyclohexylmethyl" refers to a cyclohexyl group attached to $CH_2$.

The term "halogen" refers to fluorine, chlorine, bromine and iodine.

"Heteroaralkenyl" refers to an alkenyl group substitued with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heteroaralkyl" refers to an alkyl group substituted with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heteroaryl" refers to aryl groups having from 1 to 9 carbon atoms and the remainder of the atoms are heteroatoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, $S(O)_i$, wherein i is 0, 1 or 2, and suitable heterocyclic aryls include furanyl, thienyl, pyridyl, pyrrolyl, pyrimidyl, pyrazinyl, imidazolyl, and the like.

"Heterocyclo" refers to a reduced heterocyclic ring system comprised of carbon, nitrogen, oxygen and/or sulfur atoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heterocycloalkyl" refers to an alkyl group substituted with a heterocyclo group, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

The term "lower" referred to herein in connection with organic radicals or compounds defines such with up to and including 5, preferably up to and including 4 and advantageously one or two carbon atoms. Such groups may be straight chain or branched chain.

"Perfluoroalkyl" refers to an alkyl group which has every hydrogen replaced with fluorine.

"Perfluoroaryl" refers to an aryl group which has every hydrogen replaced with fluorine.

"Perfluoroaryl alkyl" refers an aralkyl group in which every hydrogen on the aryl moiety is replaced with fluorine.

"Pharmaceutically acceptable salt" includes salts of the compounds of the present invention derived from the combination of such compounds and an organic or inorganic acid. in practice the use of the salt form amounts to use of the base form. The compounds of the present invention are useful in both free base and salt form, with both forms being considered as being within the scope of the present invention. The term "Arg-al" refers to the residue of L-argininal which has the formula:

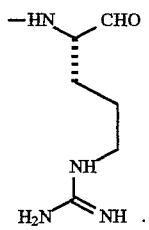

"N-alpha-t-butoxycarbonyl-N<sup>g</sup>-nitro-L-arginine" refers to the compound which has the formula:

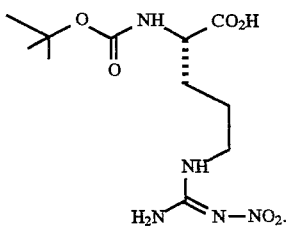

In addition, the following abbreviations stand for the following:

"Boc" refers to t-butoxycarbonyl.
"BOP" refers to benzotriazol-1-yl-oxy-tris (dimethylamino)-phosphoniumhexafluorophosphate.
"BzlSO$_2$" refers to benzylsulfonyl.
"DCC" refers to N,N'-dicyclohexylcarbodiimide.
"EDC" refers to 1-ethyl-3-(3-dimethylaminopropyl)carbodiimide hydrochloride salt.
"HBTU" refers to 2-(1H-benzotriazol-1-yl)-1,1,3,3-tetramethyluronium hexafluorophosphate.
"HCl" refers to hydrochloric acid.
"HOBt" refers to 1-hydroxybenzotriazole monohydrate.
"HPLC" refers to high pressure liquid chromatography.
"2-PrPen" refers to 2-propylpentanoyl.
"LiAlH$_4$" refers to lithium aluminum hydride.
"LiAlH$_2$(OEt)$_2$" refers to lithium aluminum dihydride diethoxide.
"NaOH" refers to sodium hydroxide.
"NMM" refers to N-methylmorpholine.
"TBTU" refers to 2-(1H-benzotriazol-1-yl)-1,1,3,3-tetramethyluronium tetrafluoroborate.
"THF" refers to tetrahydrofuran.
"TLC" refers to thin layer chromatography.

DETAILED DESCRIPTION OF THE INVENTION

1. Preferred Compounds

Figure 1:
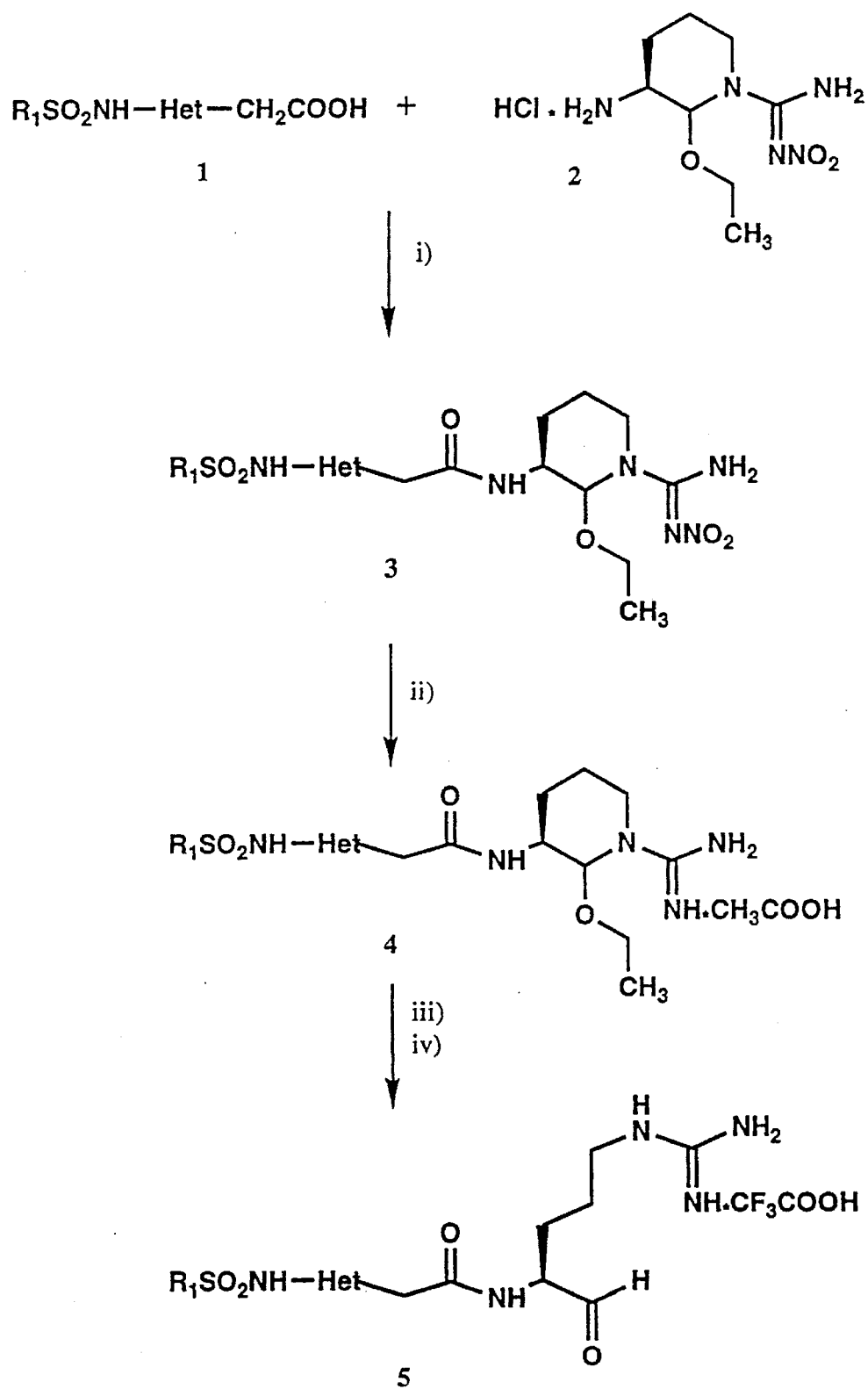
FIG. 1 depicts a general reaction scheme for preparation of certain compounds of the present invention. In this figure, "i" through "iv" are defined as: i) N-hydroxybenzotriazole, 1-ethyl-3-(3-dimethylaminopropyl)carbodiimide hydrochloride salt and N-methylmorpholine; ii) hydrogen gas, palladium on carbon, ethanol, acetic acid and water; iii) 3N HCl; and iv) sodium acetate, followed by HPLC purification using 0.1% trifluoroacetic acid in acetonitrile and water.

Compounds of the present invention have the formula:

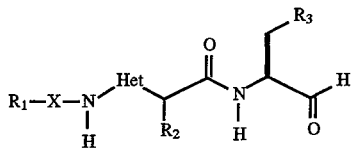

wherein (a) X is selected from the group consisting of $—S(O)_2—$, $—N(R')—S(O)_2—$, $—(C=O)—$, $—OC(=O)—$, $—NH—C(=O)—$, $—P(O)(R'')—$ and a direct link, wherein R' is hydrogen, alkyl of 1 to about 4 carbon atoms, aryl of about 6 to about 14 carbon atoms or aralkyl of about 6 to about 16 carbon atoms, and R" is NR', OR', R', or SR', with the proviso that R" is not NH, OH, H, or SH, and;

(b) $R_1$ is selected from the group consisting of:
(1) alkyl of 1 to about 12 carbon atoms,
(2) alkyl of 1 to about 3 carbon atoms substituted with cyclic alkyl of about 5 to about 8 carbon atoms, which optionally is substituted in the ring carbons with hydroxyl, amino, guanidino, amidino, or alkoxyl or alkyl each of 1 to about 3 carbons,
(3) cyclic alkyl of 3 to about 15 carbon atoms, which optionally is substituted in the ring carbons with hydroxyl, amino, guanidino, amidino, or alkoxyl or alkyl each of 1 to about 3 carbons, (4) heterocycloalkyl of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, optionally substituted in the ring carbons with hydroxyl, alkoxyl or alkyl each of 1 to about 3 carbons, amino, guanidino, or amidino, (5) heterocyclo of 4 to about 10 ring atoms with the ring atoms selected from carbon and heteroatoms, wherein the heteroatoms are selected from the group consisting of oxygen, nitrogen, and $S(O)_i$, wherein i is 0, 1 or 2, optionally substituted in the ring carbons with hydroxyl, alkoxyl, or alkyl each of 1 to about 3 carbons, amino, guanidino, or amidino, (6) alkenyl of about 3 to about 6 carbon atoms which is optionally substituted with cyclic alkyl of about 5 to about 8 carbon atoms, which optionally,is substituted in the ring carbons with hydroxyl, amino, guanidino, amidino, or alkoxyl or alkyl each of 1 to about 3 carbons, (7) aryl of about 6 to about 14 carbon atoms which is optionally mono-, di- or tri-substituted with $Y_1$, $Y_2$, and/or $Y_3$, respectively, (8) heteroaryl of 5 to 14 atoms with the ring atoms selected from carbon and heteroatoms, wherein the heteroatoms are selected from oxygen, nitrogen, and $S(O)_i$, wherein i is 0, 1 or 2, optionally mono-, di- or tri-substituted with $Y_1$, $Y_2$, and/or $Y_3$, respectively, (9) aralkyl of about 7 to about 15 carbon atoms which is optionally mono-, di-, or tri-substituted in the aryl ring with $Y_1$, $Y_2$, and/or $Y_3$, respectively,

(10) heteroaralkyl of 6 to 11 atoms with the ring atoms selected from carbon and heteroatoms, wherein the heteroatoms are selected from oxygen, nitrogen, and $S(O)_i$, wherein i is 0, 1 or 2, optionally mono-, di- or tri-substituted on the ring with $Y_1$, $Y_2$, and/or $Y_3$, respectively,

(11) aralkenyl of about 8 to about 15 carbon atoms which is optionally mono-, di-, or tri-substituted in the aryl ring with $Y_1$, $Y_2$, and/or $Y_3$, respectively,

(12) heteroaralkenyl of 7 to 12 atoms with the ring atoms selected from carbon and heteroatoms, wherein the heteroatoms are selected from oxygen, nitrogen, and $S(O)_i$, wherein i is 0, 1 or 2, optionally mono-, di- or tri-substituted with $Y_1$, $Y_2$, and/or $Y_3$, respectively,

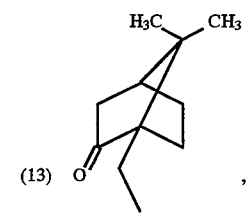

(13)

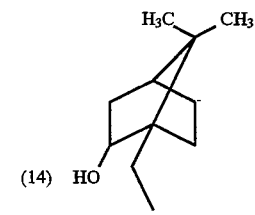

(14)

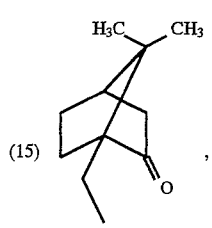

(15)

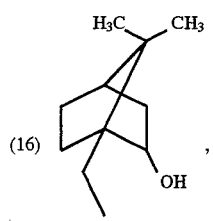

(16)

(17) perfluoroalkyl of 1 to about 12 carbon atoms,
(18) perfluoroaryl of about 6 to about 14 carbon atoms,
(19) perfluoroaralkyl of about 7 to about 15 carbon atoms,
(20) hydrogen, and
(21)

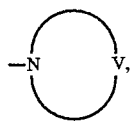

wherein

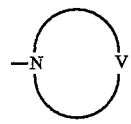

is a 5 to 7 member heterocycle of 3 to 6 ring carbon atoms, where V is —$CH_2$—, —O—, —S(=O)—, —$S(O)_2$— or —S—, wherein $Y_1$, $Y_2$, and $Y_3$ are (i) independently selected from the group consisting of hydrogen, halogen, cyano, tetrazolyl, amino, guanidino, amidino, methylamino, and methylguanidino, —$CF_3$, —$CF_2H$, —$CF_2CF_3$, —$CH(CF_3)_2$, —$C(OH)(CF_3)_2$, $OCF_3$, $OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —C(O)OH, —$C(O)NH_2$, —$C(O)NHZ_1$, —$C(O)OZ_1$, —$P(O)_3H$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, and —$NZ_1Z_2$, wherein m is 0, 1 or 2, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or (ii) $Y_1$ and $Y_2$ are selected together to be —$OC(Z_3)(Z_4)O$—, wherein $Z_3$ and $Z_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, (c) $R_2$ is selected from the group consisting of hydrogen, alkyl of 1 to about 4 carbon atoms, and alkenyl of about 2 to about 4 carbon atoms, (d) $R_3$ is selected from the group consisting of

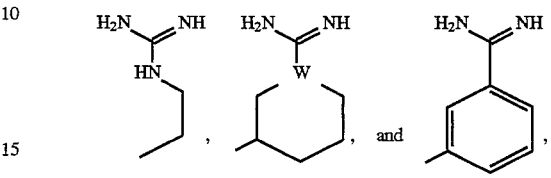

where W is nitrogen or carbon;

(e) Het is selected from the group consisting of

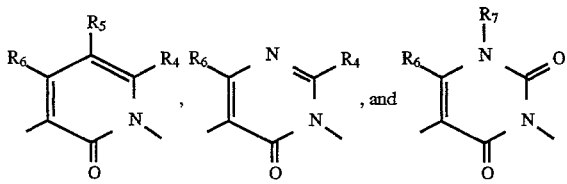

wherein (1) $R_4$ is selected from the group consisting of $R_1$, —$OR_1$, —$NHR_1$, —$S(O)_nR_1$, and halogen, wherein n is 0, 1 or 2, and $R_1$ is independently selected and as defined above, (2) $R_5$ is selected from the group consisting of $R_1$, —$OR_1$, —$NHR_1$, —$S(O)_nR_1$, and halogen, wherein n is is 0, 1 or 2, and $R_1$ is independently selected and as defined above, (3) $R_6$ is selected from the group consisting of $R_1$, —$OR_1$, —$NHR_1$, —$S(O)_nR_1$, and halogen, wherein n is 0, 1 or 2, and $R_1$ is independently selected and as defined above.

(4) $R_7$ is independently selected from the $R_1$ group of substituents, as defined above.

Preferred X groups include —$SO_2$—, —NH—$S(O)_2$—, and —N(R')—$S(O)_2$. Especially preferred X groups include —$SO_2$.

Preferred $R_1$ groups include alkyl, aralkyl, and aryl groups. Preferred aryl groups include substituted or unsubstituted phenyl and naphthyl. Preferred substitutions include, methyl, methoxy, fluoro, chloro, trifluoromethyl, and —$OCF_3$. Meta and ortho substitution is preferred. Meta and ortho di-substitution is particularly preferred.

Particularly preferred $R_1$ groups include aralkyl groups. Especially preferred $R_1$ groups include substituted or unsubstituted benzyl and naphthyl groups. Cyclohexyl and cyclohexylmethyl are especially preferred $R_1$ groups.

A particularly preferred $R_2$ group is hydrogen.

Preferred $R_3$ groups include

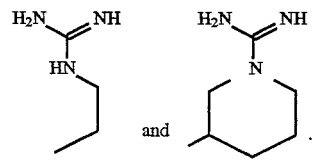

19

Preferred R$_4$ groups include:
(i) hydrogen,
(ii) alkyl of 1 to 6 carbon atoms substituted with Z$_5$, wherein Z$_5$ is selected from the group consisting of hydrogen, —CH$_3$, halogen, —C(O)OH, —C(O)OR$_8$, —S(O)$_3$OH and —S(O)$_p$R$_8$ wherein R$_8$ is alkyl of 1 to about 4 carbon atoms, and p is 0–2,
(iii) alkyl of 1 to 3 carbon atoms substituted with cyclic alkyl of 3–5 carbon atoms,
(iv) alkenyl of about 3 to about 6 carbon atoms,
(v) alkyl substituted with Z$_6$, wherein Z$_6$ is selected from the group consisting of hydrogen, halogen, —C(O)OH, —C(O)OR$_9$, —S(O)$_3$OH and —S(O)$_p$R$_9$ wherein R$_9$ is alkyl of 1 to about 6 carbon atoms, and n is 0–2,
(vi) cycloalkyl of about 3 to about 5 carbon atoms,
(vii) heteroaryl having 1 to about 4 ring carbon atoms with the ring atoms selected from carbon and heteroatoms, wherein the heteroatoms are selected from oxygen, sulfur and nitrogen, and
(viii) heteroaralkyl of 2 to about 6 carbon atoms with the ring atoms selected from carbon and heteroatoms, wherein the heteroatoms are selected from oxygen, sulfur and nitrogen.

Preferred R$_5$ groups include hydrogen, alkyl of 1 to about 5 carbon atoms, trifluoromethyl,and —OR$_{10}$, wherein R$_{10}$ is an alkyl of 1–4 carbon atoms. Hydrogen is an especially preferred R$_5$ group.

Preferred R$_6$ groups include:
(i) hydrogen,
(ii) alkyl of 1 to about 12 carbon atoms substituted with Z$_7$, wherein Z$_7$ is selected from the group consisting of hydrogen, hydroxy, halogen, —OR$_{11}$, NHR$_{11}$—C(O) OH, —C(O)OR$_{11}$, —S(O)$_2$OH and —S(O)$_p$R$_{11}$, wherein R$_{11}$ is alkyl of 1 to about 12 carbon atoms, aryl of about 6 to about 10 carbon atoms, aralkyl of about 7 to about 12 carbon atoms, heteroaryl of 1 to about 9 carbon atoms with the ring atoms selected from carbon and heteroatoms, wherein the heteroatoms are selected from oxygen, sulfur and nitrogen, optionally mono-, di- or tri-substituted on the ring with Y$_1$, Y$_2$ and/or Y$_3$, as defined above, and heteroaralkyl of about 2 to about 10 carbon atoms with the ring atoms selected from carbon and heteroatoms, wherein the heteroatoms are selected from oxygen, sulfur and nitrogen, optionally mono-, di- or tri-substituted on the ring with Y$_1$, Y$_2$ and/or Y$_3$, as defined above, and p is 0, 1 or 2;
(iii) alkyl of 1 to about 3 carbon atoms substituted with cyclic alkyl of about 5 to about 8 carbon atoms;
(iv) alkenyl of about 2 to about 6 carbon atoms which is optionally substituted with cyclic alkyl of about 3 to about 8 carbon atoms, aryl of about 6 to about 10 carbon atoms or heteroaryl of 1 to about 9 carbon atoms;
(v) aralkyl of about 7 to about 15 carbon atoms which is optionally substituted on the alkyl chain with hydroxy or halogen, and optionally mono-, di- or tri-substituted on the ring with Y$_1$, Y$_2$ and/or Y$_3$, as defined above;
(vi) heteroaralkyl of about 5 to about 10 ring atoms having 1 to about 9 ring carbon atoms with the ring atoms selected from carbon and heteroatoms, wherein the heteroatoms are selected from oxygen, sulfur and nitrogen, optionally substituted on the alkyl chain with hydroxy or halogen, and optionally mono-, di- or tri-substituted on the ring with Y$_1$, Y$_2$ and/or Y$_3$, as defined above;

20

(vii) aralkenyl of about 6 to 15 carbon atoms which is optionally mono-, di- or tri-substituted on the ring with Y$_1$, Y$_2$ and/or Y$_3$, as defined above;
(viii) heteroaralkenyl ring of about 5 to about 10 ring atoms with 1 to 9 ring carbon atoms with the ring atoms selected from carbon and heteroatoms, wherein the heteroatoms are selected from oxygen, sulfur and nitrogen, optionally mono-, di- or tri-substituted on the ring with Y$_1$, Y$_2$ and/or Y$_3$, as defined above.

More preferred R$_6$ groups, when R$_4$ and R$_5$ are hydrogen or methyl, are selected from the group consisting of aralkyl of about 8 to about 13 carbon atoms, and —O-aralkyl, —NH-aralkyl, and —S(O)$_p$-aralkyl of about 7 to about 12 carbon atoms. Preferred aryl, of the aralkyl, groups include unsubstituted and substituted phenyl or naphthyl. Preferred substitutions on the aryl ring include methyl, methoxy, fluoro, chloro and trifluoromethyl. Phenylethyl, phenylpropyl, cyclohexylethyl and cyclohexylpropyl are especially preferred R$_6$ groups.

Preferred R$_7$ groups include hydrogen, methyl, difluoromethyl and trifluoromethyl. Hydrogen is an especially preferred R$_7$ group.

Preferred Het groups include

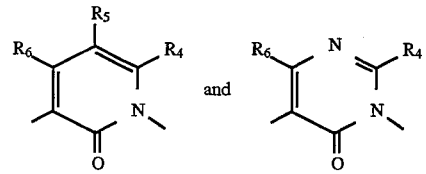

A particularly preferred Het, when R$_5$ and R$_6$ are independently selected to be hydrogen or methyl, is

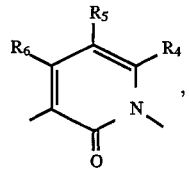

wherein R$_4$ is selected from the group consisting of hydrogen, methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrolyl, 3-pyrolyl, 1-hexyl, S-2-hexyl, R-2-hexyl, R-3-hexyl, and S-3-hexyl. A particularly preferred Het according to this aspect has hydrogen or metal as R$_4$.

According to a particularly preferred aspect, provided are compounds of formula I wherein X is —S(O)$_2$—, R$_1$ is substituted or unsubstituted aryl or aralkyl, R$_3$ is

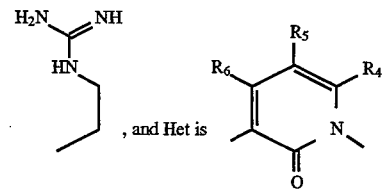

A very preferred aspect is directed to such compounds where R$_1$ is substituted or unsubstituted benzyl or phenyl.

Preferred compounds include
3-[(phenylsulfonyl)amino-2-oxo-1,2-dihydropyridylacetyl-L-argininal (Example 90, compound B), 3-[(2-naphthylsulfonyl)amino]-2-oxo-1,2-dihydropyridylacetyl-L-argininal (Example 90),
3-[(1-naphthylsulfonyl)amino]-2-oxo-1,2-dihydropyridylacetyl-L-argininal (Example 90),
3-(cyclohexylaminosulfonylamino-2-oxo-1,2-dihydropyridyl)acetyl-L-argininal (Example 90),
3-(phenylaminosulfonylamino-2-oxo-1,2-dihydropyridylacetyl-L-argininal,
3-[(phenoxycarbonyl)amino]-2-oxo-1,2-dihydropyridylacetyl-L-argininal,
3-[(cyclohexylsulfonyl)amino]-2-oxo-1,2-dihydropyridylacetyl-L-argininal,
3-[(cyclohexylmethylsulfonyl)amino]-2-oxo-1,2-dihydropyridylacetyl-L-argininal,
3-[(phenethylsulfonyl)amino]-2-oxo-1,2-dihydropyridylacetyl-L-argininal,
3-[(2-methoxycarbonylphenylsulfonyl)amino]-2-oxo-1,2-dihydropyridylacetyl-L-argininal,
3-[(3-methoxycarbonylphenylsulfonyl)amino]-2-oxo-1,2-dihydropyridylacetyl-L-argininal,
3-[(4-methoxycarbonylphenylsulfonyl)amino]-2-oxo-1,2-dihydropyridylacetyl-L-argininal,
3-[(2-trifluoromethylphenylsulfonyl)amino]-2-oxo-1,2-dihydropyridylacetyl-L-argininal (Example 90),
3-[(3-trifluoromethylphenylsulfonyl)amino]-2-oxo-1,2-dihydropyridylacetyl-L-argininal (Example 90),
3-[(4-trifluoromethylphenylsulfonyl)amino]-2-oxo-1,2-dihydropyridylacetyl-L-argininal (Example 90),
3-[(2-methoxycarbonylbenzylsulfonyl)amino]-2-oxo-1,2-dihydropyridylacetyl-L-argininal,
3-[(3-methoxycarbonylbenzylsulfonyl)amino]-2-oxo-1,2-dihydropyridylacetyl-L-argininal,
3-[(4-methoxycarbonylbenzylsulfonyl)amino]-2-oxo-1,2-dihydropyridylacetyl-L-argininal,
3-[(2-trifluoromethylbenzylsulfonyl)amino]-2-oxo-1,2-dihydropyridylacetyl-L-argininal (Example 90),
3-[(3-trifluoromethylbenzylsulfonyl)amino]-2-oxo-1,2-dihydropyridylacetyl-L-argininal,
3-[(4-trifluoromethylbenzylsulfonyl)amino]-2-oxo-1,2-dihydropyridylacetyl-L-argininal,
[3-[(benzylsulfonyl)amino]-2-oxo-1,2-dihydropyridyl]acetyl-L-argininal (Example 10),
[3-[(benzylsulfonyl)amino]-6-methyl-2-oxo-1,2-dihydropyridyl]acetyl-L-argininal (Example 19, and 112, compound C),
5-benzylsulfonylamino-6-oxo-1,6-dihydro-1-pyrimidinylacetyl-L-argininal (Example 29b),
2-methyl-5-benzylsulfonylamino-6-oxo-1,6-dihydro-1-pyrimidinylacetyl-L-argininal (Example 40, and 112, compound D),
5-benzylsulfonylamino-uracilylacetyl-L-argininal,
5-benzylsulfonylamino-1-methyl-uracilylacetyl-L-argininal (Example 54),
3-{(2-trifluoromethylbenzylsulfonyl)amino]-2-oxo-1,2-dihydropyridyl acetyl-L-argininal,
[3-[(benzylsulfonyl)amino]-2-oxo-1,2-dihydropyridyl] acetyl-3-[3-piperidyl-(N-guanidino)]alaninal, and
[3-[(benzylsulfonyl)amino]-2-oxo-1,2-dihydropyridyl] acetyl-D,L-3-amidinophenyl alaninal.

According to another aspect, the present invention is directed to salts of the compounds of formula (I). "Salt" includes within its definition, salts of the compounds of the present invention derived from the combination of such compounds and an organic or inorganic acid. In practice, the use of the salt form amounts to use of the base form. The compounds of the present invention are useful in both free base and salt form, with both forms being considered as being within the scope of the present invention. These salts include acid addition salts, for example, salts of hydrochloric acid, hydrobromic acid, acetic acid, benzene sulfonic acid and other suitable acid addition salts.

2. Preparation of Preferred Compounds

FIG. 1 exemplifies a preferred reaction scheme for the synthesis of certain compounds of the present invention. $N^g$-nitro-L-argininal ethyl cyclol, hydrochloride salt 2 is coupled to the terminal carboxyl of the $R_1$ sulfonyl amino heterocycle 1 to give 3. Especially preferred coupling reagents are N-hydroxybenzotriazole in acetonitrile with 1-ethyl-3-(3-dimethylaminopropyl)carbodiimide hydrochloride salt. 3 is hydrogenated with hydrogen gas and palladium on carbon to remove the $N^g$-nitro group to give 4. 4 is then treated with strong acid and purified by HPLC with trifluoroacetic acid in the solvent to produce argininal 5.

The compounds of the present invention may be prepared by the preferred reaction schemes depicted in FIGS. 2 through 5. Examples 5 through 10 provide the details of the preferred scheme of FIG. 2. Examples 20 through 29 provide the details for the preferred scheme of FIG. 3. Examples 41 through 47 provide the details for the preferred scheme of FIG. 4, and Examples 55 through 63 provide the details for the preferred scheme of FIG. 5.

In these reaction schemes, intermediates, which include 9, 18, 26, and 36 shown in FIGS. 2 through 5, respectively, are coupled to argininal or argininal mimic moieties to eventually give the compounds of the present invention. Examples 1 through 4 provide the details for the preparation of the precursor to the argininal moiety used in FIGS. 2 through 4. Examples 55 through 57 provide the details for the preparation of the argininal precursor used when hydrogenation sensitive groups exist. Examples 64 through 71 provide the details for the preparation of compounds of the present invention possessing a 3-[3-piperidyl-(N-guanidino)] alaninal in the $P_1$ position.

The preferred means of chemically coupling (as for example, 9 to 10 of FIG. 2 or 18 to 19 of FIG. 3) include formation of a peptide bond by using conventional coupling reagents known in the art. See Bodanszky, N., Peptide Chemistry, pp. 55–73, Springer-Verlag, New York (1988) and references cited therein. The chemical coupling may be either by means of one-step or two-step coupling. In one-step coupling, the two coupling partners are coupled directly. Preferred coupling reagents for one-step coupling of the include DCC with HOBt, EDC with HOBt, HBTU or TBTU. In two-step coupling, an activated ester or anhydride of the C-terminal carboxy group of one coupling partner is formed prior to its coupling to the other coupling partner.

Figure 2:
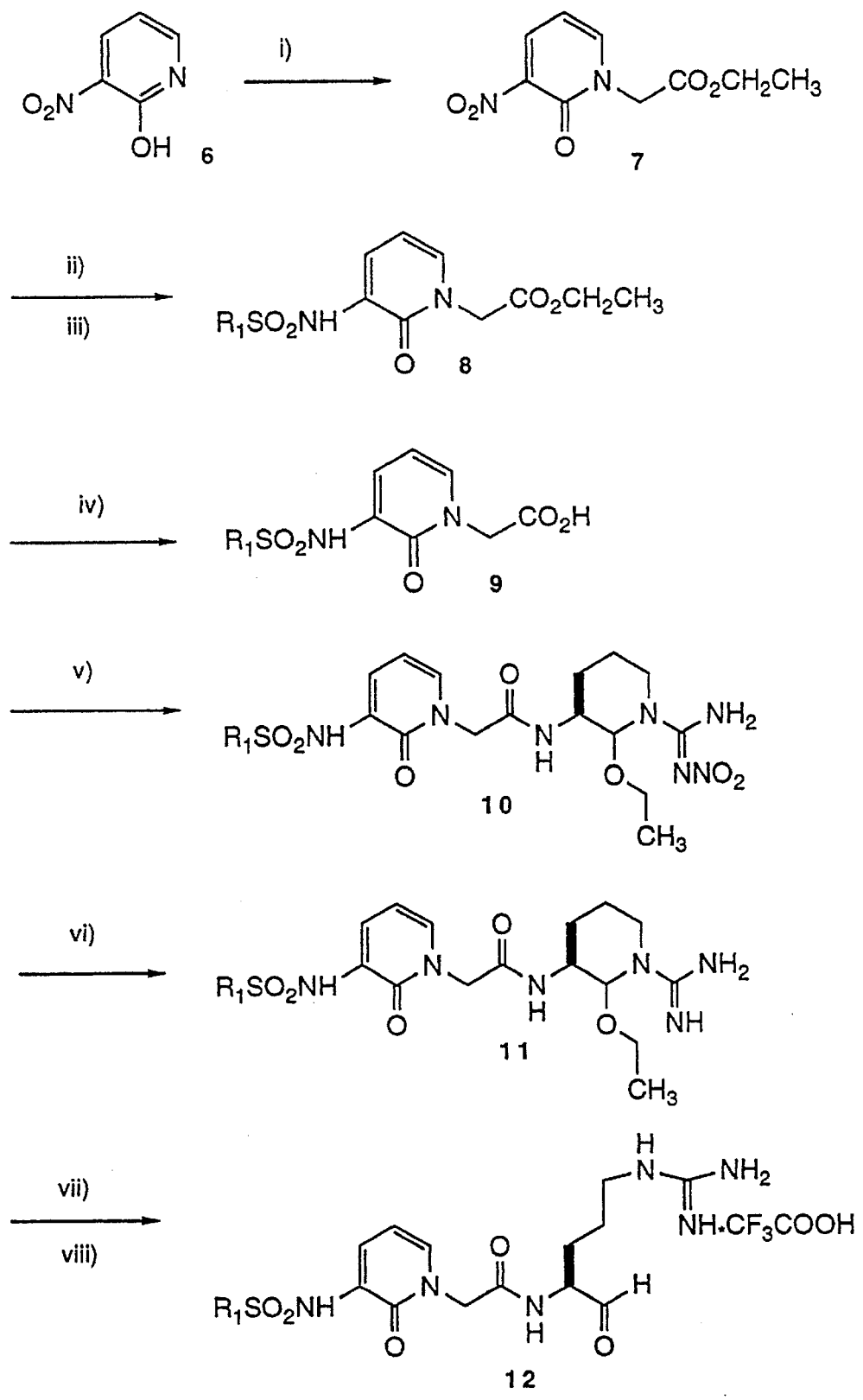
FIG. 2 depicts a general reaction scheme for preparation of certain compounds of the present invention. In this figure, i)–viii) are defined as: i) sodium hydride and ethyl bromoacetate; ii) hydrogen gas and palladium on carbon; iii) collidine and R$_1$—SO$_2$—Cl, where R$_1$ is as defined herein; iv) sodium hydroxide and methanol; v) N$^g$-nitro-L-argininal ethyl cyclol, hydrochloride salt, N-hydroxybenzotriazole, 1-ethyl-3-(3-dimethylaminopropyl)carbodiimide hydrochloride salt and N-methylmorpholine; vi) hydrogen gas, palladium on carbon, ethanol, acetic acid and water; vii) 3N HCl; and viii) sodium acetate, and then HPLC purification using 0.1% trifluoroacetic acid in acetonitrile and water.

For example, as shown in FIG. 2, the nitrogen of the pyridine ring of 6 is alkylated to give 7. The nitro group is then reduced to the amine, which is then reacted with a sulfonyl chloride, depicted by $R_1$—$S(O)_2$—Cl, to give 8. $R_1$ is as defined herein. The ethyl ester of 8 is removed by treatment with sodium hydroxide in methanol to give the carboxylic acid 9. The acid of 9 is coupled to $N^g$-nitro-L-argininal ethyl cyclol HCl salt by carbodiimide coupling to give 10. 6-Alkylated pyridyl compounds are made according to Examples 11 through 19. 10 is hydrogenated with hydrogen gas and palladium on carbon to remove the $N^g$-nitro group to give 11. 11 is hydrolyzed in aqueous acid to give 12.

Figure 3:
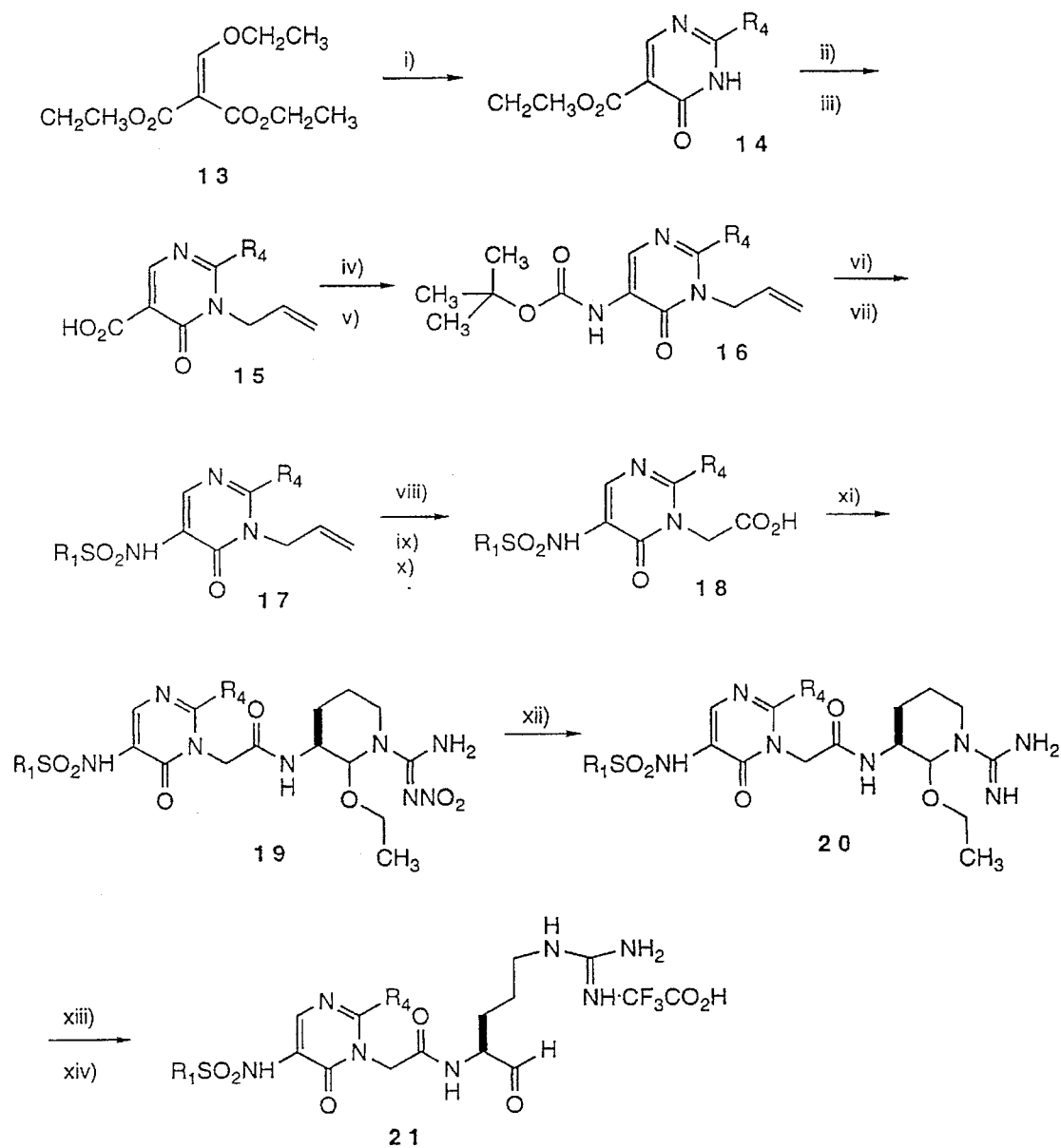
FIG. 3 depicts a general reaction scheme for preparation of certain compounds of the present invention. In this figure, i)–xiv) are defined as: i) R$_4$—C(=NH)—NH$_2$, where R$_4$ is as defined herein; ii) sodium hydride, allyl bromide; iii) sodium hydroxide; iv) triethylamine, diphenylphosphoryl azide and heat; v) t-butyl alcohol and heat; vi) trifluoroacetic acid; vii) collidine and R$_1$—SO$_2$—Cl, where R$_1$ is as defined herein; viii) N-methylmorpholine-N-oxide and osmium tetroxide; ix) sodium periodate; x) sodium chlorite; xi) N$^g$-nitro-L-argininal ethyl cyclol, hydrochloride salt, N-hydroxybenzotriazole, 1-ethyl-3-(3-dimethylaminopropyl)carbodiimide hydrochloride salt and N-methylmorpholine; xii) palladium on carbon, ethanol, acetic acid and water; xiii) 3N HCl; and xiv) sodium acetate, and then HPLC purification using 0.1% trifluoroacetic acid in acetonitrile and water.

FIG. 3 provides a preferred reaction scheme for preparing pyrimidyl compounds of the present invention. Examples 21 through 29 describe this preparation. Pyrimidine 14 is alkylated with allyl bromide, and then the ester is hydrolyzed with sodium hydroxide in methanol to give the 1-allyl pyrimidone 15. 15 is then treated with triethylamine and diphenylphosphoryl azide to form the acyl azide which undergoes the Curtius rearrangement. Reaction with t-butanol forms the BOC protected 5-aminopyrimidone 16. Treatment with acid removes the BOC group. The amine is then reacted with an alkyl sulfonyl chloride to give 17. 17 is oxidized in three steps to form 18, which undergoes coupling as previously described.

Figure 9:
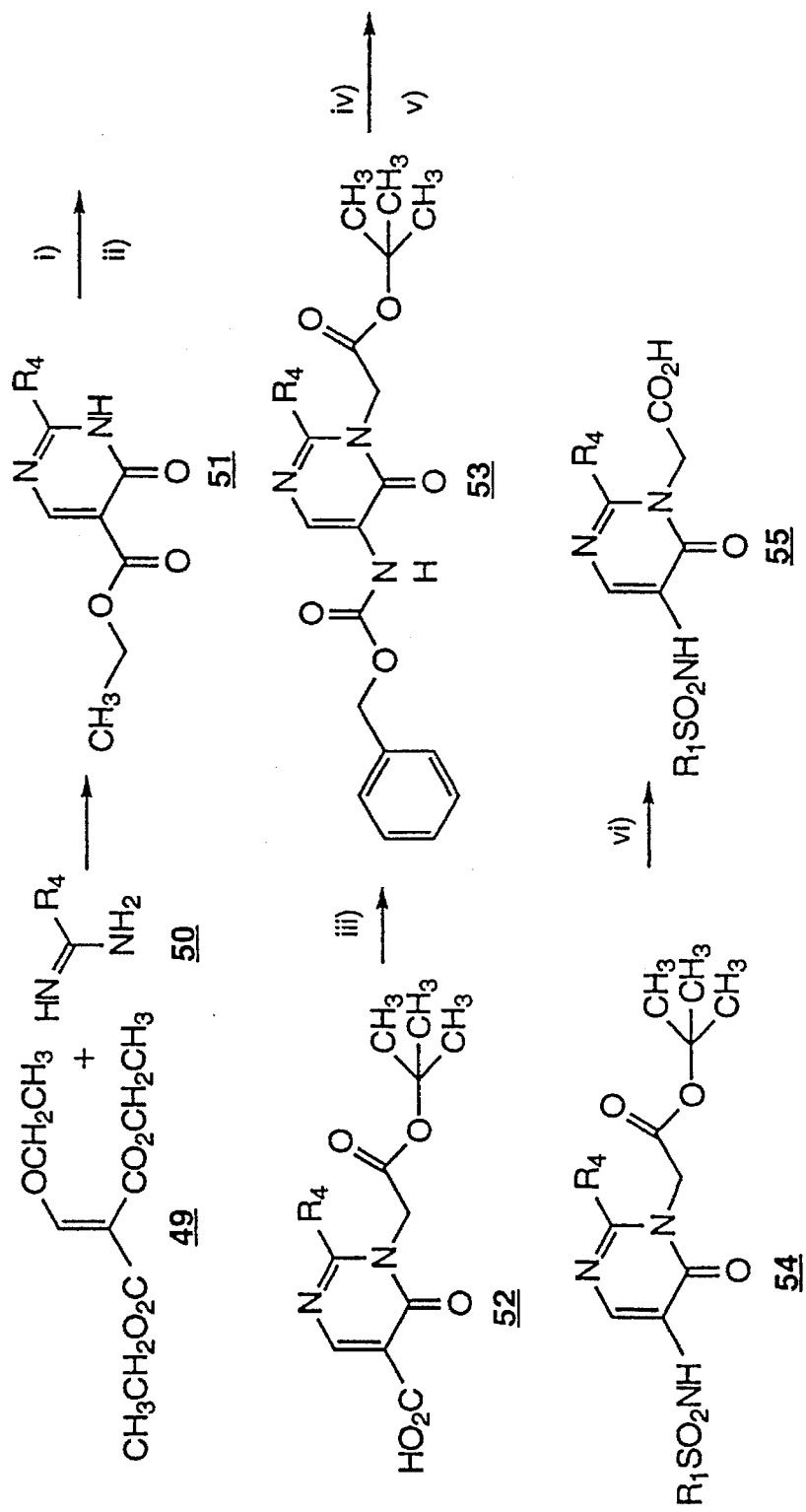
FIG. 9 depicts a reaction scheme for the preparation of certain compounds of the present invention, including compound 18 in FIG. 3. In this Figure, i) through vi) are: I) NaH, DMF, and $BrCH_2CO_2t$-Bu; ii) LiOH and THF; iii) $Et_3N$, DPPA, dioxane and $\Delta$; BnOH and $\Delta$; iv) $H_2$ and Pd/C; v) $R_1SO_2Cl$ and NMM and vi) TFA; See also Examples 102–107. $R_1$ and $R_4$ are as defined herein.

FIG. 9 provides an alternate preferred reaction scheme for preparing intermediate compound 18 of FIG. 3. Synthesis of 18 by this alternate route is as described in Examples 102–107.

Figure 4:
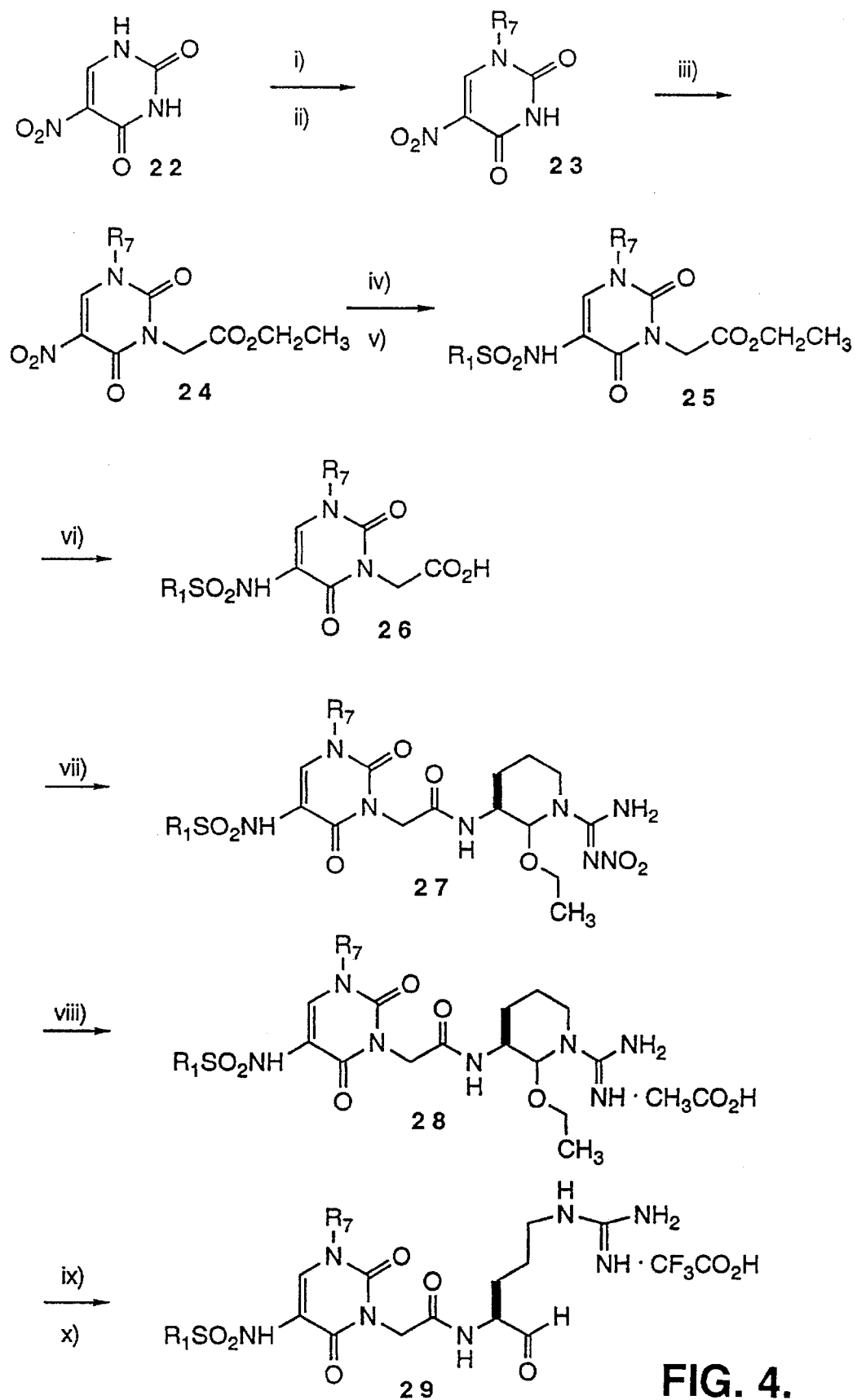
FIG. 4 depicts a general reaction scheme for preparation of certain compounds of the present invention. In this figure, i)–x) are defined as: i) 1,1,1-3,3,3-hexamethyldisilazane and chlorotrimethylsilane; ii) R$_7$X heated in dimethylformamide, wherein R$_7$ is as defined herein and X is a halogen; iii) tetrabutylammonium flouride and ethyl bromoacetate; iv) hydrogen gas and palladium on carbon; v) collidine and R$_1$—SO$_2$—Cl, where R$_1$ is as defined herein; vi) sodium hydroxide; vii) N$^g$-nitro-L-argininal ethyl cyclol, hydrochloride salt, N-hydroxybenzotriazole, 1-ethyl-3-(3-dimethylaminopropyl)carbodiimide hydrochloride salt and N-methylmorpholine; viii) palladium on carbon, ethanol, acetic acid and water; ix) 3N HCl; and x) sodium acetate, and then HPLC purification using 0.1% trifluoroacetic acid in acetonitrile and water.

FIG. 4 provides a preferred reaction scheme for preparing uracil compounds of the present invention. Examples 41 through 54 describe this preparation. As shown in FIG. 4, 5-nitrouracil 22 is reacted with 1,1,1,3,3,3-hexamethyldisilazane and chlorotrimethylsilane to give the 5-nitrouracil bis(trimethylsilyl) ether, which is then reacted with bromomethylmethyl ether to give the methorymethyl uracil 23. This compound is then reacted with ethyl bromoacetate to give the ethyl uracilylacetate 24. The nitro group is then reduced to the amine using hydrogen gas and palladium on carbon. The amine is then treated with 2,4,6-collidine and $R_1SO_2Cl$ to give the amide 25. The ethyl ester is converted to acid 26 by treatment with sodium hydroxide in methanol. The acid of 26 is coupled to $N^g$-nitro-L-argininal ethyl cyclol hydrochloride salt (prepared according to Examples 1 through 4). The adduct 27 is deprotected by treatment with hydrogen gas and palladium on carbon in an ethanol, acetic acid, and water mixture. 28 is hydrolized with 3N hydrochloric acid and then purified by HPLC with a solvent containing 0.1% trifluoroacetic acid to give argininal 29.

Figure 10:
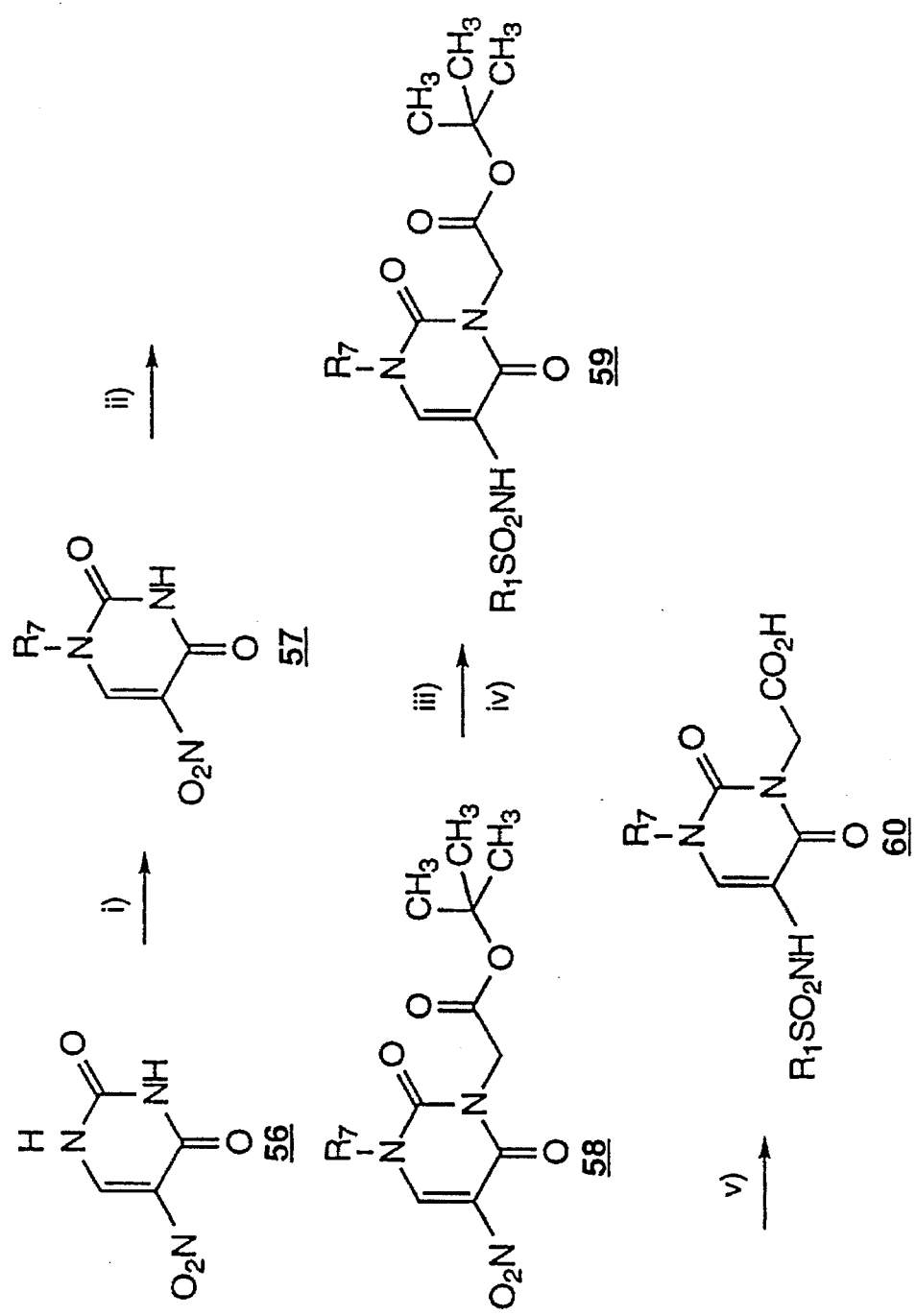
FIG. 10 depicts a reaction scheme for the preparation of certain compounds of the present invention, including compound 26 in FIG. 4. In this Figure, i) through v) are: $K_2CO_3$, $R_7X$ and DMSO; ii) NaH and $BrCH_2CO_2t$-Bu; iii) $H_2$ and 10% Pd/C; iv) $R_1SO_2Cl$ and NMM; and v) trifluoroacetic acid. See also Examples 108–111. R is $R_7$; $R_7$ and $R_4$ are as defined herein.

FIG. 10 provides an alternate preferred reaction scheme for preparing intermediate compound 26 of FIG. 4. Synthesis of 26 by this alternate route is as described in Examples 108–111.

Figure 5:
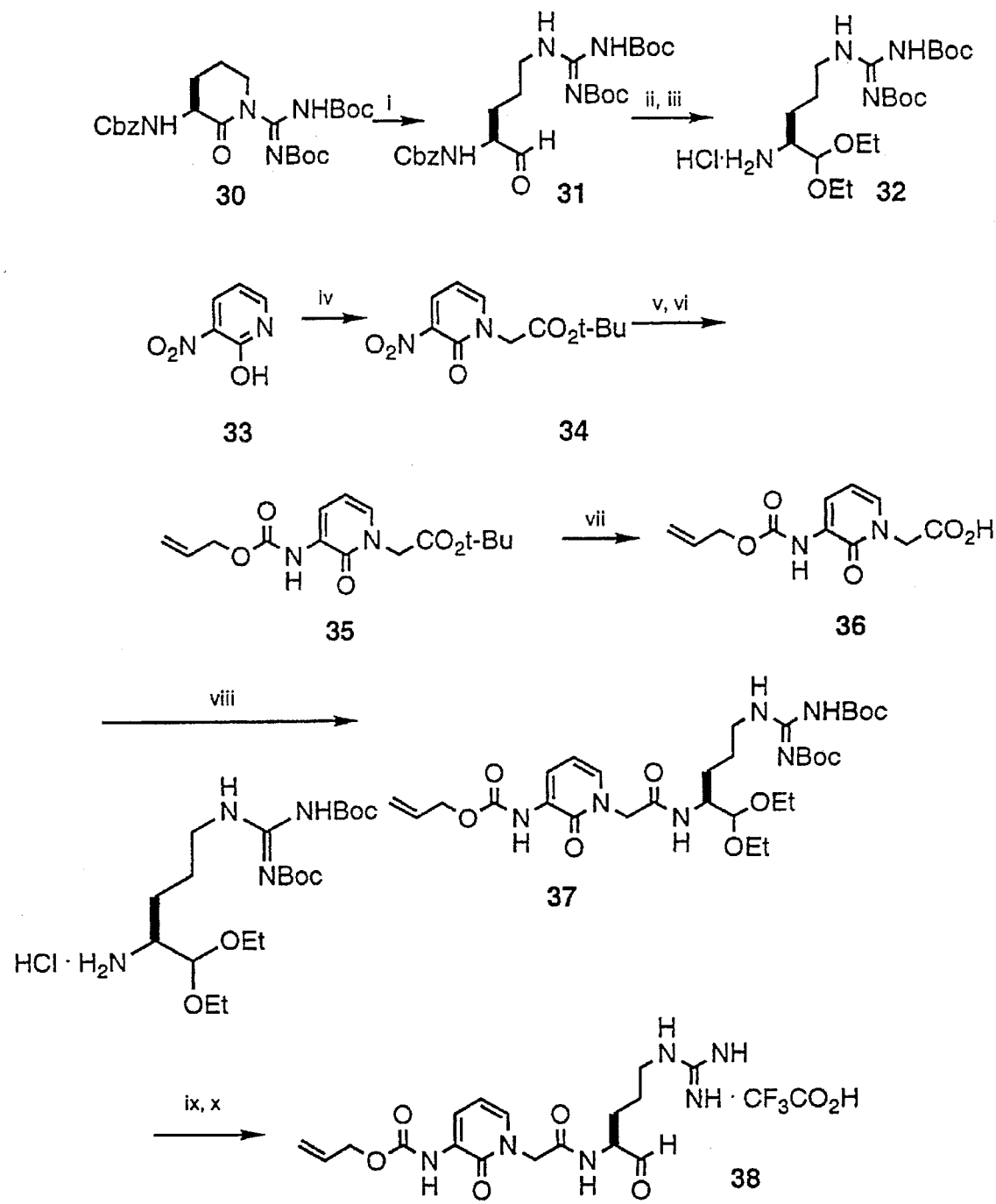
FIG. 5 depicts the reaction scheme for preparation of a compound of the present invention. In this figure, "Boc" refers to the protecting group, t-butoxycarbonyl; "Cbz" refers to the protecting group, benzyloxycarbonyl; and "t-Bu" refers to the protecting group, t-butyl. Also, in this figure, "i" through "x" are defined as: i) lithium aluminum hydride; ii) ethanol and HCl; iii) hydrogen gas and palladium on carbon; iv) sodium hydride and t-butyl bromoacetate; v) hydrogen gas and palladium on carbon; vi) sodium bicarbonate and allyl chloroformate; vii) trifluoroacetic acid; viii) N-hydroxybenzotriazole, 1-ethyl-3-(3-dimethylaminopropyl)carbodiimide hydrochloride salt and N-methylmorpholine; ix) hexafluorophosphoric acid; and x) sodium acetate and then HPLC purification using 0.1% trifluoroacetic acid in acetonitrile and water.
Figure 6:
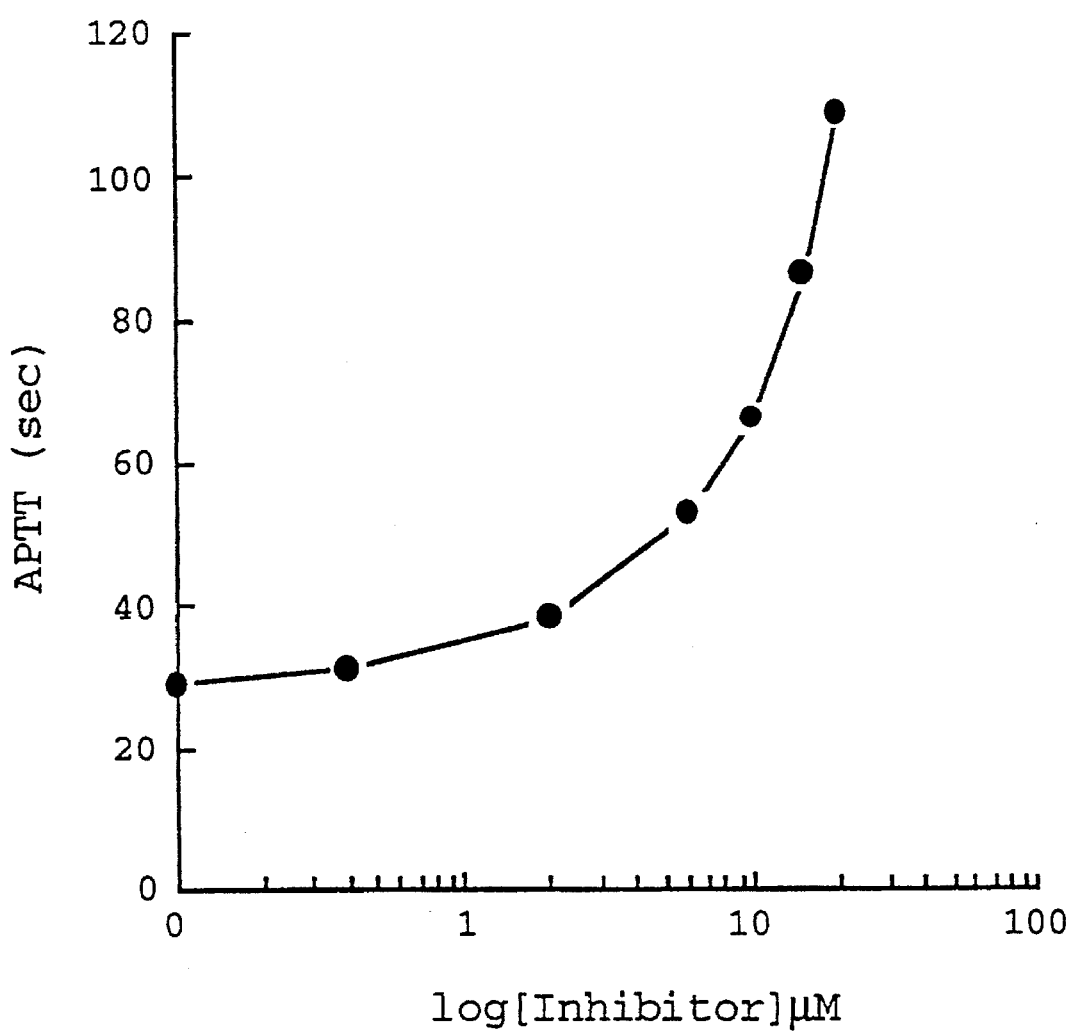
FIG. 6 depicts the anticoagulant effect of [3-[(benzylsulfonyl)amino]-2-oxo-1,2-dihydropyridyl]acetyl-L-arginal measured in citrated human plasma, closed circles (1), using the activated partial thromboplastin time (APTT) assay. The control clotting times (0 inhibitor) for human plasma was 29 seconds. The concentration of this compound of the present invention which caused a doubling of the control clotting time in human plasma was 7.7 micromolar. The data is the mean of two independent determinations.

FIG. 5 provides a preferred reaction scheme for preparing compounds of the invention possessing a hydrogenation sensitive moiety in the $P_4$ position. This method uses the di-N-t-butoxycarbonyl protecting group for the L-argininal moiety. This scheme has an alkenyl carbamate as the hydrogenation sensitive moiety. Examples 55 through 63 describe this preparation which uses hexafluorophosphoric acid to remove the BOC protecting groups. This general method can be used to prepare other hydrogenation sensitive compounds.

As described by Example 58, 3-nitro-2-hydroxypyridine 33 is treated with sodium hydride and then t-butyl bromoacetate to give 34. the nitro group of 34 is reduced to the amine by treatment with hydrogen gas and palladium on carbon. The amine is condensed with allyl chloroformate in the presence of sodium bicarbonate to give 35. The t-butyl group of 35 is removed by trifluoroacetic acid to give 36. Alpha-N-t-benzyloxycarbonyl-omega, omega'-di-N-t-butoxycarbonylarginine is dissolved in acetonitrile and treated with hydroxybenzotriazole and 1-ethyl-3-(3-dimethylaminopropyl)carbodiimide HCl salt to form alpha-N-benzyloxycarbonyl-omega, omega'-di-N-t-butoxycarbonyl-L-arginine lactam. The lactam 30 is opened by treatment with LiAlH$_4$ in tetrahydrofuran at −70° C. to provide alpha-N-benzyloxycarbonyl-omega, omega'-di-N-t-butoxycarbonyl-L-argininal 31. This aldehyde is protected as the diethyl acetal by treatment with ethanol and HCl. The N-benzyloxycarbonyl protecting group is removed by treatment with hydrogen gas and palladium on carbon to give omega, omega'-di-N-t-butoxycarbonyl-L-argininal diethyl acetal, HCl salt 32. This protected L-argininal moiety can then be coupled to a desired carboxylic acid, shown in the figure as 36, by treatment with N-hydroxybenzotriazole and 1-ethyl-3-(3-dimethylamino-propyl)carbodiimide HCl salt. The diethyl acetal and the di-BOC protecting groups are removed by treatment with hexafluorophosphoric acid in acetonitrile at 0° C. The reaction is quenched by adjusting to pH 4 with 2.5M aqueous sodium acetate. Preparative HPLC using 0.1% CF$_3$COOH in 10–40% aqueous acetonitrile provides the trifluoroacetate salt of the desired substituted L-argininal compound 38.

Another preferred method for preparing compounds of the present invention containing hydrogenation sensitive groups such as alkenyl or aryl moieties substituted with halogen, cyano, nitro, or —S—Z$_1$, is to use boron tris (trifluoroacetate), B(OCOCF$_3$)$_3$, to cleave the N$^g$-nitro of the arginine group. The reagent is prepared by the reaction of BBr$_3$ and CF$_3$COOH in dichloromethane at 0° C. The reagent is also commercially available. Generally, the N$^g$-nitro compound is treated with boron tris (trifluoroacetate) in trifluoroacetic acid at 0° C. Fieser, M. and Fieser, L. F., *Reagents for Organic Synthesis*, p. 46, John Wiley & Sons, New York (1974); Pless, J., and Bauer, W. *Angew. Chem., Internat. Ed.*, 12, 147 (1973).

Figure 7:
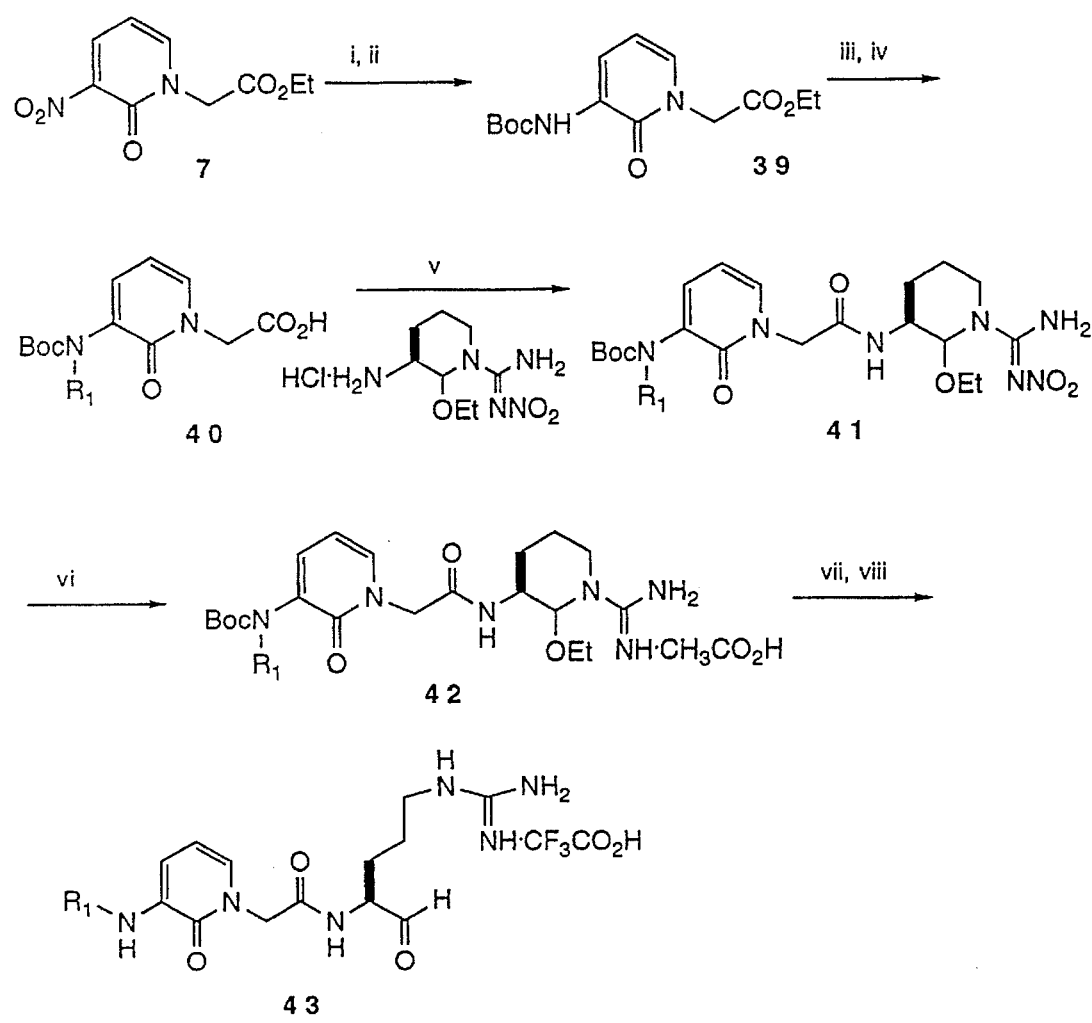
FIG. 7 depicts a reaction scheme for the preparation of compounds wherein X is a direct link. In this figure, i)–ix) are defined as i) hydrogen gas and palladium on carbon; ii) di-t-butyldicarbonate and sodium bicarbonate; iii) sodium hydride and R$_1$ iodide; iv) sodium hydroxide; v) EDC, HOBt, and N-methylmorpholine; vi) hydrogen gas and palladium on carbon, ethanol, acetic acid and water; vii) 3N hydrochloric acid; and viii) sodium acetate, and then HPLC purification using 0.1% trifluoroacetic acid in acetonitrile and water.

FIG. 7 illustrates a preferred reaction scheme for the preparation of compounds where X is a direct link. This figure is described by Examples 83 through 88.

As shown in FIG. 7, the nitro group of pyridone 7 is reduced by treatment with hydrogen gas and palladium on carbon. The amine is then protected by the Boc group to form 39. The Boc protected amine 39 is then treated with sodium hydride and alkylated with R$_1$ iodide, where R$_1$ is as defined herein. The ethyl ester is converted to acid 40 by sodium hydroxide. Acid 40 is then coupled to the compound of Example 4 by standard coupling techniques using 1-ethyl-3-(3-dimethylaminopropyl)carbodiimide hydrochloride salt, 1-hydroxybenzotriazole monohydrate, and N-methylmorpholine to give 41. The N$^g$-nitro group is removed by catalytic hydrogenation with palladium on carbon to give 42. The Boc protecting group is removed and the argininal is unmasked by treatment with HCl, followed by sodium acetate. HPLC purification with 0.1% trifluoroacetic acid gives the final product 43 in FIG. 7.

Figure 8:
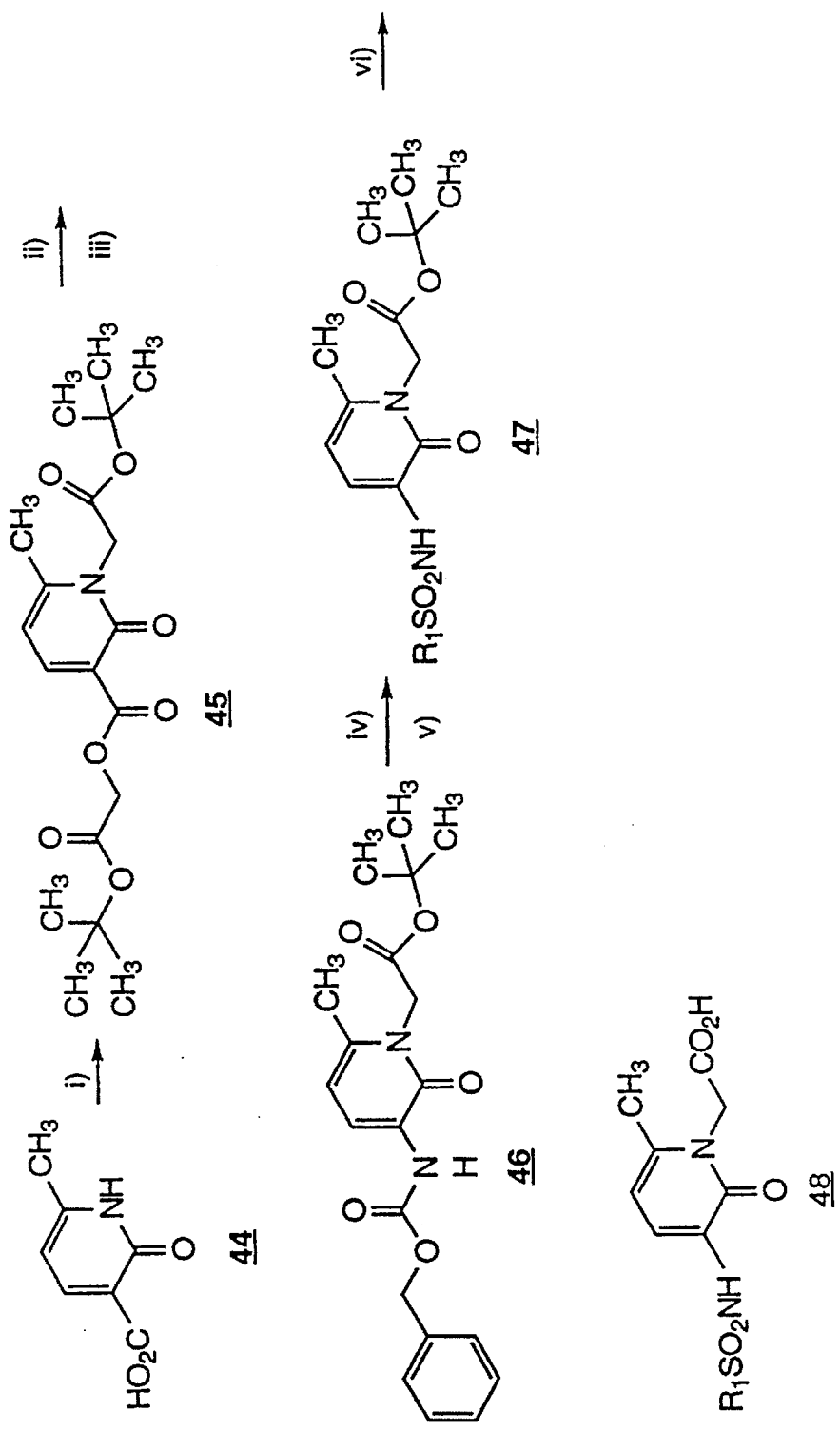
FIG. 8 depicts a reaction scheme for the preparation of certain compounds of the present invention. In this Figure, i) through vi) are: i) $K_2CO_3$, DMF and $BrCH_2CO_2t$-Bu; ii) LiOH and THF; iii) $Et_3N$, DPPA, dioxane and $\Delta$; BnOH and $\Delta$; iv) $H_2$ and Pd/C; v) $R_1SO_2Cl$ and collidine; and vi) TFA; See also Examples 91–96. $R_1$ is as defined herein.

FIG. 8 provides an alternate reaction scheme for preparing the intermediate compound described in Example 16. Examples 91–96 describe this alternate synthetic route.

Figure 11:
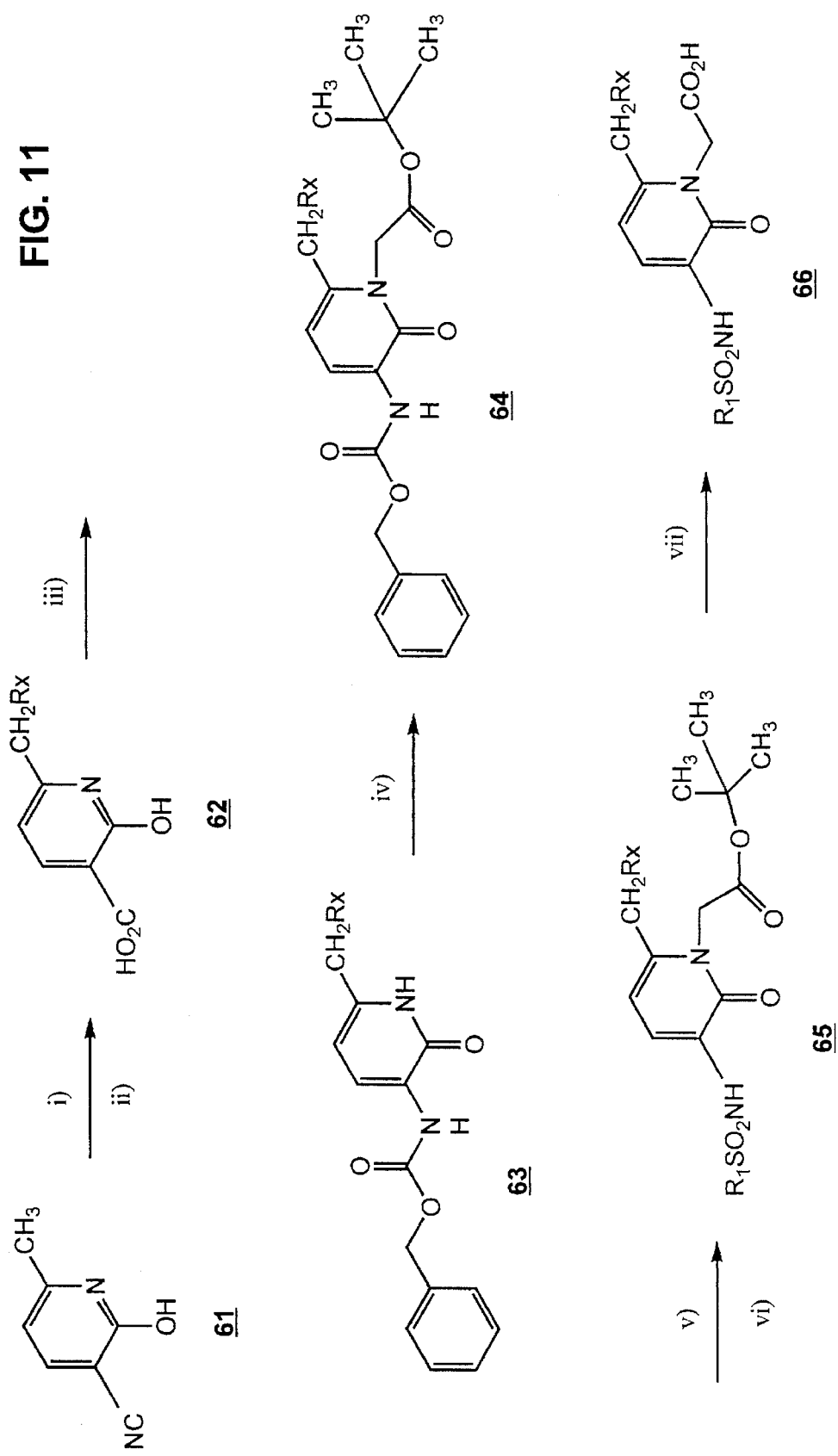
FIG. 11 depicts a reaction scheme for the preparation of certain compounds of the present invention. In this Figure, i) through vii) are: I) 2 equivalents, LDA, $R_8X$, 50% $H_2SO_4$; iii) $Et_3N$, DDPA, dioxane and $\Delta$; BnOH and $\Delta$; iv) NaH, DMF and $BrCH_2CO_2t$-Bu; v) $H_2$ and Pd/C; vi) $R_1SO_2Cl$ and collidine; and vii) TFA. See also Examples 97–101. $R_1$ is as defined herein. $R_x$ is any $R_1$ substituent minus one carbon, such as methyl.

FIG. 11 provides a preferred reaction scheme for the preparation of 6-substituted pyridones. Examples 97–101 describe this synthetic route.

Figure 12:
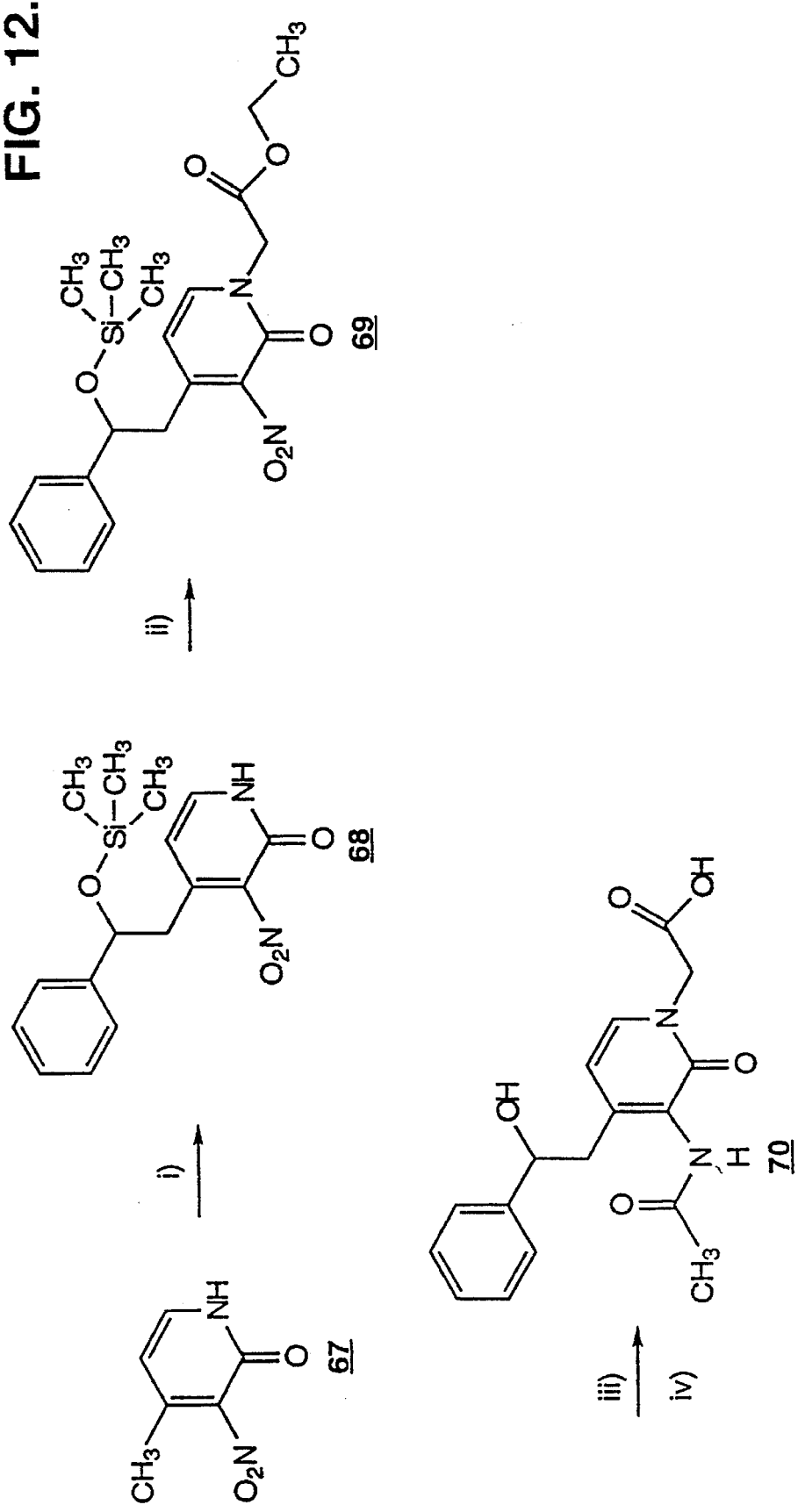
FIG. 12 depicts a reaction scheme for the preparation of certain compounds of the present invention. In this Figure, i) through iv) are $LiN(TMS)_2$, TMSCl, $LiN(TMS)_2$ and benzaldehyde; ii) $LiN(TMS)_2$ and ethyl bromoacetate; iii) $Ac_2O$, 10% Pd/C, $H_2$, iv) LiOH. See also Examples 113–115. $R_9$ is any $R_1$ substituent minus two carbons, such as, a phenyl group.

FIG. 12 provides a preferred reaction scheme for the preparation of 4-(hydroxyl substituted)alkyl or aralkyl pyridones. Examples 113–115 describe this synthetic route.

3. Selection of Preferred Compounds

The compounds of the present invention are screened for their ability to inhibit thrombin, plasmin, recombinant tissue plasminogen activator (rt-PA), activated protein C (aPC), chymotrypsin, and trypsin as set forth below. Certain of the preferred compounds are distinguished by their ability to inhibit thrombin, while not substantially inhibiting plasmin, t-PA, aPC, chymotrypsin, and trypsin. With respect to thrombin and the other enzymes and as used herein, the term "not substantially inhibiting" means that the IC$_{50}$ (or K$_i$) for plasmin, t-PA, aPC, chymotrypsin, and trypsin for a given compound is greater than or equal to its IC$_{50}$ (or K$_i$, respectively) for thrombin.

The compounds of the present invention are dissolved in buffer to give solutions containing concentrations such that assay concentrations range from 0 to 100 micromolar. In the assays for thrombin, plasmin, t-PA, aPC, chymotrypsin, and trypsin, a chromogenic synthetic substrate is added to a solution containing test compound and the enzyme of interest, and the residual catalytic activity of that enzyme is determined spectrophometrically. The $IC_{50}$ of a compound of the present invention is determined from the rate of substrate turnover caused by the specific enzyme being measured. $IC_{50}$ is that concentration of test compound giving 50% inhibition of the rate of substrate turnover. Likewise, the $K_i$ of a compound of the present invention is determined from the rule of substrate turnover caused by the specific enzyme being measured at various enzyme concentrations. $K_i$ is that concentration of test compound giving 50% inhibition of the rate of substrate turnover. Examples A and B provide an exemplar of the in vitro assays used to select the compounds of the present invention.

Certain of the preferred compounds of the present invention have a $K_i$ of about 0.001 to about 200 nM in the thrombin assay. Especially preferred compounds have a $K_i$ of about 0.001 to about 50 nM. The more especially preferred compounds have a $K_i$ of about 0.001 to about 10 nM.

Certain of the preferred compounds of the present invention have a $IC_{50}$ for plasmin, t-PA, aPC, chymotrypsin, and trypsin which is at least 10 times greater than its $IC_{50}$ for thrombin. Especially preferred compounds have an $IC_{50}$ for plasmin, rt-PA, aPC, chymotrypsin, and trypsin which is about 20 to about 100,000 times greater than its $IC_{50}$ for thrombin. More especially preferred compounds have an $IC_{50}$ for plasmin, rt-PA, aPC, chymotrypsin, and trypsin which is about 100 to about 1,000,000 times greater than its $IC_{50}$ for thrombin. In the event that a compound of the present invention has an $IC_{50}$ with respect to plasmin, rt-PA, aPC, chymotrypsin, or trypsin which is greater than the highest concentration of compound tested, the $IC_{50}$ is taken to be that highest concentration of compound.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

The therapeutically effective amount of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixers for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

5. Utility and Methods

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vaccum therein as a means to draw blood obtained by venipuncture into the tube is well known in the medical arts. Kasten, B. L., "Specimen Collection", *Laboratory Test Handbook*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of thrombin, and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as a pharmaceutical agent for preventing thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets capsules or elixers taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a "therapeutically effective amount" of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Preparation of N-alpha-t-butoxycarbonl-$N^g$-nitro-L-arginine lactam.

N-alpha-t-butoxycarbonyl-$N^g$-nitroarginine (2.00 g, 6.3 mmole) was dissolved in tetrahydrofuran (100 mL) by heating the solution to 50° C. The solution was allowed to cool to room temperature. N-methyl piperidine (0.84 mL, 6.9 mmole) was added, and the solution was cooled in an ice bath. Isobutylchloroformate (0.83 mL, 6.3 mmole) was added, and the reaction mixture was stirred at 0° C. for 6 hours. The reaction mixture was stirred for 18 hours while the ice in the Dewar was allowed to melt overnight. The solvent was removed under vacuum. The crude product was dissolved in 20% ethyl acetate/dichloromethane (10 mL), and was purified by flash chromatography through a 3×5 cm column of silica gel using 20% ethyl acetate/dichloromethane as eluent. 125 mL of eluent was collected. The solvent was removed under vacuum to afford 1.39 g (74% crude yield) of the title compound as a white foam. $R_f$=0.44 (silica gel, 5% isopropanol in dichloromethane). Isobutanol was present as an impurity. This compound may be further purified by recrystallization from dichloromethane/hexanes or ethanol/water.

Example 2

Preparation of N-alpha-t-butoxycarbonyl-$N^g$-nitro-L-argininal.

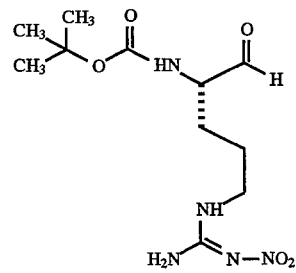

(a) Procedure 1.

To a stirred solution of $LiAlH_4$ in tetrahydrofuran (3.8 mL of a 1.0M solution, 3.8 mmole), cooled in an ice bath, was added dropwise ethyl acetate (0.43 mL, 3.8 mmole) in tetrahydrofuran (5 mL). The solution was stirred for 30 minutes at 0° C. to preform LiAlH$_2$(OEt)$_2$.

The solution of this LiAlH$_2$(OEt)$_2$ was added dropwise to a stirred solution of compound of Example 1 (0.92 g, 3.1 mmole) in tetrahydrofuran (5 mL). After 30 minutes, the reaction is quenched with 1.0N HCl/tetrahydrofuran (2 mL of a 1:1 mixture). 1.0N HCl (20 mL) was added, and the solution was extracted three times with ethyl acetate (20 mL each). The combined organic layers were washed with water (5 mL), saturated sodium bicarbonate (5 mL) and twice with brine (5 mL each), dried over anhydrous magnesium sulfate, filtered and the solvent was removed under vacuum to give 0.94 g (100% yield) of the title compound as an off-white solid.

(b) Procedure 2.

Alternatively, the title compound was made by the procedures which follow.

A 12 liter four-necked round bottom flask equipped with an overhead stirring apparatus was flame dried under a strong stream of nitrogen. After the flask had cooled, 120.0 g of N-alpha-t-butoxycarbonyl-N$^g$-nitro-L-arginine (376 mmole, 1 equivalent) was added under a blanket of nitrogen followed by the addition of 6 liters of anhydrous tetrahydrofuran (Aldrich sure-seal) via canula. The flask was then fitted with a thermometer and the resulting suspension was warmed to 50° C. with a heat gun while stirring. The reaction mixture was cooled to 5° C. with an ice bath and further cooled to −5° C. with an ice/acetone bath.

During the time it took for this solution to reach −5° C., 36.66 g of N-methyl-O-methylhydroxyamine hydrochloride (376 mmole, 1.0 equivalent) was weighed out in a 500 mL flask and suspended in 300 mL of dichloromethane. This suspension was sparged with nitrogen for 5 minutes, cooled to 0° C. and 46 mL of N-methylpiperidine (1.0 equivalent) was added via syringe under nitrogen. The mixture was sonicated briefly to insure complete dissolution/free base formation and recooled to 0° C. in an ice bath while still under nitrogen. The resulting solution of free base was used later.

When the above arginine solution had reached −5° C., 45 mL of N-methylpiperidine was added via syringe followed 5 minutes later by the addition of 46 mL of isobutyl chloroformate (0.95 equivalent) via syringe. The resulting solution was stirred for 15 minutes at −5° C. After this time, the free base solution of N-methyl-O-methyl hydroxylamine generated above was added via canula over about 15 minutes. Stirring was continued at −5° C. for another 1.5 hours at which time thin layer chromatography (silica gel, 1:10:90 acetic acid/methanol/dichloromethane) indicated that the reaction was complete. The reaction mixture was filtered while still cold, the salts washed with 400 mL of cold tetrahydrofuran and the filtrate concentrated under vacuum on a rotary evaporator to yield a yellow foam.

The crude intermediate was taken up in 300 mL of dichloromethane and applied to a column of silica gel (70–230 mesh, 7×50 cm). The column was first eluted with 2 liters of dichloromethane followed by 2 liters of 2% methanol in dichloromethane. This was followed by elution with 5% methanol in dichloromethane until all of the product had been eluted (the eluant was checked for UV activity and five one-liter fractions were collected once this UV activity was apparent). Fractions containing pure product were pooled and concentrated under vacuum and pumped on overnight to yield 120.1 g (88% yield) of N-alpha-t-butoxycarbonyl-N$^g$-nitro-L-arginine-(N-methyl, N-methoxyamide) as light yellow foam. This foam was taken up in 300 mL of dichloromethane, 300 mL of toluene, and the volatiles were once again removed under vacuum to remove any residual water or methanol.

120.1 g of N-alpha-t-butoxycarbonyl-N$^g$-nitro-L-arginine-(N-methyl, N-methoxyamide) (331.4 mmole) was taken up in 2.8 liters of dry (Aldrich sure-seal) tetrahydrofuran and transferred to a dry 5 liter 4-necked round bottom flask equipped with a mechanical stirrer and a low temperature thermometer. The solution was cooled to −70° C. with a dry ice/acetone bath and 300 mL of 1M LiAlH$_4$ in tetrahydrofuran was added by canula transfer directly from 100 mL Aldrich sure-seal bottles. An additional 50 mL of 1M LiAlH$_4$ in tetrahydrofuran was added via syringe (total 331 mL). During the additions, the reaction temperature was kept below −60° C. The reaction was stirred for 0.5 hours at −70° C., the cooling bath removed, and the reaction was slowly allowed to warm to 0° C. (about 2.5 hours). Between −30° C. and −20° C. a thick slurry resulted. When the reaction mixture obtained 0° C., a small aliquot was removed and partitioned between ethyl acetate/2M potassium bisulfate. The organic layer was analyzed by thin layer chromatography (silica gel, ethyl acetate).

When the reaction was judged to be complete, it was cooled to −70° C. and 503 mL of 2M potassium bisulfate was added via dropping funnel at a slow enough rate to keep the reaction temperature below −30° C. The cooling bath was removed and the reaction mixture was allowed to come to 0° C. over the course of 2 hours at which time a white precipitate was filtered off. The solids were washed with 500 mL of cold tetrahydrofuran. The filtrate was concentrated under vacuum on a rotary evaporator until most of the tetrahydrofuran was removed and the remaining white sludge was mostly aqueous. The crude product was taken up in 1.5 liters of ethyl acetate and washed with 0.2M HCl (2×200 mL). The HCl extracts were back-extracted with 400 mL of ethyl acetate and the organics were combined and extracted with saturated sodium bicarbonate (2×200 mL). The bicarbonate extracts were also back-extracted with 400 ml of ethyl acetate. The organics were then combined and washed with brine (200 mL) followed by drying over anhydrous sodium sulfate. The solution was filtered, concentrated under vacuum on a rotary evaporator and pumped on overnight to yield a white solid (89.0 g) of crude title compound. This was chromatographed on silica gel and eluted with a gradient of 0 to 10% methanol in dichloromethane. The pure fractions were combined and evaporated to yield the title compound as a white solid (75 g, 74%).

Example 3

Preparation of N-alpha-t-butoxycarbonyl-N$^g$-nitro-L-argininal ethyl cyclol

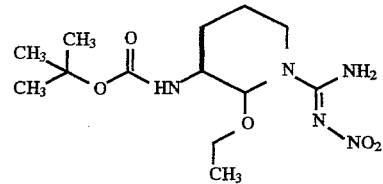

The compound of Example 2 (41.60 g, 0.137 mole) was dissolved in ethanol (200 mL) and concentrated HCl (1 mL) was added. After the reaction was complete by TLC (silica gel, 10% methanol in dichloromethane), the solvent was removed under vacuum. The crude product was purified by flash chromatography through a column of silica gel (230–400 mesh) using 0–10% ethyl acetate/ dichloromethane as eluent. The combined fractions yielded 36.88 g (81%) of the title compound as pale yellow foam. $R_f$=0.62 (silica gel, 5% methanol in dichloromethane).

Example 4

Preparation of $N^g$-nitro-L-argininal ethyl cyclol, hydrochloride salt

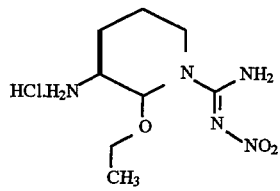

To a solution of the compound of Example 3 (35 g) in 500 mL of absolute ethanol at 0° C. was added slowly 500 mL of absolute ethanol saturated with HCl(g). This mixture was allowed to warm to 25° C. and checked by thin-layer chromatography. The appearance of a very polar product was the desired compound. Most of the HCl was removed with a stream of dry nitrogen and the resulting organic solvent was removed under vacuum. The resulting 33 g of the title compound as a yellow-white solid was used without further purification.

Example 5

Preparation of ethyl(3-nitro-2-oxo-1,2-dihydropyridyl)acetate

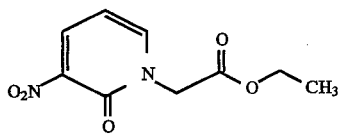

Sodium hydride (4.08 g of a 60% dispersion in mineral oil, 0.10 mole) was washed with hexanes three times (10 mL each) and suspended in dimethylformamide (50 mL). The stirred suspension was cooled in an ice bath, then 3-nitro-2-hydroxypyridine (13.0 g, 0.093 mole) was added in small portions over a 45-minute period. After the addition was complete, the reaction was stirred at 0° C. for 10 minutes, then room temperature for 30 minutes. The reaction mixture was recooled in an ice bath. Ethyl bromoacetate (0.75 mL, 0.097 mole) was added. The reaction was stirred at 0° C. for 1 hour, then 1.5 hours at room temperature. The reaction mixture was partitioned between ethyl acetate (200 mL) and water(200 mL). The aqueous layer was extracted with ethyl acetate (3×200 mL). The combined organic extracts were washed with water (4×100 mL), brine, and dried over anhydrous sodium sulfate. The solvent was removed under reduced pressure. The residue was chromatographed through silica gel using 0–20% ethyl acetate/ dichloromethane as eluent to afford 15.7 g (75% yield) of the title compound as yellow solid. $R_f$=0.30 (silica gel, 20% ethyl acetate in dichloromethane).

Example 6

Preparation of ethyl(3-[(benzylsulfonyl)amino]-2-oxo-1,2-dihydropyridyl)acetate

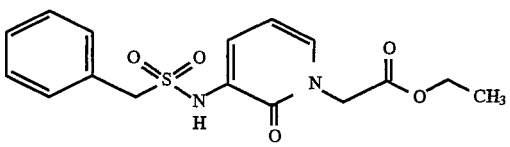

A stirred solution of the compound of Example 5 (44.5 g, 0.197 mole) in ethanol (200 mL) was hydrogenated over 10% Pd/C (2.25 g) for 16 hours under balloon pressure. Celite was added, and the reaction mixture was filtered through a pad of celite in a 600 mL fritted funnel (5 cm depth), using ethyl acetate to wash. The solvent was removed under vacuum, diluted with ethyl acetate (200 mL) and toluene (200 mL), and the solvent was removed under vacuum to give crude ethyl(3-amino-2-oxo-1,2-dihydropyridyl)acetate (40.0 g, 0.204 mole) in quantitative yield.

A stirred solution of ethyl(3-amino-2-oxo-1,2-dihydropyridyl)acetate (40.0 g, 0.204 mole) and 2,4,6-collidine (54 mL, 0.408 mole) in tetrahydrofuran (200 mL) was cooled in an ice bath. A solution of benzylsulfonyl chloride (38.9 g, 0.204 mmole) in tetrahydrofuran (200 mL) was added over a 50-minute period. After addition was complete, the solution was stirred for 30 minutes at 0° C. The reaction mixture was diluted with ethyl acetate (1.2 L), washed with 1.0N HCl (until aqueous layer is pH 1), water (50 mL), saturated sodium bicarbonate (100 mL), and brine (2×50 mL). The organic layer was dried over anhydrous magnesium sulfate, and the solvent was removed. The residue was recrystallized from chloroform. 39 g of the title compound was isolated. To the mother liquor was added silica gel. The solution was swirled, then filtered through a sintered glass funnel, washing with 50% ethyl acetate in dichloromethane. The solvent was removed from the filtrate, and the residue was recrystallized from chloroform. An additional 13 g of the title compound was isolated to afford a total of 52.00 g (75% yield) of the title compound as a tan solid. $R_f$=0.32 (silica gel, 20% ethyl acetate in dichloromethane). m.p. 48°–49° C.

Example 7

Preparation of [3-[(benzylsulfonyl)amino]-2-oxo-1,2-dihydropyridyl]acetic acid

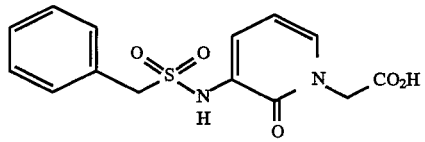

To a cooled (0° C.) suspension of the compound of Example 6 (50.89 g, 0.145 mole) in methanol (500 mL) was added 1.0N NaOH (327 mL) over a period of 10 minutes. After the addition was complete, the solution was allowed to warm to room temperature over a period of 1.5 hours. The solution became homogeneous upon addition of NaOH. A precipitate formed during the reaction. The solvent was reduced under vacuum, the residue diluted with water (400 mL), and washed with ethyl acetate (2×150 mL). The aqueous layer was acidified with 2.0N HCl to pH 1, and extracted with ethyl acetate (3×200 mL). The combined organic extracts were washed with water, then brine (twice). The product crystallized. The 2 combined crops yielded 44.54 g (95%) of the title compound as off white crystals.

$R_f$=0.17 (silica gel, 1% acetic acid, 10% methanol in dichloromethane). m.p. 186°–187° C.

Example 8

Preparation of [3-[(benzylsulfonyl)amino]-2-oxo-1, 2-dihydropyridyl]acetyl-$N^g$-nitro-L-argininal ethyl cyclol

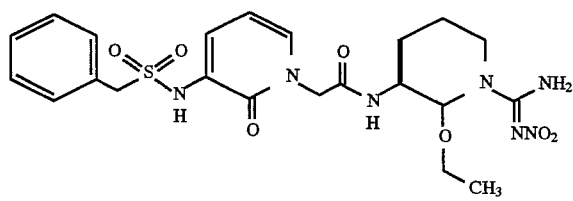

To a stirred suspension of the compound of Example 7 (23.3 g, 77 mmole), the compound of Example 4 ($N^g$-nitro-L-argininal ethyl cyclol, hydrochloride salt, 24.76 g, 92 mmole), and N-hydroxybenzotriazole (11.79 g, 77 mmole) in acetonitrile (400 mL) cooled to 0° C. was added 1-ethyl-3-(3-dimethylamino-propyl)carbodiimide hydrochloride salt (EDC, 17.76 g, 92 mmole). After 30 minutes, the solution was almost homogeneous. N-methylmorpholine (25.4 mL, 231 mmole) was added dropwise. After the addition was complete, the reaction was stirred at room temperature for 3 hours. The solvent was reduced under vacuum, and the resulting residue was dissolved in dichloromethane (600 mL), washed with 50 mL each of 2.0N HCl (to pH 1), water, saturated sodium bicarbonate and brine. The extract was dried over anhydrous magnesium sulfate, and the solvent was removed under vacuum. The crude product was purified in three batches using a 600 mL fritted funnel as a column through silica gel (7 cm depth) to yield (29.40 g, 74%) of the title compound. Analytical HPLC gave $t_R$=12.8 minutes (20–60% $CH_3CN$, 25 mm Vydac C-18 column). $R_f$=0.28 (silica gel, 5% ethanol in dichloromethane).

Example 9

Preparation of [3-[(benzylsulfonyl)amino]-2-oxo-1, 2-dihydropyridyl]acetyl-L-argininal ethyl cyclol, acetate salt

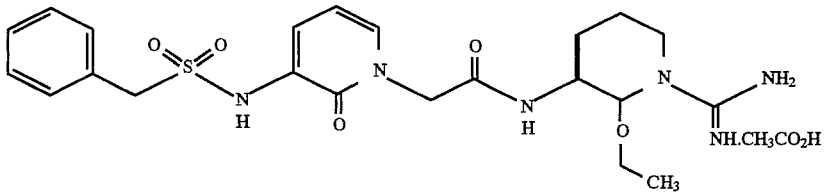

The compound of Example 8 (5.60 g, 11 mmole) in ethanol/acetic acid/water (4:1:1, 60 mL) was hydrogenated over 10% palladium on carbon (1.80 g) for 4 hours at 20 psi. Celite was added, and the solution was filtered through a 0.2 micron filter, washing the solid with ethanol/acetic acid/water (4:1:1, 60 mL). To the filtrate was added 10% palladium on carbon (1.80 g), and the solution was hydrogenated at 20–25 psi for 40 hours. Celite was added, and the solution was filtered through a 0.2 micron filter, washing the solid with water (200 mL). The solvent was reduced to a volume of 200 mL under reduced pressure, then washed with ethyl acetate (50 mL). The solvent from the aqueous layer was reduced to remove the volatiles, then the aqueous layer was lyophilized to yield 4.88 g (85% yield) of the title compound. Analytical HPLC gave $t_R$=9.5 minutes (20–60% $CH_3CN$, 25 mm Vydac C-18 column).

Example 10

Preparation of [3-[(benzylsulfonyl)amino]-2-oxo-1, 2-dihydropyridyl]acetyl-L-argininal, trifluoroacetate salt

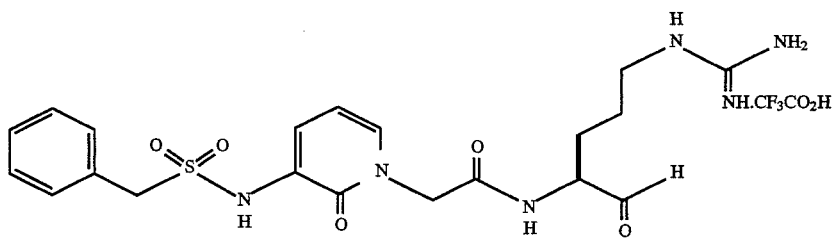

The compound of Example 9 (4.88 g, 9.2 mmole) was suspended in 3.0N HCl (100 mL). After stirring for 3 h, the reaction mixture was quenched with 2.5M aqueous sodium acetate to pH 3.5–4, then filtered through a 2 micron filter. The filtrate was purified in two batches by preparative HPLC (Waters PrepPak cartridge, Delta-Pak C18, 300 angstrom column, 0–40% acetonitrile/water containing 0.1% trifluoroacetic acid). The clean fractions were combined to give 2.05 g (40% yield) of the title compound. Fast atom bombardment mass spectrometry confirmed the theoretical molecular weight of 463.

Example 11

6-methylpyrid-2-one-3-carbonitrile

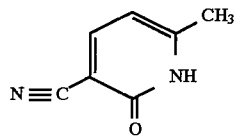

To stirred a mixture of sodium methoxide (46.5 g, 860 mmole) in diethyl ether (950 mL), cooled in an ice bath, was added a mixture of acetone (46.5 g, 800 mmole) and ethyl formate (59.6 g, 800 mmole) dropwise over 1 hour. When addition was complete, the cooling bath was removed and the mixture was warmed to room temperature over a 1 hour period. The volatile materials were distilled, keeping the oil bath at no more than 60° C. To the solid residue was added cyanoacetamide (67 g, 800 mmole) in water (400 mL) and piperidine acetate (140 mmole, prepared by adding piperidine to a solution of 8.0 mL of acetic acid in 20 mL water until the solution was greater than pH 7). The flask was fitted with a reflux condenser, and the mixture was heated for 2 hours under reflux. The mixture was cooled to room temperature and acidified to pH 5 with acetic acid. After standing overnight at room temperature, the mixture was cooled in an ice bath for 45 minutes. The yellow solid product was filtered, washed with ice water four times and dried under vacuum at 80° C. overnight. Crystallization from 50% (v/v) ethanol afforded the title compound as a yellow solid (52.6 g, 49% yield). $R_f$=0.29 (silica gel, 95:5 chloroform:methanol). Fast atom bombardment mass spectrometry confirmed the theoretical molecular weight of 134.

Example 12

6-methylpyrid-2-one-3-carboxylic acid

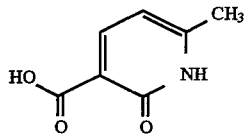

A suspension of the compound of example 11 (16.9 g) in 20% NaOH (w/w, 63 mL) was heated at 140°–145° C. overnight in a sealed bomb. The cooled reaction mixture was acidified to about pH 8 with concentrated hydrochloric acid and extracted with dichloromethane (three times). The aqueous phase was acidified, precipitating a yellow solid which was filtered, washed with water, and dried overnight in a vacuum oven at approximately 80° C. The dried title compound (15.68 g, 81% yield) required no further purification. Fast atom bombardment mass spectrometry confirmed the theoretical molecular weight of 153.

Example 13

Preparation of 3-benzyloxycarbonylamino-6-methylpyrid-2-one

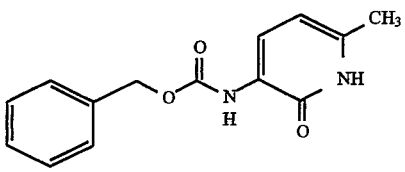

To the compound of Example 12 (11.8 g, 0.077 mole), suspended in dioxane (260 mL), triethylamine (11.3 mL, 0.081 mole) is added dropwise rapidly with stirring followed by diphenylphosphoryl azide (16.7 mL, 0.077 mole). The suspension is heated under reflux for 4 hours using a preheated 120° C. oil bath. Benzyl alcohol (24.1 mL, 0.23 mole) is then added and the mixture was stirred under reflux overnight. The reaction mixture is cooled and evaporated. The residue is suspended in water (600 mL) and filtered. The filter cake is washed with 10% HCl twice, saturated sodium bicarbonate and brine. The crude product is chromatographed using 20–30% ethyl acetate/chloroform to give the title compound.

Example 14

Preparation of ethyl(3-benzyloxycarbonylamino-6-methyl-2-oxo-1,2-dihydro-1-pyridyl)acetate

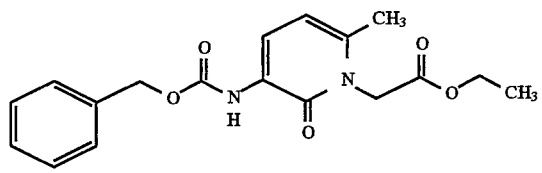

The compound of Example 13 (1.80 g, 7.0 mmole) was added to a stirred suspension of sodium hydride (0.33 g, 8.4 mmole) in dry dimethylformamide (50 mL). After 45 minutes, ethyl iodoacetate (1.43 g, 6.7 mmole) was added, and the mixture was stirred overnight, diluted with 10% hydrochloric acid (300 mL) and extracted with ethyl acetate (3×150 mL). The organic layer was washed with brine (twice), dried and evaporated. The resulting yellow, waxy solid was chromatographed, eluting with 3% ethyl acetate in dichloromethane, to give the title compound (1.28 g, 53% yield). $R_f$=0.52 (silica gel, 5:95 methanol:dichloromethane). Fast atom bombardment mass spectrometry confirmed the theoretical molecular weight of 344.

Example 15

Preparation of ethyl[3-[(benzylsulfonyl)amino]-6-methyl-2-oxo-1,2-dihydromyridyl]acetate

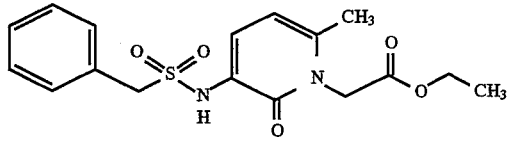

A stirred solution of compound of Example 14 (2.50 g) in ethanol (25 mL) is hydrogenated over 10% Pd/C (0.25 g) for 5 hours under balloon pressure. Celite is added, and the reaction mixture is filtered through a pad of celite, using ethyl acetate to wash. The solvent is removed under vacuum, diluted with ethyl acetate (20 mL) and toluene (20 mL), and the solvent is removed under vacuum to give crude ethyl (3-amino-6-methyl-2-oxo-1,2-dihydropyridyl)acetate.

A stirred solution of ethyl(3-amino-6-methyl-2-oxo-1,2-dihydropyridyl)acetate (0.55 g, 2.6 mmole) and 2,4,6-collidine (1.2 mL, 5.2 mmole) in tetrahydrofuran (10 mL) is cooled in an ice bath. A solution of benzylsulfonyl chloride (0.50 g, 2.6 mmole) in tetrahydrofuran (10 mL) is added over a 15 minute period. After addition is complete, the solution is stirred for 30 minutes at 0° C. The reaction mixture is diluted with ethyl acetate (100 mL), washed with 1.0N HCl (until aqueous layer is pH 1), water (10 mL), saturated sodium bicarbonate (10 mL), and brine (2×10 mL). The organic layer is dried over anhydrous magnesium sulfate, and the solvent is removed. The residue is chromatographed through silica gel using 0:100–20:80 ethyl acetate:dichloromethane as eluent to afford the title compound.

Example 16

Preparation of [3-[(benzylsulfonyl)amino]-6-methyl-2-oxo-1,2-dihydropyridyl]acetic acid

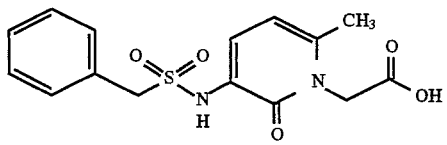

Using similar procedures to that described above in Example 7, the title compound is prepared from the compound of Example 15. An alternative method of preparing the title compound is described in Examples 91–96.

Example 17

Preparation of [3-[(benzylsulfonyl)amino]-6-methyl-2-oxo-1,2-dihydropyridyl]acetyl-N$^g$-nitro-L-argininal ethyl cyclol

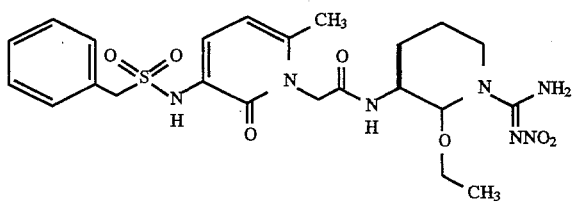

Using similar procedures to that described above in Example 8, the title compound is prepared from the compound of Example 16.

Example 18

Preparation of [3-[(benzylsulfonyl)amino]-6-methyl-2-oxo-1,2-dihydropyridyl]acetyl-L-argininal ethyl cyclol, acetate salt

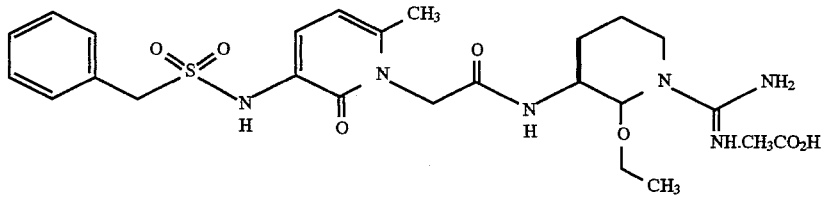

Using similar procedures to that described above in Example 9, the title compound is prepared from the compound of Example 17.

Example 19

Preparation of [3-[(benzylsulfonyl)amino]-6-methyl-2-oxo-1,2-dihydropyridyl]acetyl-L-arqininal, trifluoroacetate salt

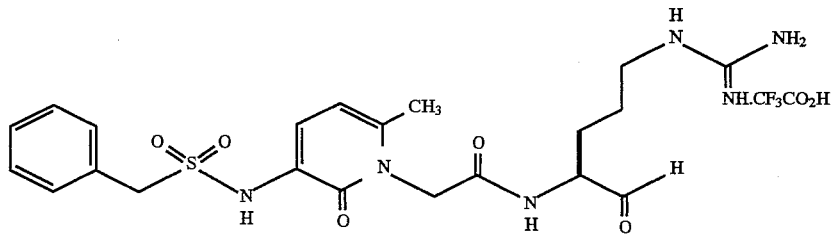

Using similar procedures to that described above in Example 10, the title compound is prepared from the compound of Example 18.

Example 20

Preparation of ethyl pyrimidin-6(1H)-one-5-carboxylate

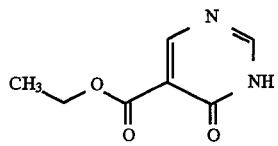

Diethyl ethoxymethylenemalonate (10.1 mL, 50 mmole) and formamidine acetate (10.4 g, 100 mmole) were refluxed in ethanol (10 mL) for 24 hours. The reaction mixture was allowed to cool to room temperature overnight, and suspended in ethyl acetate (30 mL) and 1.0N HCl (20 mL). The suspension was filtered, and the filter cake was washed with 1.0N HCl, followed by water, then ethyl acetate, and air dried affording the title compound as an tan solid (3.33 g, 40% yield). $R_f$=0.21 (silica gel, 10% methanol in dichloromethane). m.p. 187°–188° C.

Example 21

Preparation of ethyl 1-allyl-pyrimidin-6(1H)-one-5-carboxylate

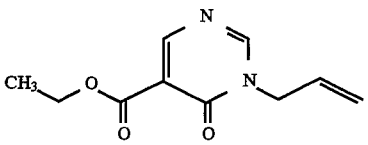

The compound of Example 20 (4.3 g, 26 mmole) is added to a stirred suspension of sodium hydride (1.13 g, 28 mmole) in dry dimethylformamide (50 mL). After 45 minutes, allyl bromide (2.21 mL, 26 mmole) is added, and the mixture is stirred overnight, diluted with 10% hydrochloric acid (300 mL) and extracted with ethyl acetate (3×150 mL). The organic layer is washed with brine (twice), dried and evaporated. The residue is chromatographed through silica gel using 0–10% isopropanol/dichloromethane as eluent. The title compound is isolated.

Example 22

Preparation of 1-allyl-pyrimidin-6(1H)-one-5-carboxylic acid

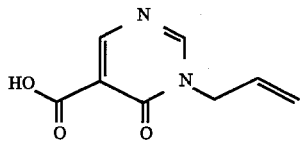

To the compound of Example 21 (5.00 g, 0.024 mole), suspended in methanol (25 mL) and cooled in an ice bath, 1.0N NaOH (29 mL, 0.029 mole) is added dropwise rapidly with stirring. After 16 hours, the solvent is reduced under vacuum, residue diluted with water (50 mL), and washed with ethyl acetate (2×15 mL). The aqueous layer is acidified with 2.0N HCl to pH 1, extracted with ethyl acetate (3×50 mL). The combined organic extracts are washed with water, then brine (twice). The solvent is removed in vacuo to afford the title compound.

Example 23

Preparation of 1-allyl-5-t-butyloxycarbonylamino-6-oxo-1-pyrimidi-6(1H)-one

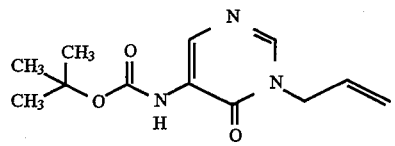

To the compound of Example 22 (10.0 g, 0.056 mole), suspended in dioxane (260 mL), triethylamine (8.1 mL, 0.058 mole) is added dropwise rapidly with stirring followed by diphenylphosphoryl azide (12.0 mL, 0.077 mole). The suspension is heated under reflux for 4 hours using a preheated 120° C. oil bath. t-Butanol (12.3 g, 0.17 mole) is then added and the mixture is stirred under reflux overnight. The reaction mixture is cooled and evaporated. The residue is suspended in water (600 mL) and filtered. The filter cake is washed with 1.0N HCl twice, saturated sodium bicarbonate and brine. The crude product is chromatographed using 0–50% ethyl acetate/dichloromethane to give the title compound.

Example 24

Preparation of 1-allyl-5-amino-6-oxo-1-pyrimidi-6(1H)-one, trifluoroacetate salt

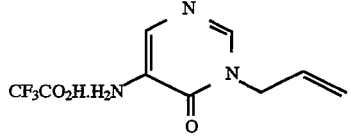

The compound of Example 23 (5.00 g) is treated with 50% trifluoroacetic acid in dichloromethane (50 mL) for 35 minutes. The solution is added dropwise to diethyl ether (500 mL), while swirling. The precipitate is filtered, washing with diethyl ether. The powder is dried under vacuum to yield the title compound.

Example 25

Preparation of 1-allyl-5-benzylsulfonylamino-6-oxo-1-pyrimidi-6(1H)-one

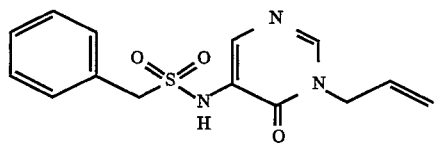

The free base of the compound of Example 24 is generated by dissolving the compound of Example 24 (5.00 g, 18.9 mmole) in 1M potassium carbonate. The free base is then extracted into dichloromethane, which is dried and evaporated to give 1-allyl-5-amino-6-oxo-1-pyrimidi-6(1H)-one.

A stirred solution of 1-allyl-5-amino-6-oxo-1-pyrimidi-6 (1H)-one and 2,4,6-collidine (8.3 mL, 38 mmole) in tetrahydrofuran (25 mL) is cooled in an ice bath. A solution of benzylsulfonyl chloride (3.59 g, 18.9 mmole) in tetrahydrofuran (25 mL) is added over a 15-minute period. After addition is complete, the solution is stirred for 1 hour at 0° C. The reaction mixture is diluted with ethyl acetate (200 mL), washed with 1.0N HCl (until aqueous layer is pH 1), water (25 mL), saturated sodium bicarbonate (25 mL), and brine (2×25 mL). The organic layer is dried over anhydrous magnesium sulfate and the solvent is removed in vacuo to give the title compound.

Example 26

Preparation of 5-benzylsulfonylamino-6-oxo-1,6-dihydro-1-pyrimidinylacetaldehyde

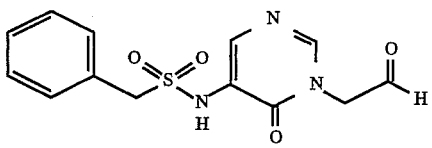

To a solution of the compound of Example 25 (5.00 g, 16.4 mole) in tetrahydrofuran (50 mL) and water (7 mL) is added N-methylmorpholine-N-oxide (3.20 g, 16.4 mmole) and osmium tetroxide (1.0 mL of a 4% solution in water, 0.16 mmole). After the reaction mixture is stirred for 18 hours, N-methylmorpholine-N-oxide (0.47 g, 2.8 mmole) is added. After stirring the reaction mixture for 4 hours, sodium thiosulfate, (2.5 mL of a saturated aqueous solution) and diatomaceous earth (7 g) are added, and the mixture is stirred for 30 minutes. The mixture is filtered and evaporated under vacuum to give an oil. This oil is dissolved in ethanol (60 mL) and a solution of sodium periodate (7.00 g, 33 mmole) in water (10 mL) is added. The residue is dissolved in ethyl acetate and the solution is washed with water, dried, and evaporated to afford the title compound.

Example 27

Preparation of 5-benzylsulfonylamino-6-oxo-1,6-dihydro-1-pyrimidinylacetic acid

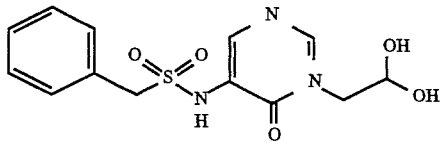

To the compound of Example 26 (5.00 g, 15.6 mmole) in t-butanol (40 mL) and 2-methyl-2-butene (133 mL) is added a solution of sodium chlorite (13 g, 14 mmole) and sodium dihydrogen phosphate monohydrate (15.1 g, 109 mmole) in water (40 mL). The reaction mixture is stirred for 3 hours, then concentrated under reduced pressure. The residue is diluted with ethyl acetate and extracted with 1.0N sodium hydroxide. The aqueous layer is acidified to pH 1 with 1.0N hydrochloric acid, then extracted with dichloromethane twice. The organic extracts are dried and evaporated to give the title compound.

Example 28

Preparation of 5-benzylsulfonylamino-6-oxo-1,6-dihydro-1-pyrimidinylacetyl-$N^g$-nitro-L-argininal ethyl cyclol

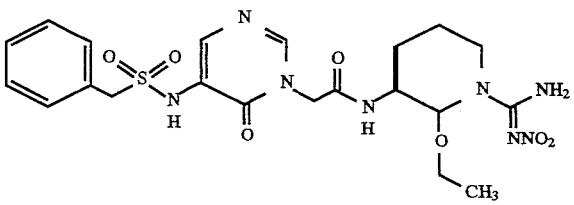

Using similar procedures to that described above in Example 8, the title compound is prepared from the compound of Example 27.

Example 29a

Preparation of 5-benzylsulfonylamino-6-oxo-1,6-dihydro-1-pyrimidinylacetyl-L-argininal ethyl cyclol, acetate salt

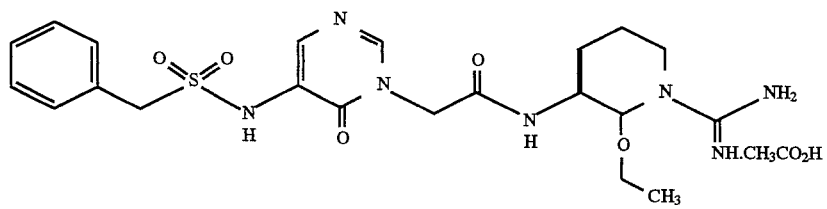

Using similar procedures to that described above in Example 9, the title compound is prepared from the compound of Example 28.

Example 29b

Preparation of 5-benzylsulfonylamino-6-oxo-1,6-dihydro-1-pyrimidinylacetyl-L-argininal, trifluoroacetate salt

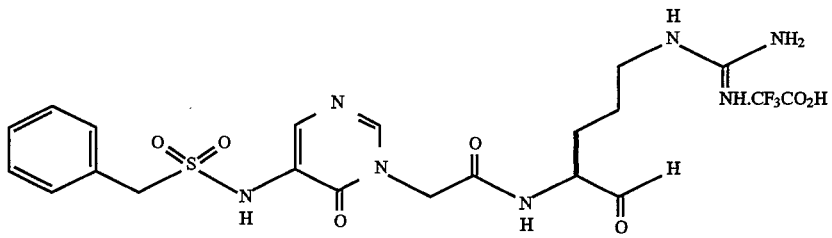

Using similar procedures to that described above in Example 10, the title compound is prepared from the compound of Example 29a.

Example 30

Ethyl 2-methyl-pyrimidin-6(1H)-one-5-carboxylate

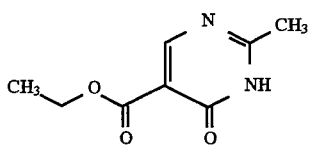

Acetamidine hydrochloride (37.16 g, 0.39 mole) was stirred in sodium ethoxide in ethanol (73 mL of a 21% solution, 0.20 mole) for 5 minutes. Diethyl ethoxymethylenemalonate (31.5 mL, 0.15 mole) was added, and the reaction mixture was refluxed for 5 hours. The reaction mixture was allowed to cool to room temperature overnight, and diluted with dichloromethane (100 mL). The solution was filtered, washing the solid cake with dichloromethane. The filtrate was concentrated at reduced pressure. The residue was dissolved in dichloromethane (150 mL) and 2.0N HCl (30 mL). The pH of the aqueous layer was 1. The organic layer was washed with water, saturated sodium bicarbonate and brine, dried over anhydrous magnesium sulfate, and the solvent was removed under reduced pressure. The residue was dissolved in hot dichloromethane (50 mL). Ethyl acetate was added (50 mL). The product precipitated. The solution was boiled for 5 minutes, cooled to room temperature, and hexanes were added (50 mL). The resulting crystals were filtered, then washed with ethyl acetate (20 mL) followed by hexanes (50 mL) to yield the title compound (7.22 g, 27%) as off-white crystals. $R_f$=0.27 (silica gel, 10% isopropanol in dichloromethane). The title compound also was prepared by the route described in Example 102.

Example 31

Preparation of ethyl 1-allyl-2-methyl-pyrimidin-6(1H)-one-5-carboxylate

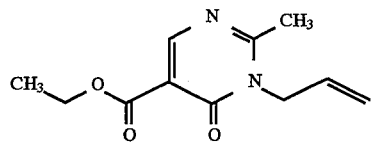

Using similar procedures to that described above in Example 21, the title compound is prepared from the compound of Example 30.

Example 32

Preparation of 1-allyl-2-methyl-pyrimidin-6(1H)-one-5-carboxylic acid

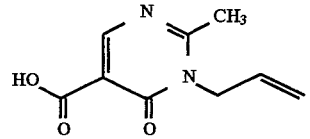

Using similar procedures to that described above in Example 22, the title compound is prepared from the compound of Example 31.

Example 33

Preparation of 1-allyl-2-methyl-5-t-butyloxycarbonylamino-6-oxo-1-pyrimidi-6(1H)-one

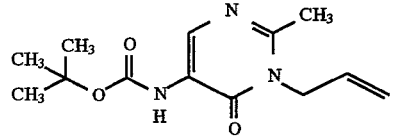

Using similar procedures to that described above in Example 23 the title compound is prepared from the compound of Example 32.

Example 34

Preparation of 1-allyl-2-methyl-5-amino-6-oxo-1-pyrimidi-6(1H)-one, trifluoroacetate salt

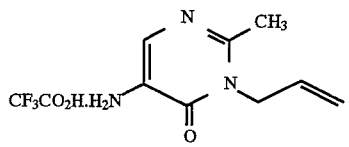

Using similar procedures to that described above in Example 24, the title compound is prepared from the compound of Example 33.

Example 35

Preparation of 1-allyl-2-methyl-5-benzylsulfonylamino-6-oxo-1-pyrimidi-6(1H)-one

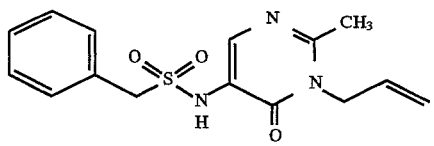

Using similar procedures to that described above in Example 25, the title compound is prepared from the compound of Example 34.

Example 36

Preparation of 5-benzylsulfonylamino-6-oxo-1,6-dihydro-1-pyrimidinylacetaldehyde

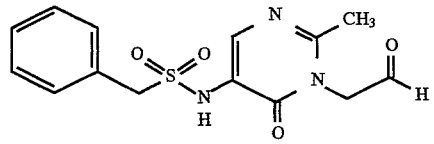

Using similar procedures to that described above in Example 26, the title compound is prepared from the compound of Example 35.

Example 37

Preparation of 5-benzylsulfonylamino-6-oxo-1,6-dihydro-1-pyrimidinylacetic acid

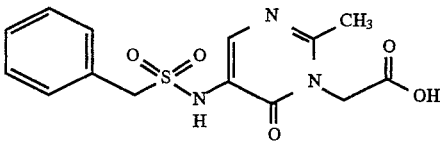

Using similar procedures to that described above in Example 27, the title compound is prepared from the compound of Example 36. An alternative method of preparing the title compound is described in Examples 102–107.

Example 38

Preparation of 2-methyl-5-benzylsulfonylamino-6-oxo-1,6-dihydro-1-pyrimidinylacetyl-$N^g$-nitro-L-argininal ethyl cyclol

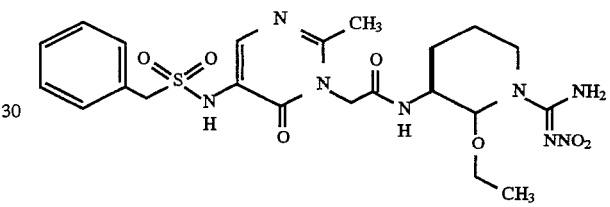

Using similar procedures to that described above in Example 8, the title compound is prepared from the compound of Example 37.

Example 39

Preparation of 2-methyl-5-benzylsulfonylamino-6-oxo-1,6-dihydro-1-pyrimidinylacetyl-L-argininal ethyl cyclol, acetate salt

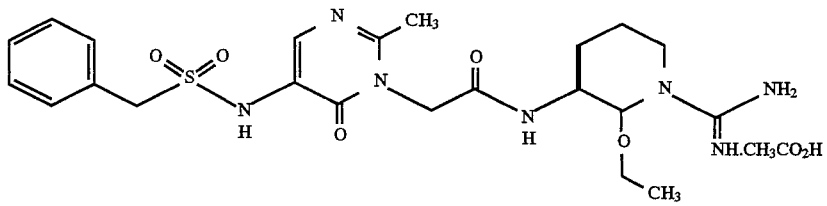

Using similar procedures to that described above in Example 9, the title compound is prepared from the compound of Example 38.

Example 40

Preparation of 2-methyl-5-benzylsulfonylamino-6-oxo-1,6-dihydro-1-pyrimidinylacetyl-L-argininal, trifluoroacetate salt

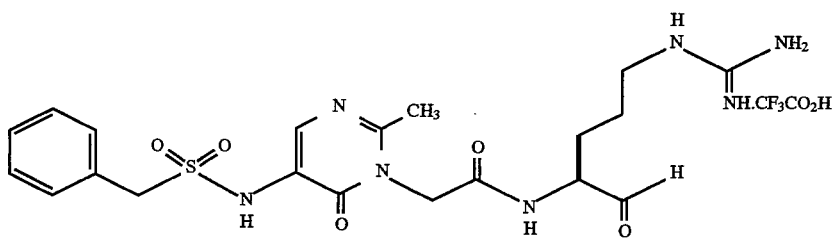

Using similar procedures to that described above in Example 10, the title compound is prepared from the compound of Example 39. An alternative method of preparing the title compound is described in Example 112 (Compound C).

Example 41

Preparation of 5-nitro-1-methoxymethyluracil

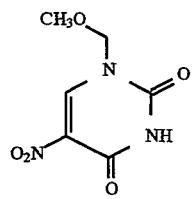

5-nitrouracil (10.00 g, 64 mmole), 1,1,1-3,3,3-hexamethyldisilazane (40 mL, 190 mmole) and chlorotrimethylsilane (4.0 mL, 32 mmole) are heated to reflux for 24 hours. The solution is concentrated under reduced pressure to afford 5-nitrouracil bis(trimethylsilyl) ether. 5-nitrouracil bis(trimethylsilyl) ether (10.0 g, 24 mmole), dimethylformamide (50 mL) and bromomethylmethyl ether (5.9 mL, 73 mmole) are heated in an 80° C. oil bath for 24 hours. Ice water (500 mL) is added, and the mixture is stirred for 30 minutes, then extracted with dichloromethane (3×). The combined organic layers are dried over anhydrous magnesium sulfate, filtered, and concentrated under reduced pressure to give the title compound.

Example 42

Preparation of ethyl 5-nitro-1-methoxymethyl-3-uracilylacetate

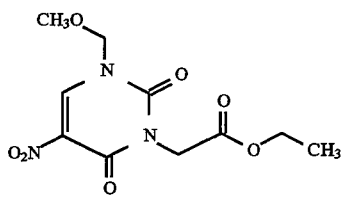

The compound of example 41 (10.0 g, 50 mmole) is dissolved in tetrabutylammonium flouride (120 mL of a 1.0M solution in tetrahydrofuran, 0.124 mole). Ethyl bromoacetate (8.3 mL, 75 mmole) is added. The reaction is stirred at room temperature. The reaction mixture is concentrated, then partitioned between dichloromethane and water. The aqueous layer is extracted with dichloromethane. The combined organic extracts are washed with water, brine, and dried over anhydrous magnesium sulfate. The solvent is removed under vacuum to afford the title compound.

Example 43

Preparation of ethyl 5-benzylsulfonylamino-1-methoxymethyl-3-uracilylacetate

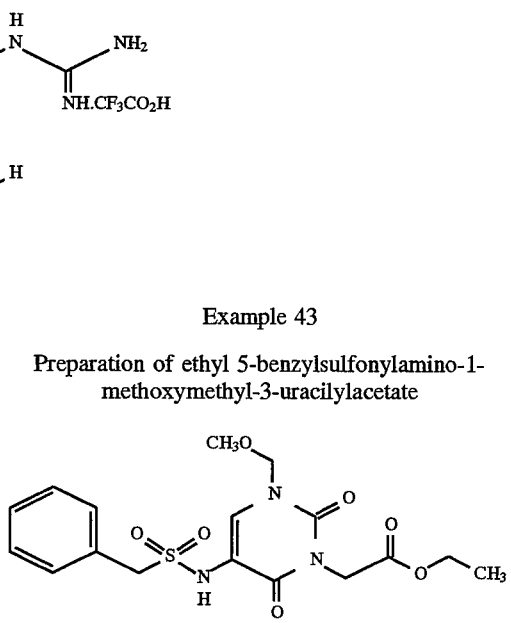

A stirred solution of the compound of Example 42 (10.0 g, 35 mmole) in ethanol (100 mL) is hydrogenated over 10% Pd/C (1.00 g) for 8 hours under balloon pressure. Celite is added, and the reaction mixture is filtered through a pad of celite, using ethyl acetate to wash. The solvent is removed in vacuo to give crude ethyl 5-amino-1-methoxymethyl-uracilylacetate.

A stirred solution of ethyl 5-amino-1-methoxymethyl-uracilylacetate (8.0 g, 31 mmole) and 2,4,6-collidine (13.7 mL, 62 mmole) in tetrahydrofuran (50 mL) is cooled in an ice bath. A solution of benzylsulfonyl chloride (5.93 g, 31 mmole) in tetrahydrofuran (50 mL) is added over a 30-minute period. After addition is complete, the solution is stirred for 1 hour at 0° C., then 3 hours at room temperature. The reaction mixture is diluted with ethyl acetate, washed with 1.0N HCl (until aqueous layer is pH 1), water, saturated sodium bicarbonate, and brine. The organic layer is dried over anhydrous magnesium sulfate, and the solvent is removed. The title compound is isolated.

Example 44

Preparation of 5-benzylsulfonylamino-1-methoxymethyl-3-uracilylacetic acid

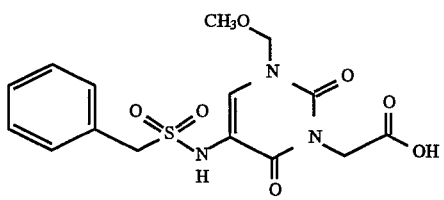

To a cooled (0° C.) suspension of the compound of Example 43 (10.0 g, 24 mmole) in methanol (50 mL) is added 1.0N NaOH (49 mL) over a period of 10 minutes. After the addition is complete, the solution is allowed to warm to room temperature over a period of 1.5 hours. The solvent is reduced under vacuum, residue diluted with water, and washed with ethyl acetate twice. The aqueous layer is acidified with 2.0N HCl to pH 1, extracted with ethyl acetate three times. The combined organic extracts are washed with water, then brine (twice). The solvent is removed to give the title compound.

Example 45

Preparation of 5-benzylsulfonylamino-1-methoxymethyl-3-uracilylacetyl-N$^g$-nitro-L-argininal ethyl cyclol

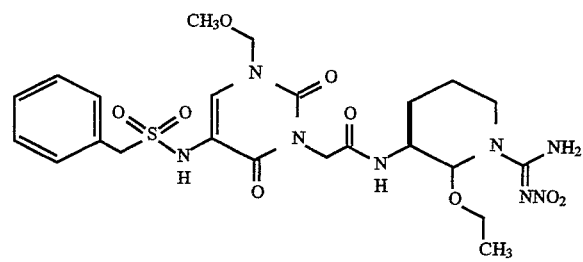

To a stirred suspension of the compound of Example 44 (10.0 g, 26 mmole), N$^g$-nitro-L-argininal ethyl cyclol, hydrochloride salt (8.38 g, 31 mmole), and N-hydroxybenzotriazole (4.0 g, 26 mmole) in acetonitrile (200 mL) cooled to 0° C. is added 1-ethyl-3-(3-dimethylamino-propyl)carbodiimide hydrochloride salt (6.0 g, 31 mmole). N-methylmorpholine (8.6 mL, 78 mmole) is added dropwise. After the addition is complete, the reaction is stirred at room temperature for 3 hours. The solvent is reduced under vacuum, and the resulting residue is dissolved in dichloromethane, washed with 2.0N HCl (to pH 1), water, saturated sodium bicarbonate and brine. The extract is dried over anhydrous magnesium sulfate, and the solvent was removed under vacuum. The crude product was chromatographed through silica gel to yield the title compound.

Example 46

Preparation of 5-benzylsulfonylamino-1-methoxymethyl-3-uracilylacetyl-L-argininal ethyl cyclol, acetate salt

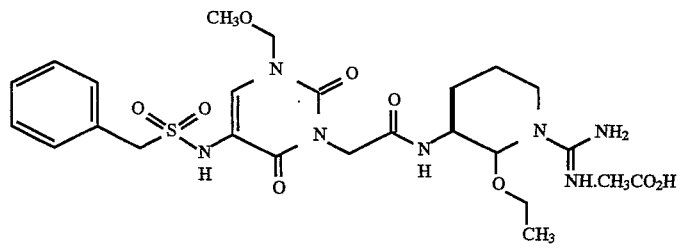

The compound of Example 45 (1.00 g) in ethanol/acetic acid/water (4:1:1, 10 mL) is hydrogenated over 10% palladium on carbon (0.30 g) for 4 hours at 20 psi. Celite is added, and the solution is filtered through a 0.2 micron filter, washing the solid with ethanol/acetic acid/water (4:1:1, 10 mL). To the filtrate was added 10% palladium on carbon (0.30 g), and the solution is hydrogenated at 20–25 psi until there is no starting material as observed by analytical HPLC. Celite is added, and the solution was filtered through a 0.2 micron filter, washing the solid with water. The solvent is reduced to a volume of 80 mL under reduced pressure, then washed with ethyl acetate. The solvent from the aqueous layer is reduced to remove the volatiles, then the sample is lyophilized to yield the title compound.

Example 47

Preparation of 5-benzylsulfonylamino-3-uracilylacetyl-L-argininal, trifluoroacetate salt

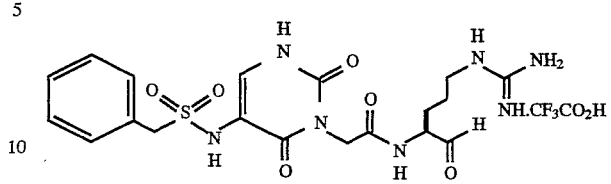

The compound of Example 46 (1.00 g) is dissolved in 3.0N hydrochloric acid (20 mL). After 3 hours, the reaction mixture was quenched with aqueous sodium acetate (to pH 3.5), then filtered through a 2 micron filter. The filtrate is purified by preparative HPLC (5×25 cm Vydac C-18 column, 0–20% acetonitrile/water containing 0.1% trifluoroacetic acid). The clean fractions, as analyzed by analytical HPLC, are combined to give the title compound.

Example 48

Preparation of 5-nitro-1-methyl-uracil

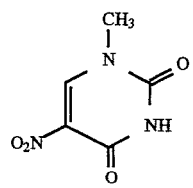

5-nitrouracil (10.00 g, 64 mmole), 1,1,1-3,3,3-hexamethyldisilazane (40 mL, 190 mmole) and chlorotrimethylsilane(4.0 mL, 32 mmole) are heated to reflux for 24 hours. The solution is concentrated under reduced pressure to afford 5-nitrouracil bis (trimethylsilyl) ether. 5-nitrouracil bis(trimethylsilyl) ether (10.0 g, 24 mmole), dimethylformamide (50 mL) and iodomethane (3.0 mL, 49 mmole) are heated in an 80° C. oil bath for 24 hours. ice water is added, and the mixture is stirred for 30 minutes, then extracted with dichloromethane (3×). The combined organic layers are dried over magnesium sulfate, filtered, and concentrated under reduced pressure to give the title compound. An alternative method of preparing the title compound is described in Example 108.

Example 49

Preparation of ethyl 5-nitro-1-methyl-3-uracilylacetate

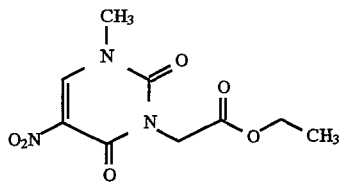

Using similar procedures to that described above in Example 42, the title compound is prepared from the compound of Example 48.

Example 50

Preparation of Ethyl 5-benzylsulfonylamino-1-methyl-3-uracilylacetate

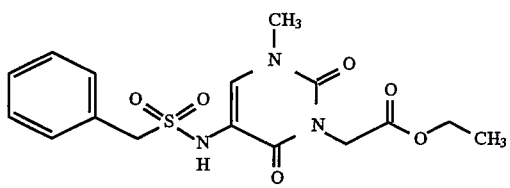

Using similar procedures to that described above in Example 43, the title compound is prepared from the compound of Example 49.

Example 51

Preparation of 5-benzylsulfonylamino-1-methyl-3-uracilylacetic acid

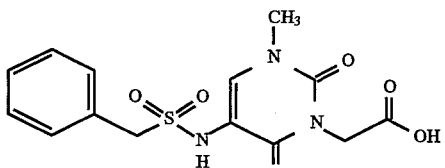

Using similar procedures to that described above in Example 44, the title compound is prepared from the compound of Example 50. An alternate method of preparing the title compound is described in Example 111.

Example 52

Preparation of 5-benzylsulfonylamino-1-methyl-3-uracilylacetyl-$N^g$-nitro-L-argininal ethyl cyclol

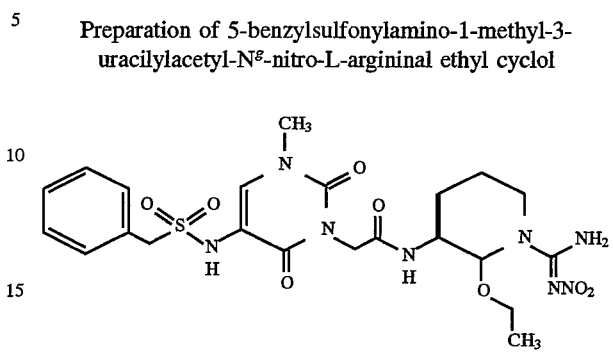

Using similar procedures to that described above in Example 45, the title compound is prepared from the compound of Example 51.

Example 53

Preparation of 5-benzylsulfonylamino-1-methyl-3-uracilylacetyl-L-argininal ethyl cyclol, acetate salt

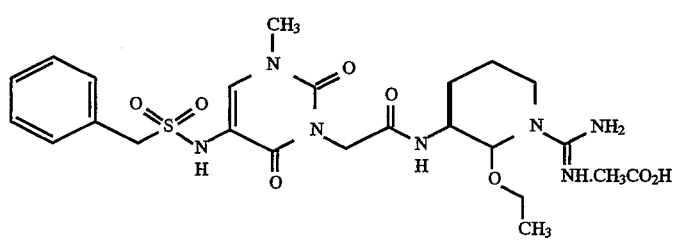

Using similar procedures to that described above in Example 46, the title compound is prepared from the compound of Example 52.

Example 54

Preparation of 5-benzylsulfonylamino-1-methyl-3-uracilylacetyl-L-argininal, trifluoroacetate salt

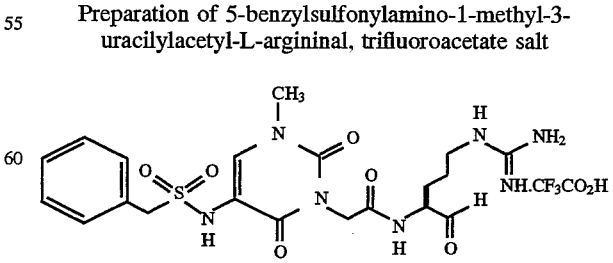

Using similar procedures to that described above in Example 47, the title compound is prepared from the compound of Example 53. An alternative method of preparing the title compound is described in Example 112 (Compound E).

Example 55

Preparation of alpha-N-benzyloxycarbonyl-omega, omega'-di-N-t-butoxycarbonyl-L-arginine lactam

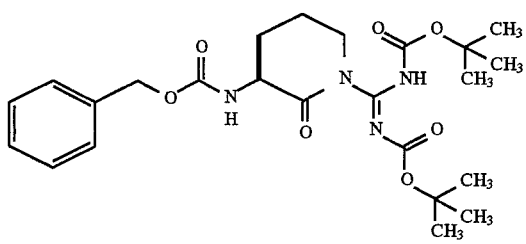

Alpha-N-t-benzyloxycarbonyl-omega,omega'-di-N-t-butoxycarbonylarginine (2.10 g, 4.1 mmole)) was dissolved in acetonitrile (25 mL). Hydroxybenzotriazole (0.63 g, 4.1 mmole) and 1-ethyl-3-(3-dimethylaminopropyl) carbodiimide hydrochloride salt (0.79 g, 4.1 mmole) were added in succession. After the reaction was stirred for 1 hour, the solvent was reduced. The residue was dissolved in ethyl acetate (50 mL), washed with water, saturated sodium bicarbonate, and brine. The solution was dried over anhydrous magnesium sulfate, filtered, and the solvent was removed in vacuo to give 1.90 g (94% yield) of the title compound. $R_f$=0.37 (10% ethyl acetate/dichloromethane).

Example 56

Preparation of alpha-N-benzyloxycarbonyl-omega, omega'-di-N-t-butoxycarbonyl-L-argininal

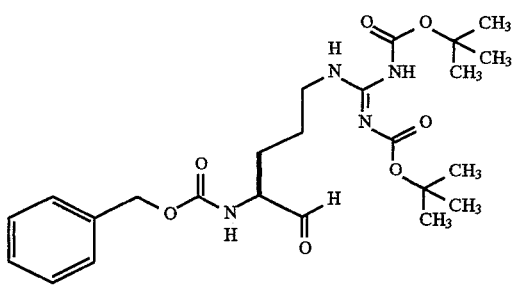

A solution of the compound of Example 55 (33.69 g, 69 mmole) in tetrahydrofuran (350 mL) was cooled to −70° C. Lithium aluminum hydride (69 mL of a 1.0M solution in tetrahydrofuran) was added dropwise while maintaining the temperature below −60° C. After the reaction mixture was stirred at −60° to −65° C. for 30 minutes, it was cooled to −70° C. 2.5M potassium bisulfate (92 mL) was added dropwise to quench the excess lithium aluminum hydride. The solution was allowed to warm to 0° C., and the mixture was filtered through celite, washing with ethyl acetate. The filtrate was washed with cold 1.0N HCl (75 mL), ice water (50 mL), cold saturated sodium bicarbonate (50 mL), then cold brine (50 mL). The extract was diluted with dichloromethane (200 mL), then dried over anhydrous magnesium sulfate. The solvent was removed in vacuo to afford 28.23 g.(83%) of the title compound. $R_f$=0.37 (5% isopropanol in dichloromethane).

Example 57

Preparation of omega,omega'-di-N-t-butoxycarbonyl-L-argininal diethyl acetal, HCl salt

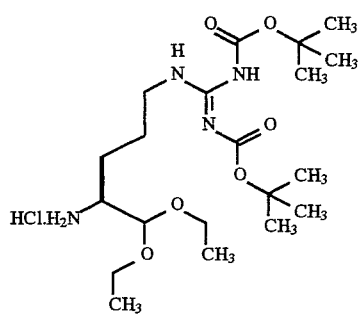

The compound of Example 56 (300 mg, 0.61 mmole) was dissolved in ethanol (3.0 mL) and concentrated HCl was added (51 microliters). After stirring overnight at room temperature, 10% Pd/C (30 mg) was added. The mixture was hydrogenated for 4 hours. TLC indicated that the reaction was complete. Celite was added, and the reaction mixture was filtered. The solution was diluted with water to a volume of 50 mL. The title compound (190 mg, 73% yield) was freeze dried to a yellow solid. $R_f$=0.26 (10% methanol/dichloromethane).

Example 58

Preparation of t-butyl (3-nitro-2-oxo-1,2-dihydropyridyl)acetate

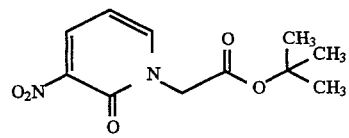

Sodium hydride (1.57 g of a 60% dispersion in mineral oil, 0.039 mole) was washed with hexanes three times (10 mL each) and suspended in dimethylformamide (25 mL). The stirred suspension was cooled in an ice bath, then 3-nitro-2-hydroxypyridine (5.00 g, 0.036 mole) was added in small portions over a 25-minute period. After the addition was complete, the reaction was stirred at 0° C. for 10 minutes, then room temperature for 30 minutes. The reaction mixture was recooled in an ice bath. t-Butyl bromoacetate (5.25 mL, 0.036 mole) was added. The reaction was stirred at 0° C. for 1 hour, then 1.5 hours at room temperature. The reaction mixture was diluted with ethyl acetate (80 mL), and ice (80 g) was added. The aqueous layer was extracted with ethyl acetate (3×200 mL). The combined organic extracts were washed with water (4×100 mL), brine (100 mL), and dried over anhydrous sodium sulfate. The solvent was removed, and the resulting residue was chromatographed through silica gel using 10% ethyl acetate/dichloromethane as eluent. The pure fractions were Combined, and the solvent was removed under vacuum to afford 6.77 g (75% yield) of the title compound as yellow solid. $R_f$=0.30 (silica gel, 20% ethyl acetate in dichloromethane).

Example 59

Preparation of t-butyl (3-amino-2-oxo-1,2-dihydropyridyl)acetate

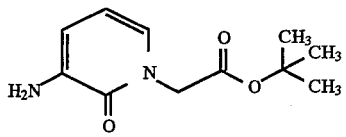

A stirred solution of the compound of Example 58 (2.00 g, 7.9 mmole) in ethanol (50 mL) was hydrogenated over 10% Pd/C (0.23 g) for 3 hours under balloon pressure. Celite was added, and the reaction mixture was filtered through a pad of Celite, using methanol/ethyl acetate to wash. The solvent was removed under vacuum to afford the title compound (1.90 g) in quantitative yield. $R_f$=0.56 (silica gel, 10% methanol in dichloromethane).

Example 60

Preparation of ethyl 3-[(allyloxycarbonyl)amino]-2-oxo-1,2-dihydropyridylacetate

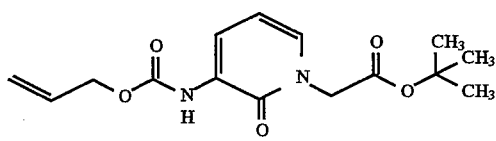

The compound of example 59 (1.7 g, 7.85 mmole) is dissolved in 50% aqueous dioxane (30 mL) and cooled to 0° C. Sodium bicarbonate (2.0 g, 24 mmole) is added in one portion. After stirring 5 minutes, allyl chloroformate (1.67 g, 16 mmole) in dioxane (4 mL) is added dropwise over a 5-minute period. After stirring for 30 minutes, the solvent is reduced to a volume of 10 mL, and extracted with dichloromethane (50 mL). The organic layer is washed with brine, the dried over anhydrous magnesium sulfate. The solvent is removed and the title compound isolated.

Example 61

Preparation of 3-[(allyloxycarbonyl)amino]-2-oxo-1,2-dihydropyridylacetic acid

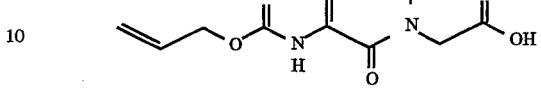

The compound of example 60 (1.00 g) is treated with 50% trifluoroacetic acid in dichloromethane (10 mL) for 1 hour at 0° C., and 3 hours at room temperature. The solution is diluted with toluene (50 mL) and the solvent is removed in vacuo to afford the title compound.

Example 62

Preparation of 3-[(allyloxycarbonyl)amino]-2-oxo-1,2-dihydropyridylacetyl-omega,omega'-di-N-t-butoxycarbonyl-L-argininal diethyl acetal

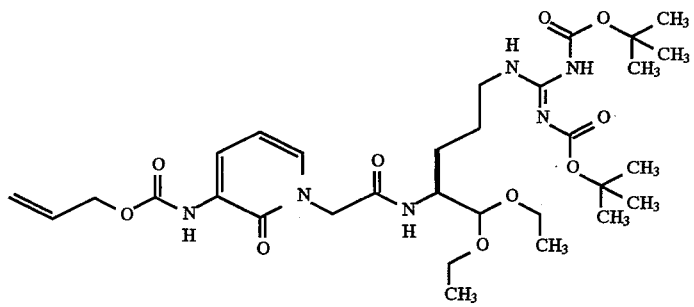

To a stirred suspension of the compound of Example 57 (500 mg, 1.98 mmole), the compound of example 61 (1.12 g, 2.37 mmole), and N-hydroxybenzotriazole (300 mg, 1.98 mmole) cooled to 0° C. is added 1-ethyl-3-(3-dimethylaminopropyl)carbodiimide hydrochloride salt (457 mg, 2.38 mmole). N-methylmorpholine (0.65 mL, 5.9 mmole) is added dropwise. After the addition is complete, the reaction is stirred at room temperature overnight. The solvent is reduced under vacuum, and the resulting residue is dissolved in ethyl acetate, washed with 1.0N HCl (to pH 1), water, saturated sodium bicarbonate and brine. The extract is dried over anhydrous magnesium sulfate, and the solvent is removed under vacuum to yield the title compound.

Example 63

Preparation of 3-[(allyloxycarbonyl)amino]-2-oxo-1,2-dihydropyridylacetyl-L-argininal, trifluoroacetate salt

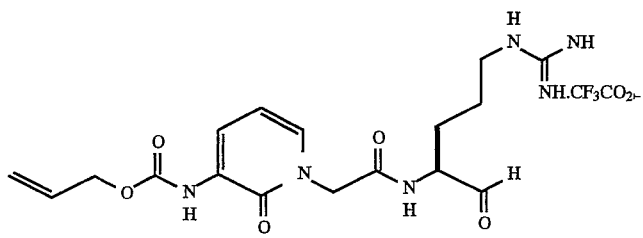

The compound of example 62 (1.0 g) is suspended in 50% aqueous acetonitrile (20 ml) and cooled in an ice bath. Hexafluorophosphoric acid (60% by weight, 10 mL) is added slowly, and the cooling bath is removed. After 30 minutes, the reaction mixture is recooled in an ice bath, and quenched with aqueous sodium acetate (2.5M solution) to pH 4, then filtered through a 2 micron filter. The filtrate is purified using preparative HPLC. The fractions are analyzed for purity by analytical HPLC (0.1% trifluoroacetic acid/ 10-40% aqueous acetonitrile), combined, and the acetonitrile is removed under reduced pressure. The remaining water is lyophilized. The title compound is recovered.

Example 64

Preparation of N-(t-butoxycarbonyl)-3-(3-pyridyl)-L-alanine methyl ester

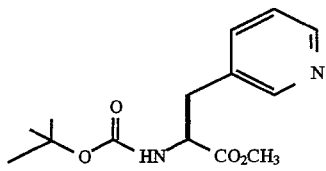

To a solution of N-(t-butoxycarbonyl)-3-(3-pyridyl) alanine (5.0 g, 18.8 mmole) in methanol (100 mL) was added thionyl chloride (2M solution in dichloromethane, 66 mL, 132 mmole). The resulting solution was stirred overnight at ambient temperature. The methanol was removed under reduced pressure to a minimum volume and ethyl acetate (100 mL) was added. The resulting white precipitate was collected in a fritted funnel. To a solution of the collected precipitate in a mixture of tetrahydrofuran/water (40 mL each) was added di-tert-butyl dicarbonate (4.8 g, 21.99 mmole) and sodium carbonate (1.95 g, 18.4 mmole). After stirring for 12 hours at ambient temperature, the reaction mixture was diluted with ethyl acetate (40 mL) and washed with a solution of saturated sodium bicarbonate (25 mL). The organic layer was dried over anhydrous sodium sulfate and concentrated under vacuum to give crude product. This product was subjected to flash column chromatography on silica gel (230–400 mesh) using a 8×52 cm column and eluting with a 10:90 mixture of ethyl acetate/hexane followed by a 60:40 mixture of ethyl acetate/hexane. 4 g (74%) of the title compound was obtained as an oil. Thin-layer chromatography gave a $R_f$=0.68 (silica gel; ethyl acetate).

Example 65

Preparation of N-(t-butoxycarbonyl)-3-(3-piperidyl)-L-alanine methyl ester, acetate salt

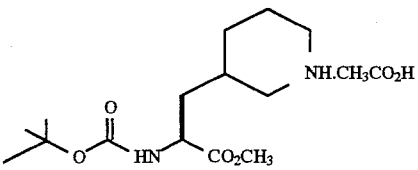

A solution of the compound of Example 64 (5 g, 17.8 mmole) in ethanol (24 mL), acetic acid (6 mL) and water (6 mL) was hydrogenated over platinum oxide (500 mg) at 45 psi for three hours. The catalyst was filtered off and the filtrate concentrated under vacuum to an oily residue (6.89 g) which was used in the next step (Example 6) without further purification. Thin-layer chromatography yielded two spots corresponding to two diastereomers with $R_f$ values of 0.16 and 0.26, respectively (silica gel; 4:1:1 n-butanol/acetic acid/water).

Example 66

Preparation of N-(t-butoxycarbonyl)-3-[3-piperidyl-(N-quanidino(bis-benzyloxycarbonyl))]-L-alanine methyl ester

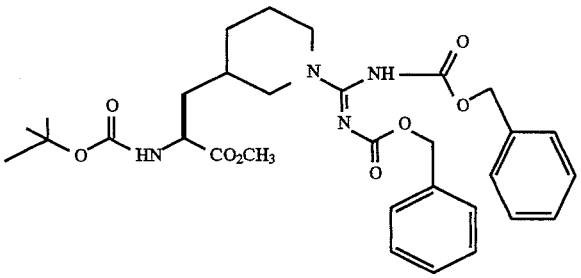

To a solution of the compound of Example 65 (6.89 g, 19.9 mmole) in tetrahydrofuran (80 mL) was added S-methylisothiourea bis-benzyloxycarbonyl (7.13 g, 19.9 mmole) followed by N-methylmorpholine (4.37 mL), and the reaction mixture was stirred at ambient temperature for 18 hours. The reaction mixture then was concentrated under vacuum and the resulting residue was dissolved in ethyl acetate (100 mL) and washed with 1N sodium bisulfate and saturated sodium chloride (50 mL each). After drying over anhydrous sodium sulfate, the solvents were removed under vacuum; the crude title compound was subjected to flash column chromatography on silica gel (230–400 mesh) using a 8×52 cm column and eluting with 1:9 ethyl acetate/ hexanes (two column volumes) followed by 1:1 ethyl acetate/hexanes. 2.75 g the title compound was obtained as a mixture of two diastereomers. Thin-layer chromatography gave two spots with $R_f$ values of 0.57 and 0.62, respectively (silica gel; 1:1 ethyl acetate/hexanes).

Example 67

Preparation of N-(t-butoxycarbonyl)-3-[3-piperidyl-(N-guanidino(bis-benzyloxycarbonyl))]-L-alaninol

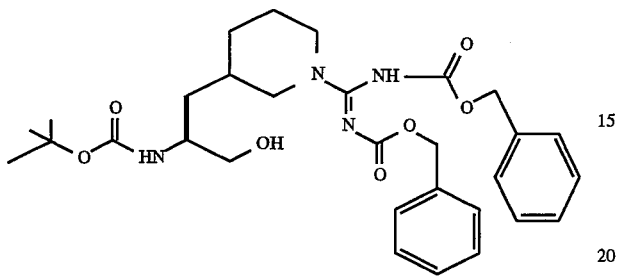

To a stirred solution of the compound of Example 66 (2.23 g, 3.7 mmole) in absolute ethanol (8 mL) and anhydrous tetrahydrofuran (4 mL) was added calcium chloride (844 mg, 7.6 mmole) and sodium borohydride (575 mg, 15.2 mmole). After stirring 12 hours at ambient temperature, the reaction mixture was concentrated under vacuum and the resulting residue was partitioned between ethyl acetate and 1N sodium bisulfate (10 mL each). The two layers were separated; organic layer was washed twice more with 1N sodium bisulfate, dried over anhydrous sodium sulfate and concentrated under vacuum gave a residue. Flash column chromatography of the residue on silica gel (230–400 mesh) using a 5.5×45 cm column and eluting with ethyl acetate gave 1.3 g of the title compound as a white foam. Thin layer chromatography yielded two spots corresponding to two diastereomers with $R_f$ values of 0.18 and 0.27, respectively (silica gel; 1:1 ethyl acetate/hexanes).

Example 68

Preparation of 3-[3-piperidyl-(N-guanidino(bis-benzyloxycarbonyl))]-L-alaninol, hydrochloride salt

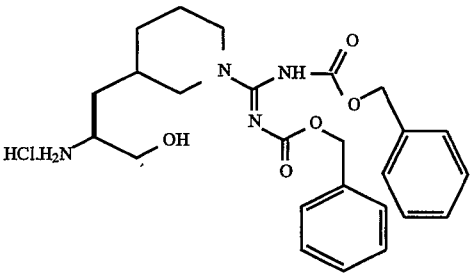

The compound of Example 67 (290 mg, 0.57 mmole) was treated with 2.5N anhydrous hydrochloric acid in ethyl acetate (2.0 mL) at ambient temperature for one hour. The solvent was removed under vacuum to a sticky-white solid (260 mg). This solid was used in the next step (Example 20) without further purification. $^1$H NMR spectrum taken in $CD_3OD$ showed no t-butoxycarbonyl protons at 1.4 ppm.

Example 69

Preparation of [3-[(benzylsulfonyl)amino]-2-oxo-1, 2-dihydropyridyl]acetyl-3-[3-piperidyl-(N-guanidino (bis-benzyloxycarbonyl))]-alaninol

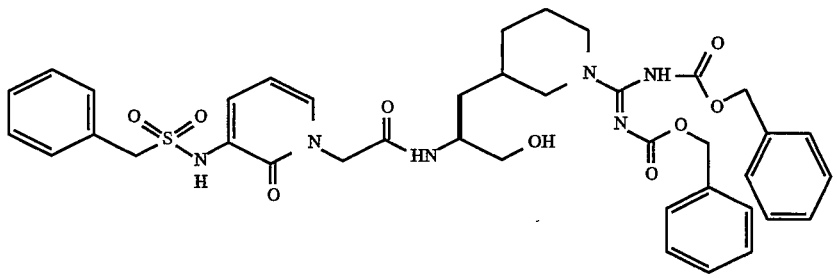

To a suspension of the compound of Example 68 (266 mg, 0.45 mmole) in acetonitrile (7 mL) is added successively the compound of Example 7 [3-[(benzylsulfonyl)amino]-2-oxo-1,2-dihydropyridyl]acetic acid (145 mg, 0.41 mmole), 1-ethyl-3-(3-dimethylaminopropyl)carbodiimide hydrochloride salt (86 mg, 0.45 mmole), 1-hydroxybenzotriazole hydrate (72 mg, 0.47 mmole) and diisopropylethylamine (2.44 mmole, 417 microliters). The solution is stirred at ambient temperature for twelve hours. The solvent is removed under reduced pressure and the remaining residue is dissolved in ethyl acetate (15 mL) and washed two times each with 10 mL portions of 1N sodium bisulfate, saturated sodium bicarbonate and saturated sodium chloride solution. The organic layer is dried over sodium sulfate and concentrated to crude product. The title compound is isolated.

Example 70

Preparation of [3-[(benzylsulfonyl)amino]-2-oxo-1,2-dihydropyridyl]acetyl-3-[3-piperidyl-(N-guanidino)]alaninol, acetate salt

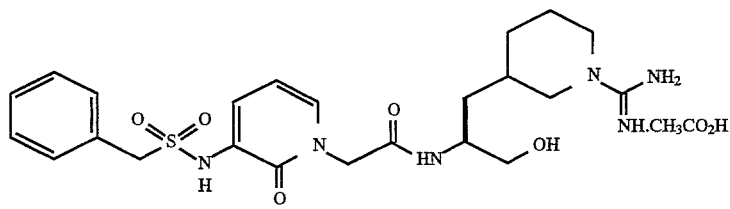

The compound of Example 69 (123 mg, 0.16 mmole) is subjected to catalytic hydrogenation in methanol (8 mL), and acetic acid (2 mL) and water (2 mL) in the presence of palladium on carbon (20 mg) at 40 psi for 4 hours. The title compound is obtained.

Example 71

Preparation of [3-[(benzylsulfonyl)amino]-2-oxo-1,2-dihydropyridyl]acetyl-3-[3-piperidyl-(N-guanidino)]alaninal

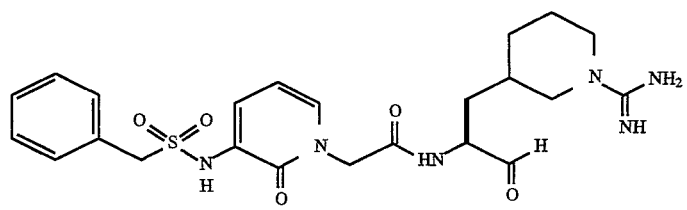

To a chilled solution of the compound of Example 70 (107 mg, 0.19 mmole) in dimethylsulfoxide and toluene (2 mL each) is added dichloroacetic acid (78 microliter, 0.94 mmole) followed by 1-ethyl-3-(3-dimethylaminopropyl) carbodiimide hydrochloride salt (0.36 g, 1.9 mmole) at one minute later. The reaction is stirred for 5 minutes at 0° C. and 85 minutes at ambient temperature, and quenched with 30 mL water. The water layer is extracted twice with diethyl ether (15 mL portions), diluted to 60 mL with water and is purified by high pressure liquid chromatography using a reverse phase column containing a C-18 resin comprised of 10 micron-size gel particles with a 300 angstrom pore size. The column is eluted with a water/acetonitrile (containing 0.1% trifluoroacetic acid) gradient where the gradient is run from 10% to 30% acetonitrile. Each diasteromer of the title compound is isolated.

Example 72

Preparation semicarbazid-4-yl diphenylmethane, trifluoroacetate salt

Step 1:

A solution of carbonyldiimidazole (16.2 g, 0.10 mole) in 225 mL of dimethylformamide was prepared at room temperature and allowed to stir under nitrogen. A solution of t-butyl carbazate (13.2 g, 0.100 moles) in 225 mL dimethylformamide was then added dropwise over a 30 minute period. Next, diphenylmethylamine (18.3 g, 0.10 moles) was added over a 30 minute period. The reaction was allowed to stir at room temperature under nitrogen for one hour. Water (10 mL) was added and this mixture was concentrated to about 150 mL under vacuum. This solution was poured into 500 mL water and extracted with 400 mL of ethyl acetate. The ethyl acetate phase was extracted two times each with 75 mL 1N HCl, water, saturated sodium bicarbonate and brine, and then was dried with anhydrous magnesium sulfate. The mixture was filtered and the solution was concentrated to give 29.5 g (85% yield) of 1-t-butoxycarbonyl-semicarbazid-4-yl diphenylmethane as a white foam. This material may be purified by recrystallization from ethyl acetate/hexane, but was pure enough to use directly in step 2: mp 142°–143° C. $^1$H NMR (CDCl$_3$) delta 1.45 (s, 9H), 6.10 (dd, 2H), 6.42 (s, 1H), 6.67 (bs, 1H), 7.21–7.31 (m, 10H). Anal. Calc'd. for $C_{19}H_{23}N_3O_3$: C, 66.84; H, 6.79; N, 12.31. Found: C, 66.46; H, 6.75; N, 12.90.

Step 2:

A solution of 3.43 g (10 mmole) of 1-t-butoxycarbonyl-semicarbazid-4-yl diphenylmethane in 12.5 mL of dichloromethane was treated with 12.5 mL of trifluoroacetic acid at 0° C. The reaction mixture was allowed to stir for 30 minutes at this temperature. The reaction mixture was then added dropwise to 75 mL of diethyl ether to give a precipitate. The resulting precipitate was filtered off and washed with diethyl ether to give 2.7 g (80% yield) of the title compound; mp 182°–184° C.

Example 73

Preparation of 3-thioamidobenzyl-N-acetylaminomalonic acid diethyl ester

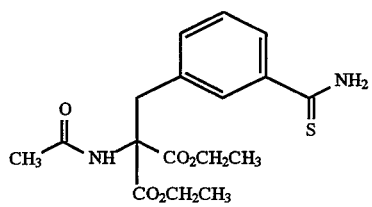

To a stirred solution of alpha-bromo-meta-tolunitrile (45.0 g, 0.24 mole), diethyl acetamidomalonate (48.0 g, 0.22 mole) and potassium iodide ((3.0 g, 0.018 mole) in dioxane (500 mL) was added 2.5M sodium ethoxide in ethanol (100 mL) dropwise under an argon atmosphere. After the addition was complete, the solution was refluxed for 6 hours. The reaction mixture was allowed to stand overnight at room temperature, then diluted with brine (250 mL) and water (250 mL), and extracted with ethyl acetate four times (1.0 L total). The combined extracts were washed with water (100 mL), 10% citric acid (100 mL), water (100 mL) and brine (2×50 mL), then dried over anhydrous magnesium sulfate and filtered; the solvent was removed under vacuum. The crude residue was recrystallized from ethyl acetate and diethyl ether in two crops to yield 43.51 g (60%) of the 3-cyanobenzyl-N-acetylaminomalonic acid diethyl ester as yellow crystals.

$H_2S(g)$ was bubbled into a rapidly stirring solution of 3-cyanobenzyl-N-acetylaminomalonic acid diethyl ester (44.3 g, 0.13 mmole) in pyridine (300 mL) and triethylamine (100 mL) for 40 minutes. The reaction mixture was stirred at room temperature for 16 hours, then poured into 3.0 L of water. A yellow precipitate formed immediately. The solution was allowed to stand at 4° C. for 4 hours, then was filtered. The crude title compound was recrystallized from ethyl acetate and hexanes to yield 48.1 g (98%) of the title compound as yellow crystals. m.p. 183°–186° C. $^1$H NMR (CDCl$_3$): delta 1.31 (t, J=7.1 Hz, 6H), 2.06 (s, 3H), 3.70 (s, 2H), 4.29 (q, J=7.1 Hz, 4H), 4.80–4.87 (m, 1H), 6.60 (s, 1H), 7.10–7.20 (m, 1H), 7.27–7.35 (m, 2H), 7.60–7.70 (m, 2H). Anal. Calc'd for $C_{17}H_{22}N_2O_5S$: C, 55.72; H, 6.05; N, 7.64. Found: C, 55.55; H, 5.96; N, 7.76.

Example 74

Preparation of 3-amidino-D,L-phenylalanine, dihydrochloride salt

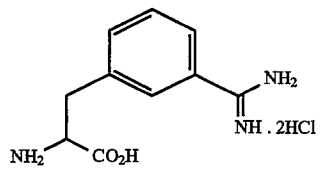

The compound of Example 73 (48.1 g, 0.13 mmole) was dissolved in acetone (800 mL). Iodomethane (18.3 mL, 0.19 mole, 1.5 equivalents) was added, and the solution was refluxed for 30 minutes. The solution was cooled to room temperature, and the intermediate thioimidate was filtered, dried and dissolved in methanol (500 mL). Ammonium acetate (14.8 g, 0.19 mole, 2 equivalents) was added. The reaction mixture was refluxed for 1 hour, then cooled to room temperature, and poured into ether (1.2 L). The solution was allowed to stand at 4° C. for 72 hours. The crude 3-amidinobenzyl-N-acetylaminomalonic acid diethyl ester was filtered, washed with ether, air dried, and then refluxed in concentrated HCl (250 mL) for 3 hours. The reaction mixture was concentrated under vacuum, diluted with water (0.5 L), and concentrated under vacuum again. These steps were repeated. The crude title compound was purified by cation-exchange (Sephadex SP-C25) using a gradient of 0–1.0N HCl as eluent to yield 10.8 g (30%) of the title compound as an off-white solid. $^1$H NMR (D$_2$O): delta 3.14–3.29 (2H, m), 4.17 (dd, J=7.4, 6.2 Hz, 1H), 7.42–7.69 (4H, m). Anal. Calc'd for $C_{10}H_{13}N_3O_2 \cdot 2HCl \cdot 1.9H_2O$: C, 38.20; H, 6.03; N, 13.36. Found: C, 38.51; H, 5.64; N, 12.89.

Example 75

Preparation of N-alpha-Boc-N-omega-4-methoxy-2,3,6-trimethylbenzenesulfonyl-3-amidino-D,L-phenylalanine

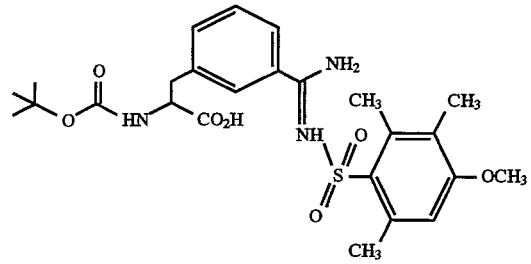

The compound of Example 74 (3-amidino-D,L-phenylalanine) (4.00 g, 13 mmole) was dissolved in 50% aqueous dioxane (20 mL). Sodium bicarbonate (3.38 g, 40 mmole) was added, followed by di-t-butyl dicarbonate (2.93 g, 13 mmole) in dioxane (4 mL). The reaction mixture was stirred for 18 hours at room temperature. The solution was cooled in an ice bath, and 4.0N sodium hydroxide was added dropwise until the solution was pH 12. 4-methoxy-2,3,6-trimethylbenzenesulfonyl chloride (8.01 g, 32 mmole) in dioxane (10 mL) was added dropwise. 4.0N sodium hydroxide was added as needed to keep the pH at 12. The ice bath was removed. After 1 hour, 1.0N HCl was added to bring the solution to pH 7–8. The solution was diluted with an additional 50 mL of water and then was washed with ethyl acetate two times (20 mL each). The aqueous layer was acidified to pH 1.0 with 1.0N HCl and extracted with ethyl acetate three times (100 mL total). The combined organic layers were washed with water (20 mL) and brine twice (10 mL each). The organic layer was dried over anhydrous magnesium sulfate and the solvent was removed under vacuum. The residue was dissolved in a minimum amount of dichloromethane, then added dropwise to ether (25 mL). Solid impurities were removed by filtering and the solvent removed from the filtrate under vacuum to give 4.90 g (68% crude yield) of the title compound as an off-white foam. A 30 mg sample of the title compound was further purified by preparative thin-layer chromatograph developing with 1% acetic acid/5% isopropanol/dichloromethane to give 9 mg of the title compound in a purer form. $R_f$=0.16 (1% acetic acid/5% isopropanol/dichloromethane). $^1$H NMR (CD$_3$OD): delta 1.32 (s, 9H), 2.14 (s, 3H), 2.63 (s, 3H), 2.71 (s, 3H), 2.93 (dd, J=13.7, 9.3 Hz, 1H), 3.22 (dd, J=13.7, 4.3 Hz, 1H), 3.85 (s, 3H), 4.34–4.37 (m, 1H), 6.72 (s, 1H), 7.35–7.47 (2H, m), 7.69–7.75 (m, 2H).

Example 76

Preparation of N-alpha-Boc-N-omega-4-methoxy-2, 3,6-trimethylbenzenesulfonyl-3-amidino-D,L-phenylalanine-N-methyl-O-methyl-carboxamide

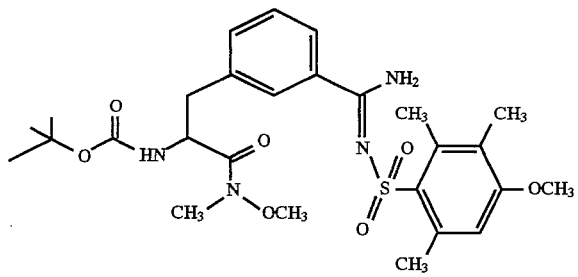

To a stirred solution of compound of Example 75 (1.00 g, 1.92 mmole), O,N-dimethyl hydroxylamine hydrochloride (375 mg, 3.85 mmole), hydroxybenzotriazole hydrate (294 mg, 1.92 mmole) and 4-methylmorpholine (1.06 mL, 9.62 mmole) in tetrahydrofuran (4 mL), cooled in an ice bath, was added 1-ethyl-3-(3-dimethylamino-propyl)carbodiimide hydrochloride salt (406 mg, 2.12 mmole). The ice bath was removed, and the reaction mixture was stirred for 2 hours at room temperature. The reaction mixture was diluted with ethyl acetate (75 mL), washed with water, 10% citric acid, water, saturated sodium bicarbonate, and brine. The organic layer was dried over anhydrous magnesium sulfate and the solvent was removed under vacuum. 750 mg (69%) of the title compound was isolated. $^1$H NMR (CDCl$_3$): delta 1.33 (s, 9H), 2.14 (s, 3H), 2.66 (s, 3H), 2.75 (s, 3H), 2.80–2.88 (m, 1H), 3.06–3.20 (m, 4H), 3.70 (s, 3H), 3.84 (s, 3H), 4.98–5.06 (m, 1H), 5.21 (d, J=8.7 Hz, 1H), 6.48 (bs, 1H), 6.58 (s, 1H), 7.30–7.34 (m, 2H) 7.60–7.68 (m, 2H), 8.11 (bs, 1H). Anal. Calc'd for C$_{27}$H$_{38}$N$_4$O$_7$S.0.5H2O: C, 56.73; H, 6.88; N, 9.80. Found: C, 56.97; H, 6.66; N, 9.43.

Example 77

Preparation of N-alpha-Boc-N-omega-4-methoxy-2, 3,6-trimethylbenzenesulfonyl-D,L-3-amidinophenylalaninal

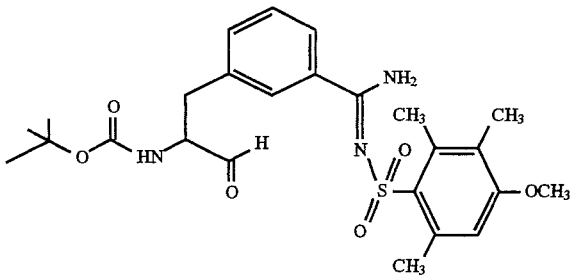

To a stirred solution of LiAlH$_4$ (2.00 mL of a 1.0M solution in tetrahydrofuran, 1.24 mmole) in tetrahydrofuran (8 mL), cooled in a dry ice/acetone bath, the compound of Example 76 (0.75 g, 1.9 mmole in tetrahydrofuran (5 mL)) was added dropwise. The cooling bath was removed and the reaction mixture was allowed to warm to 5° C. The reaction mixture was re-cooled in the dry ice acetone bath and quenched with 3.0 mL of a 1:2.7 wt./wt. solution of potassium bisulfate in water. The reaction mixture was allowed to warm to room temperature, stirred for 3 hours, filtered and concentrated under vacuum. The residue was dissolved in ethyl acetate (20 mL), and washed with 10% citric acid (2 mL), water (2 mL), saturated sodium bicarbonate (2 mL) and brine (2 mL). The organic layer was dried over anydrous magnesium sulfate and the solvent was removed under vacuum to yield 580 mg (86%) of the title compound. $^1$H NMR (CDCl$_3$): delta 1.31 (s, 9H), 2.07 (s, 3H), 2.57 (s, 3H), 2.67 (s, 3H),2.90–3.17 (2H, m), 3.77 (s, 3H), 4.33–4.40 (1H, m), 5.02–5.08 (1H, m), 6.48 (1H, s), 7.23–7.31 (2H, m), 7.50–7.62 (2H, m), 7.94, (1H, bs), 8.05 (1H, bs), 9.55 (1H, s). Anal. Calc'd for C$_{25}$H$_{33}$N$_3$O$_6$S.0.5H2O: C, 58.58; H, 6.69; N,8.20. Found: C, 58.57; H, 6.72; N, 7.98.

Example 78

Preparation of N-alpha-Boc-N-omega-4-methoxy-2, 3,6-trimethylbenzenesulfonyl-D,L-3-amidinophenylalaninal-semicarbazonyl-4-N-diphenylmethane

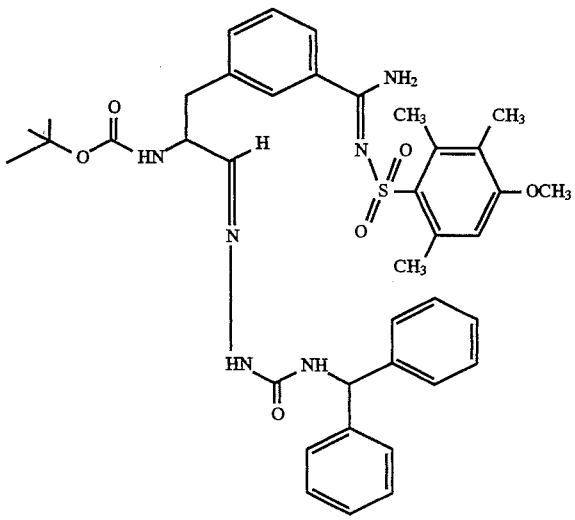

The compound of Example 77 (0.58 g, 1.9 mole), the compound of Example 72 (410 mg, 1.15 mole) and sodium acetate trihydrate (188 mg, 1.38 mole) were refluxed in 75% aqueous ethanol (10 mL) for 1 hour. After the reaction mixture was cooled to room temperature, it was diluted with ethyl acetate (50 mL), washed with 1.0N HCl (5 mL), water (5 mL), saturated sodium bicarbonate (5 mL) and brine (2×5 mL), and dried over anhydrous magnesium sulfate. The solvent was removed under vacuum to yield 750 mg (89% yield) of the title compound as an off-white foam. Analysis calculated for $C_{39}H_{46}N_6O_6S \cdot 1.0H_2O$: C, 62.88; H, 6.49; N, 11.28. Found: C, 63.14; H, 6.35N, 11.10.

The compound of Example 78 (750 mg, 1.9 mmole) was treated with 50% trifluoroacetic acid/dichloromethane (3 mL) for 30 minutes at room temperature. The reaction mixture was added dropwise to ether (50 mL). The solution was allowed to stand at 4° C. for 18 hours. The product was filtered, and dried under vacuum to yield 600 mg (79% yield) of the title compound as an off-white solid. Analysis calculated for $C_{39}H_{46}N_6O_6S \cdot 1.3CF_3CO_2H$: C, 56.72; H, 5.11; N, 10.84. Found: C, 56.34; H, 5.47; N, 11.49.

Example 80

Preparation of [3-[(benzylsulfonyl)amino]-2-oxo-1,2-dihydropyridyl]acetyl-D,L-N-omega-4-methoxy-2,3,6-trimethylbenzenesulfonyl-D,L-3-amidinophenyl alaninal-semicarbazonyl-4-N-diphenylmethane

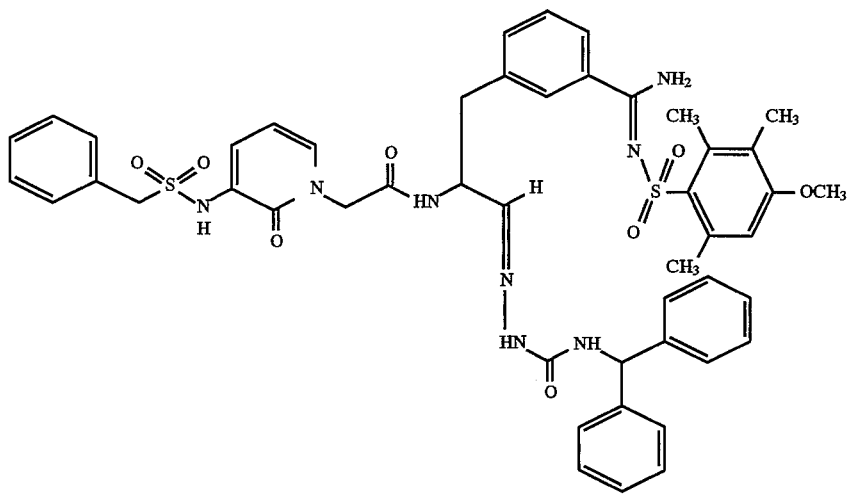

Example 79

Preparation of N-omega-4-methoxy-2,3,6-trimethylbenzene sulfonyl-D,L-3-amidinophenylalaninal-semicarbazonyl-4-N-diphenylmethane, trifluoroacetate salt

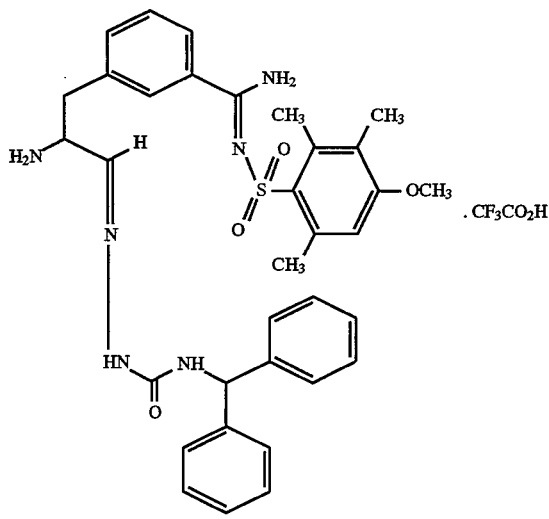

1-Ethyl-3-(3-dimethylamino-propyl)carbodiimide hydrochloride salt (94 mg, 0.94 mole) is added in one portion to a stirred solution of the compound of Example 7 (303 mg, 0.49 mole), hydroxybenzotriazole (75 mg, 0.49 mmole), and 4-methylmorpholine (0.24 mL, 2.2 mole) in dimethylformamide (5 mL) with cooling in an ice bath. After 30 minutes, the compound of Example 79 (363 mg, 0.49 mole) is added. After an additional 2 hours, the reaction mixture is diluted with water (25 mL) and brine (25 mL). The product is filtered and dissolved into ethyl acetate (25 mL). The solution is washed with 10% citric acid, water, saturated sodium bicarbonate and brine, and is dried over anhydrous magnesium sulfate. The solvent is removed under vacuum. The resulting residue is chromatographed by flash chromatography on silica gel to give the title compound.

Example 81

Preparation of [3-[(benzylsulfonyl)amino]-2-oxo-1,2-dihydropyridyl]acetyl-D,L-3-amidinophenyl alaninal semicarbazone

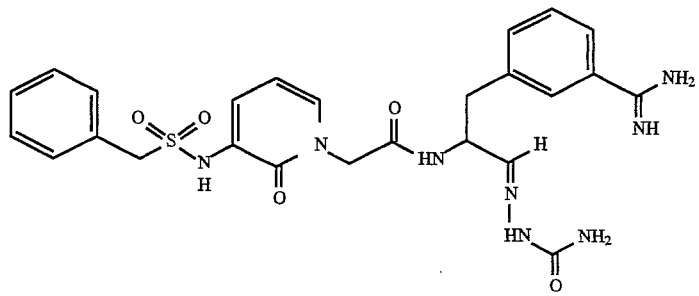

The compound of Example 80 (102 mg, 0.11 mmole) is treated with hydrofluoric acid/anisole (9:1) for 30 minutes at −20° C. and 0° C. for 30 minutes. After removal of the hydrofluoric acid, the resulting residue is dissolved in 20% aqueous acetic acid and washed with diethyl ether. The aqueous layer is lyophilized to a powder, then is purified by preparative HPLC (C-18, eluting with 10–40% acetonitrile-water gradient containing 0.1% trifluoroacetic acid) to give the title compound.

Example 82

Preparation of [3-[(benzylsulfonyl)amino]-2-oxo-1, 2-dihydromyridyl]acetyl-D,L-3-amidinophenyl alaninal

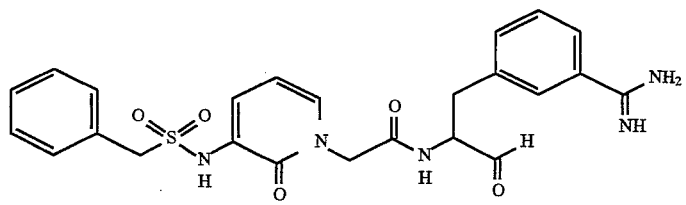

The compound of Example 81 (16.6 mg, 30 micromole) is dissolved in methanol (1 mL) and 1% aqueous trifluoroacetic acid (5 mL), then formalin (0.23 mL) is added. After 40 minutes, the solution is filtered through a 2 micron filter, diluted to a volume of 15 mL with water, and then is purified by preparative HPLC (C-18, eluting with 10–40% acetonitrile-water gradient containing 0.1% trifluoroacetic acid). The fractions containing the title compound are pooled and lyophilized to give the title compound.

Example 83

Preparation of ethyl(3-[(N-t-butyloxycarbonyl) amino]-2-oxo-1,2-dihydropyridyl) acetate

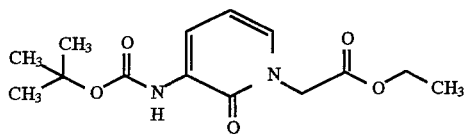

A stirred solution of the compound of Example 5 (44.5 g, 0.197 mole) in ethanol (200 mL) was hydrogenated over 10% Pd/C (2.25 g) for 16 h under balloon pressure. Celite was added, and the reaction mixture was filtered through a pad of celite in a 600 mL fritted funnel (5 cm depth), using ethyl acetate to wash. The solvent was removed under vacuum, diluted with ethyl acetate (200 mL) and toluene (200 mL), and the solvent was removed under vacuum to give crude ethyl(3-amino-2-oxo-1,2-dihydropyridyl)acetate (40.0 g, 0.204 mol) in quantitative yield.

A stirred solution of ethyl(3-amino-2-oxo-1,2-dihydropyridyl)acetate (2.00 g, 10 mmol) and sodium bicarbonate (1.69 g, 9.5 mmol) in 50% aqueous dioxane (20 ml) is cooled in an ice bath. A solution of di-t-butyldicarbonate (2.08 g, 20 mmol) in dioxane (10 ml) is added over a 5 minute period. After addition is complete, the solution is stirred for 16 hours at room temperature. The reaction mixture is diluted with ethyl acetate (100 mL), washed with 1.0N HCl (until aqueous layer is pH 1), water, saturated sodium bicarbonate, and brine. The organic layer is dried over magnesium sulfate, and the solvent is removed. The title compound is isolated.

Example 84

Preparation of ethyl(3-[(N-t-butyloxycarbonyl-N-methyl)amino]-2-oxo-1,2-dihydropyridyl)acetate

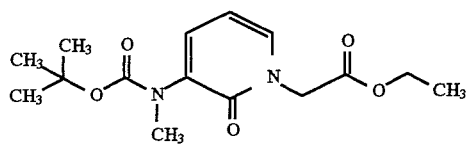

The compound of Example 83 (3.00 g, 10 mmol) and iodomethane (1.2 mL, 20 mmol) are dissolved in tetrahydrofuran (30 mL), and the solution is cooled to 0° C. under a nitrogen atmosphere. Sodium hydride (0.44 g of a 60% dispersion in mineral oil, 11 mmol) is added cautiously with gentle stirring. After the addition is complete, the reaction mixture is stirred at room temperature for 16 h. Ethyl acetate (50 mL) is added, followed by water, to destroy the excess sodium hydride. The organic layer is washed with water, 5% aqueous sodium thiosulfate (to remove the iodine), water and brine, dried over magnesium sulfate, and evaporated. The title compound is isolated.

Example 85

Preparation of (3-[(N-t-butyloxycarbonyl-N-methyl)amino]-2-oxo-1,2-dihydropyridyl)acetic acid

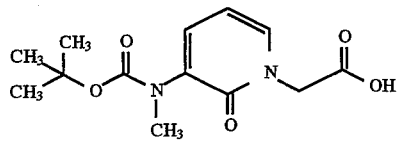

To a cooled (0° C.) suspension of the compound of Example 84 (3.2 g, 10 mmole) in methanol (10 mL) is added 1.0N NaOH (12 ml) over a period of 10 minutes. After the addition is complete, the solution is allowed to warm to room temperature over a period of 3 h. The solvent is reduced under vacuum, the residue is diluted with water (25 mL), and washed with ethyl acetate. The aqueous layer was acidified with 2.0N HCl to pH 1, extracted with ethyl acetate three times. The combined organic extracts are washed with water, then brine (twice). The solvent is removed, and the title compound is isolated.

Example 86

Preparation of [3-(N-t-butyloxycarbonyl-N-methyl)amino-2-oxo-1,2-dihydropyridyl]acetyl-N$^g$-nitro-L-argininal ethyl cyclol

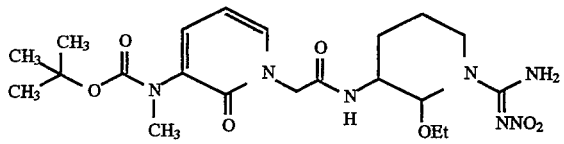

To a stirred suspension of the compound of Example 85 (2.2 g, 7.7 mmole), N$^g$-nitro-L-argininal ethyl cyclol, hydrochloride salt (2.47 g, 9.2 mmol), and N-hydroxybenzotriazole (1.17 g, 7.7 mmole) cooled to 0° C. is added EDC (1.77 g, 9.2 mmole). N-methylmorpholine (2.5 mL, 23 mmole) is added dropwise. After the addition is complete, the reaction is stirred at room temperature for 3 hours. The solvent is reduced under vacuum, and the resulting residue is dissolved in dichloromethane, washed with 2.0N HCl (to pH1), water, saturated sodium bicarbonate and brine. The extract is dried over magnesium sulfate, and the solvent is removed under vacuum. The title compound is isolated.

Example 87

Preparation of [3-(N-t-butyloxycarbonyl-N-methyl)amino-2-oxo-1,2-dihydropyridyl]acetyl-L-argininal ethyl cyclol, acetate salt

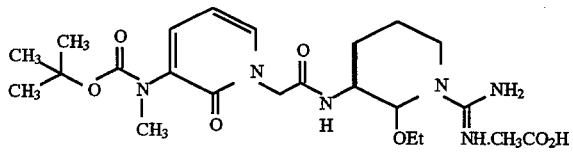

The compound of Example 86 (5.5 g, 11 mmole) in ethanol/acetic acid/water (4:1:1, 60 mL) is hydrogenated over 10% palladium on carbon (1.80 g) for 4 hours at 20 psi. Celite is added, and the solution is filtered through a 0.2 micron filter, washing the solid with ethanol/acetic acid/water (4:1:1, 60 mL). To the filtrate is added 10% palladium on carbon (1.80 g), and the solution is hydrogenated at 20–25 psi for 40 hours. Celite is added, and the solution is filtered through a 0.2 micron filter, washing the solid with water (200 mL). The solvent is reduced to a volume of 200 mL under reduced pressure, then washed with ethyl acetate (50 mL). The solvent from the aqueous layer is reduced to remove the volatiles, then the sample is lyophilized to yield the title compound.

Example 88

Preparation of [3-(N-t-butyloxycarbonyl-N-methyl)amino-2-oxo-1,2-dihydropyridyl]acetyl-L-argininal, trifluoroacetate salt

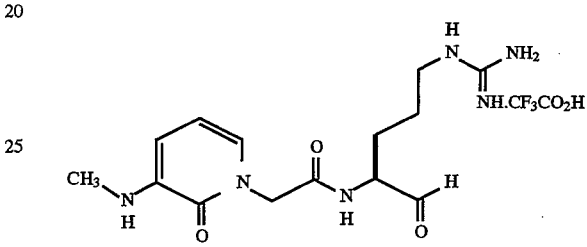

The compound of Example 87 (4.7 g, 9.2 mmole) is suspended in 3.0N HCl (100 mL) is added. After stirring for 3 hours, the reaction mixture is quenched with 2.5M aqueous sodium acetate to pH 3.5–4, then filtered through a 2 micron filter. The filtrate is purified by preparative HPLC (Waters PrepPak cartridge, Delta-Pak C18, 300 angstrom column, 0–40% acetonitrile/water containing 0.1% trifluoroacetic acid). The clean fractions are combined to give the title compound.

Example 89

General Procedure for Reaction of ethyl(3-amino-2-oxo-1,2-dihydropyridyl)acetate with sulfonyl or sulfamoyl chlorides To a stirred solution of ethyl(3-amino-2-oxo-1,2-dihydropyridyl)acetate (5.89 g, 30 mmole) in dry tetrahydrofuran (300 mL) is added the 2,4,6-collidine (7.93 mL, 60 mmol) and the solution is cooled to 0° C. under nitrogen. The appropriate sulfonyl or sulfamoyl chloride listed below (33 mmol) is dissolved in tetrahydrofuran (25–75 mL) is added dropwise. After the addition is complete, the reaction mixture is stirred for 30 minutes-1 hour at 0° C. and then at ambient temperature for 0–72 hours. The reaction mixture is diluted with ethyl acetate, washed successively with 1.0N HCl, water, saturated sodium bicarbonate and brine, dried over magnesium sulfate, and the solvent is removed in vacuo. The residue is chromatographed on silica gel using a gradient system of dichloromethane and 1–4% methanol in dichloromethane to afford the product, judged pure by TLC (silica gel). Using this method and the starting materials listed below, intermediates having the formula given below are made:

[Structure: sulfonamide-pyridone-glycine ethyl ester]

| R = | starting material |
|---|---|
| phenyl | benzenesulfonyl chloride |
| 1-naphthyl | 1-naphthylsulfonyl chloride |
| 2-naphthyl | 2-naphthylsulfonyl chloride |
| 2-carbomethoxyphenyl | 2-carbomethoxybenzenesulfonyl chloride |
| 2-trifluoromethylbenzyl | 2-trifluoromethylbenzenesulfonyl chloride |
| 2-cyclohexylamino | cyclohexylsulfamoyl chloride |
| 2-trifluoromethylphenyl | 2-trifluorobenzenesulfonyl chloride |
| 3-trifluoromethylphenyl | 3-trifluorobenzenesulfonyl chloride |
| 4-trifluoromethylphenyl | 4-trifluorobenzenesulfonyl chloride |
| 2-methylphenyl | 2-methylbenzenesulfonyl chloride |
| 3-methylphenyl | 3-methylbenzenesulfonyl chloride |
| 2-methyl-5-fluorophenyl | 2-methyl-5-fluorobenzenesulfonyl chloride |
| 2-methoxyphenyl | 2-methoxybenzenesulfonyl chloride |
| 3-methoxyphenyl | 3-methoxybenzenesulfonyl chloride |
| 2-methoxy-5-chlorophenyl | 2-methoxy-5-chlorobenzenesulfonyl chloride |
| 2-nitrophenyl | 2-nitrobenzenesulfonyl chloride |
| 2-trifluoromethoxyphenyl | 2-trifluoromethoxybenzenesulfonyl chloride |
| 2,5-dichlorophenyl | 2,5-dichlorobenzenesulfonyl chloride |
| 2,5-dimethoxy | 2,5-dimethoxybenzenesulfonyl chloride |
| 2-fluorophenyl | 2-fluorobenzenesulfonyl chloride |
| 3-fluorophenyl | 3-fluorobenzenesulfonyl chloride |

Example 90

General Procedure for the Preparation of Compounds of the Present Invention

Following the four-step protocol outlined in Examples 7–10 (hydrolysis, coupling, hydrogenation and hydrolysis), certain of the intermediates of Example 89 are used to synthesize the following compounds of the present invention (as their trifluoroacetic acid salts):

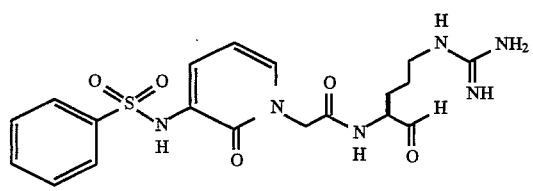

(3-phenylsulfonylamino-2-oxo-1,2-dihydro-pyridyl)acetyl-L-argininal, Compound B

[3-(1-naphthyl)sulfonylamino-2-oxo-1,2-dihydro-pyridyl]acetyl-L-argininal,

[3-(2-naphthyl)sulfonylamino-2-oxo-1,2-dihydro-pyridyl]acetyl-L-argininal,

[3-(2-carbomethoxyphenyl)sulfonylamino-2-oxo-1,2-dihydro-pyridyl]acetyl-L-argininal,

[3-(2-trifluoromethylbenzyl)sulfonylamino-2-oxo-1,2-dihydro-pyridyl]acetyl-L-argininal, (3-cyclohexylaminosulfonylamino-2-oxo-1,2-dihydro-pyridyl)acetyl-L-argininal,

[3-(2-trifluoromethylphenyl)sulfonylamino-2-oxo-1,2-dihydro-pyridyl]acetyl-L-argininal,

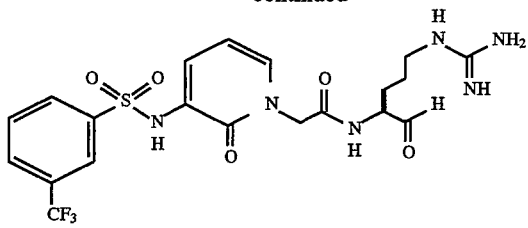

[3-(3-trifluoromethylphenyl)sulfonylamino-2-oxo-1,2-dihydro-pyridyl]acetyl-L-argininal,

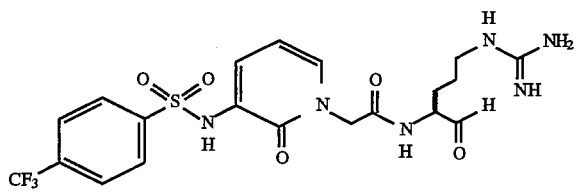

[3-(4-trifluoromethylphenyl)sulfonylamino-2-oxo-1,2-dihydro-pyridyl]acetyl-L-argininal,

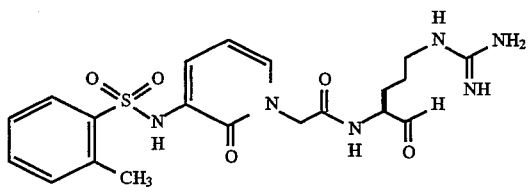

[3-(2-methylphenyl)sulfonylamino-2-oxo-1,2-dihydro-pyridyl]acetyl-L-argininal,

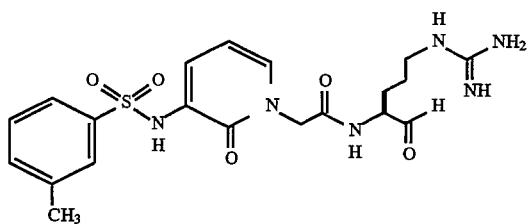

[3-(3-methylphenyl)sulfonylamino-2-oxo-1,2-dihydro-pyridyl]acetyl-L-argininal,

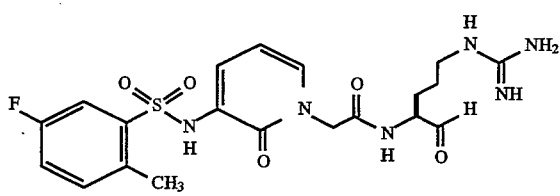

[3-(2-methyl-5-fluorophenyl)sulfonylamino-2-oxo-1,2-dihydro-pyridyl]acetyl-L-argininal,

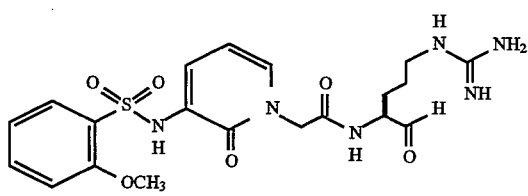

[3-(2-methoxyphenyl)sulfonylamino-2-oxo-1,2-dihydro-pyridyl]acetyl-L-argininal,

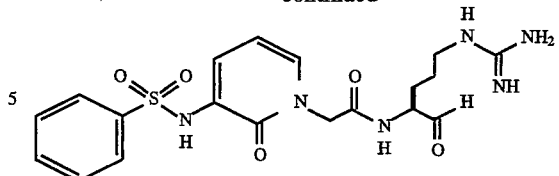

[3-(3-methoxyphenyl)sulfonylamino-2-oxo-1,2-dihydro-pyridyl]acetyl-L-argininal,

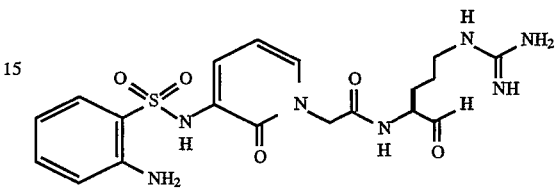

[3-(2-aminophenyl)sulfonylamino-2-oxo-1,2-dihydro-pyridyl]acetyl-L-argininal.

Example 91

Preparation of t-butyl[(t-butyl 3-carboxyacetate)-6-methyl-2-oxo-1,2-dihydro-1-pyridyl]acetate

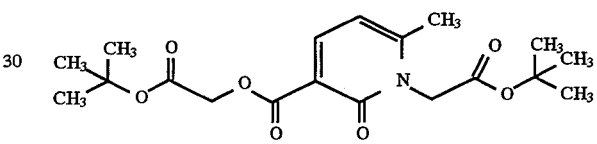

To a stirred solution of 2-hydroxy-6-methylpyridine-3-carboxylic acid (12.00 g, 78 mmole) in dimethylformamide (180 ml) was added potassium carbonate (22.8 g, 165 mmole) and t-butyl bromoacetate (24.2 mL, 165 mmole). After stirring for 36 h, the reaction mixture was diluted with water (700 mL) and extracted with ethyl acetate (2×200 mL). The combined organic extracts were washed with brine and dried over magnesium sulfate. The solvent was removed in vacuo. The residue was suction chromatographed through flash silica gel using 10–50% ethyl acetate/hexanes to yield 22.46 g (75%) of the title compound as an oil. Rf=0.10 (silica gel, 33% ethyl acetate/hexanes).

Example 92

Preparation of t-butyl(3-carboxy-6-methyl-2-oxo-1,2-dihydro-1-pyridyl)acetate

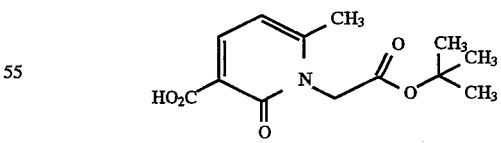

To a stirred solution of the compound of Example 91 (22.46 g, 59 mmole) in tetrahydrofuran (270 mL) was added 1.0M lithium hydroxide (90 mL, 90 mmole). After 2 hours, the solution was concentrated. The solution was diluted with water (150 mL) and extracted with diethyl ether. The aqueous layer was acidified to pH 3 with 1M sodium bisulfate, and extracted with ethyl acetate twice. The combined extracts were washed with brine, dried over magnesium sulfate and the solvent was removed in vacuo. The title compound was isolated (18.02 g) in quantitative yield.

Example 93

Preparation of t-butyl(3-benzyloxycarbonylamino-6-methyl-2-oxo-1,2-dihydro-1-pyridyl)acetate

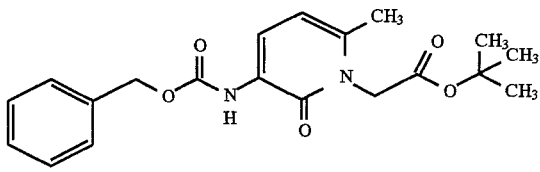

To the compound of Example 92 (13.0 g, 48.7 mmole) suspended in dioxane (150 ml), was added triethylamine (7.7 mL, 55 mmole) dropwise rapidly with stirring followed by diphenylphosphoryl azide (16 mL, 73 mmole). The suspension was heated for 2 h using a preheated 110° C. oil bath. Benzyl alcohol (7.6 g, 73 mmole) was then added and the mixture was stirred at 110° C. for 20 hours. The reaction mixture was cooled and concentrated. The residue was suspended in ethyl acetate (400 mL) and was washed with 3% HCl, then brine, dried over magnesium sulfate and concentrated. The crude product was chromatographed on flash silica gel using 20–67% ethyl acetate/hexanes to afford the title compound (14.2 g, 78% yield) as a white solid. Rf=0.53 (silica gel, 33% ethyl acetate/hexanes).

Example 94

Preparation of t-butyl(3-amino-6-methyl-2-oxo-1,2-dihydro-1-pyridyl)acetate

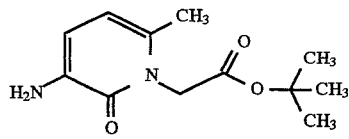

Using similar procedures to that described in Example 106 herein, the title compound (0.89 g) was prepared from the compound of Example 93 (1.7 g) in 82% yield. Rf=0.69 (silica gel, 10% methanol/dichloromethane).

Example 95

Preparation of t-butyl(3-benzylsufonylamino-6-methyl-2-oxo-1,2-dihydro-1-pyridyl)acetate

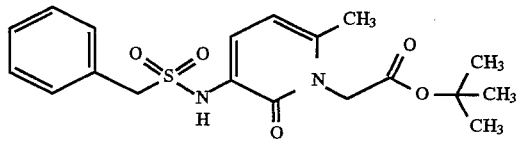

Collidine (0.59 mL, 4.5 mmole) was added in one portion to a stirred solution of the compound of Example 94 (0.89 g, 3.7 mmole) and benzylsulfonyl chloride (0.86 g, 4.5 mmole) in acetonitrile (20 ml) cooled in an ice bath. The solution was stirred for 5 minutes at 0° C., followed by 45 min at room temperature. The reaction mixture was quenched with water, then diluted with ethyl acetate (100 mL), washed with 3% HCl (until aqueous layer is pH 1), and brine, dried over magnesium sulfate, and the solvent was removed. The residue was dissolved in methanol, concentrated to a volume of approximately 3 mL, and the product was precipitated with the addition of diethyl ether. The precipitate was filtered to give 0.67 g of the title compound. The filtrate was concentrated and chromatographed on flash silica gel using 20–67% ethyl acetate hexanes as eluent. An additional 0.20 g of the title compound was recovered. A total of 0.87 g of the title compound (59% yield) was recovered. Rf=0.29 (silica gel, 33% ethyl acetate/hexanes).

Example 96

Preparation of (3-benzylsulfonylamino-6-methyl-2-oxo-1,2-dihydro-1-pyridyl)acetic acid

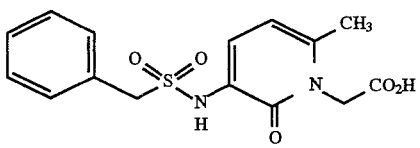

To a cooled (0° C.) solution of the compound of example 95 (0.87 g, 2.2 mmole) in dichloromethane (10 mL) was added trifluororacetic acid (10 mL). After stirring for 30 min, the ice bath was removed and the solution stirred for 2.5 hours at room temperature. The reaction mixture was concentrated. The resulting solid was triturated with diethyl ether (15 mL) and dried in vacuo. The title compound (0.73 g) was isolated in 98% yield. Rf=0.13 (silica gel, 10% methanol/dichloromethane).

Example 97

Preparation of 2-hydroxy-6-ethylpyridine-3-carbonitrile

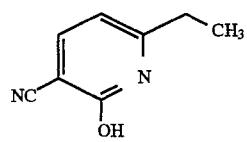

To a suspension of 1-hydroxy-6-methylpyridine-3-carbonitrile (12.24 g, 0.91 mole) in tetrahydrofuran (100 mL) cooled to –78° C. under a nitrogen atmosphere was added dropwise lithium diisopropylamide (100 mL of a 2.0M solution in heptane/tetrahydrofuran/ethylbenzene, 0.20 mole). After the addition was complete, the solution was stirred in an ice bath for 2 hours. Iodomethane (6.25 mL, 0.10 mmol) was added, and the reaction mixture was stirred for an additional 2.5 hours at 0° C. and 30 minutes at room temperature. Water (300 mL) and 1.0N NaOH 50 mL) were added. The aqueous solution was washed with ethyl acetate (150 mL), acidified with 1.0N sodium bisulfate to pH 4, and extracted with 10% methanol/ethyl acetate twice (500 mL total). Sodium chloride was added to the aqueous layer, and the solution was extracted with 10% isopropanol/ethyl acetate twice (500 mL total). The combined organic layers were washed with brine, dried over magnesium sulfate and the solvent removed under reduced pressure. The residue was recrystallized from methanol/isopropanol to give the title compound (7.56 g) as orange needles in 56% yield.

Rf=0.26 (silica gel, 10% isopropanol/chloroform). m.p. 235°–240° C. (decomp).

Example 98

Preparation of 2-hydroxy-6-ethylpyridine-3-carboxylic acid

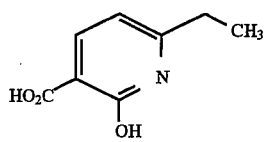

The compound of Example 97 (7.56 g, 51 mmole) was refluxed in 50% sulfuric acid (50 mL) for 3 h. The reaction mixture was cooled, and poured into water (250 mL). The solution was allowed to stand at 4° C. for 16 hours. The solid was filtered, washed with water and air dried to afford the title compound (6.03 g) in 71% yield as a tan solid. m.p. 190.5°–193° C.

Example 99

Preparation of 3-benzyloxycarbonylamino-6-ethyl-2-oxo-1,2-dihydro-1-pyridine

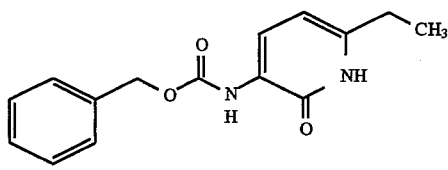

Using similar procedures to that described above in Example 93, the title compound (0.74 g) was prepared from the compound of Example 98 (1.00 g) in 45% yield. Rf=0.18 (silica gel, 20% ethyl acetate/dichloromethane). m.p. 153.5°–154° C.

Example 100

Preparation of t-butyl(3-benzyloxycarbonylamino-6-ethyl-2-oxo-1,2-dihydro-1-pyridyl)acetate

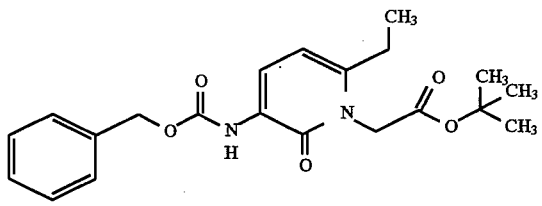

To a solution of the compound of Example 99 (150 mg, 0.55 mmole) in tetrahydrofuran (2 mL) was added lithium hexamethyldisilazide (0.61 mL of a 1.0M solution in tetrahydrofuran, 0.61 mmole). After 1.5 hours, t-butyl bromoacetetate (0.089 mL, 0.61 mmole) was added. The reaction mixture was stirred for 16 hours, then diluted with water (5 mL) and saturated ammonium chloride (5 mL), and extracted with ethyl acetate (3×5 mL). The combined organic layers were washed with brine, dried over magnesium sulfate and the solvent was reduced. Hexanes (10 mL) were added, and the solvent was removed in vacuo to afford 0.20 g of the title compound as a white solid in 94% yield. Rf=0.76 (silica gel, 20% ethyl acetate/dichloromethane).

Example 101

Preparation of (3-benzylsulfonylamino-6-ethyl-2-oxo-1,2-dihydro-1-pyridyl)acetic acid Following the three step protocol outlined in Examples 94–96, the intermediate of Example 100 is used to synthesize the following compound of the present invention.

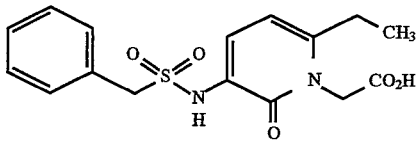

Example 102

Ethyl 2-methyl-pyrimidin-6(1H)-one-5-carboxylate

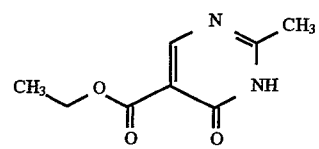

Acetamidine acetate (37.21 g, 0.31 mole) and diethyl ethoxymethylenemalonate (63 mL, 0.31 mole) were refluxed for 4 h in ethanol (60 mL). The reaction mixture was allowed to cool for 15 min., then acetamidine acetate (37.21 g, 0.31 mole) was added. The reaction mixture was refluxed for 22 hours, allowed to cool to room temperature, and diluted with water (200 mL) and dichloromethane (200 mL). The aqueous layer was extracted with 10% isopropanol/dichloromethane (2×200 mL). The combined organic extracts were washed with water (50 mL), brine (50 mL), dried over magnesium sulfate, filtered and the solvent was removed. The residue was recrystallized from chloroform/hexanes in two crops to afford the title compound (24.92 g) in 46% yield as yellowish crystals. $R_f$=0.27 (silica gel, 10% isopropanol in dichloromethane). m.p. 187°–188° C.

Example 103

Preparation of Ethyl 3-(t-butyl acetyl)-2-methyl-pyrimidin-6(1H)-one-5-carboxylate

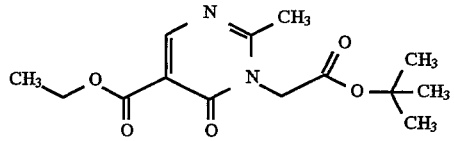

Tetra-n-butylammonium fluoride(27.4 mL of a 1.0M solution in tetrahydrofuran, 27.4 mmole) was diluted with hexanes (30 mL), the solvent was removed under reduced pressure, and the white crystals were taken up in dimethoxyethane (50 mL). t-Butyl bromoacetate (3.0 mL, 20.1 mmole) was added while stirring, followed by the compound of Example 102 (24.86 g, 136 mmole). The mixture was stirred under a nitrogen atmospherre for 1.5 hours at room temperature. The reaction mixture was diluted with water (100 mL), and extracted with ethyl acetate (3×50 mL). The combined organic extracts were washed with water, then brine (20 mL each), dried over magnesium sulfate, and the solvent was removed. The residue was purified through flash silica gel using 50% ethyl acetate, then ethyl acetate as eluent. The title compound was isolated to yield 1.81 g (45%). $R_f$=0.24 (silica gel, 20% ethyl acetate in dichloromethane).

Example 104

Preparation of 3-(t-butyl acetyl)-2-methyl-pyrimidin-6(1H)-one-5-carboxylic acid

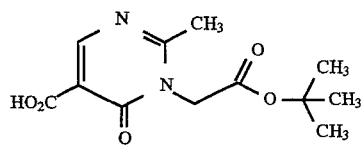

To the compound of Example 103 (10.16 g, 0.034 mole), suspended in methanol (70 ml) and cooled in an ice bath, 1.0N lithium hydroxide (38 mL, 0.038 mole) was added dropwise rapidly with stirring. The ice bath was removed. After 2 h, reaction mixture was neutralized to pH 7 with 1.0N hydrochloric acid. The solvent was reduced under vacuum, the residue diluted with water (50 mL) and washed with ethyl acetate (2–25 mL) The aqueous layer was acidified with 2.3N HCl to pH 1, extracted with ethyl acetate (50 mL), followed by dichloromethane twice (30 mL total). The combined organic extracts are washed with brine (3×10 mL). The solvent was dried over magnesium sulfate, and removed in vacuo The residue was recrystallized from ethyl acetate/diethyl ether (first crop) and ethyl acetate/diethyl ether/hexanes (second crop) to afford 4.37 g (48%) of the title compound. $R_f$=0.31 (silica gel, 1% acetic acid/10% isopropanol in chloroform).

Example 105

Preparation of t-butyl 2-methyl-5-benzyloxycarbonylamino-6-oxo-1,6-dihydro-1-pyrimidinylacetate

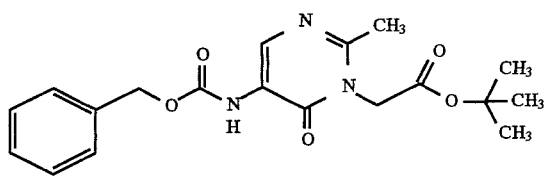

To the compound of Example 104 (4.20 g, 0.0157 mole) suspended in dioxane (50 ml), was added triethylamine (4.4 mL, 0.0313 mole) dropwise rapidly with stirring followed by diphenylphosphoryl azide (3.7 mL, 0.0172 mole). The suspension was heated for 2 h using a preheated 100° C. oil bath. Benzyl alcohol (3.2 g, 0.0313 mole) was then added and the mixture was stirred at 100° C. overnight. The reaction mixture was cooled and concentrated. The residue was suspended in ethyl acetate (100 mL) and was washed with saturated ammonium chloride, 1.0N NaOH, water (twice) and brine. The extract was dried over magnesium sulfate and concentrated. The crude product was chromatographed on flash silica gel using 10–25% ethyl acetate/dichloromethane to give the title compound (3.07 g, 53% yield) as a light yellow solid. $R_f$=0.24 (silica gel, 20% ethyl acetate in dichloromethane).

Example 106

Preparation of t-butyl 2-methyl-5-amino-6-oxo-1,6-dihydro-1-pyrimidinylacetate

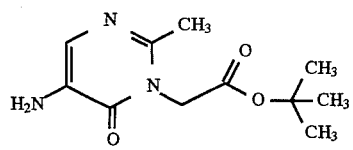

The compound of Example 105 (1.50 g, 4.0 mmol) was hydrogenated over 10% palladium on carbon (0.16 g) in ethanol (30 mL) at balloon pressure overnight. Celite was added, and the solution was filtered. The solvent was reduced. Hexanes were added and the solvent was removed in vacuo to afford 0.97 g (quantitative yield) of the title compound as a white solid.

$R_f$=0.24 (silica gel, 10% isopropanol in chloroform).

Example 107

Preparation of t-butyl 2-methyl-5-benzylcarbonyloxyamino-6-oxo-1,6-dihydro-1-pyrimidinylacetate

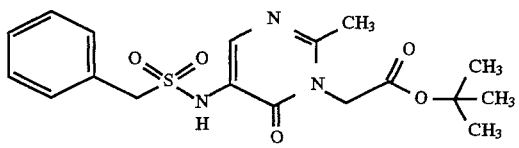

Benzylsulfonyl chloride (1.06 g, 5.6 mmole) was added in one portion to a stirred solution of the compound of example 106 (0.89 g, 3.7 mmole) and 4-methylmorpholine (1.47 mL, 11.2 mmole) in tetrahydrofuran (10 ml). The solution was stirred for 2 hours. The reaction mixture was concentrated, then diluted with ethyl acetate (100 mL), washed with 1.0N HCl (until aqueous layer is pH 1), water, saturated sodium bicarbonate and brine. The organic layer was dried over magnesium sulfate, and the solvent was removed. The residue was recrystallized from ethyl acetate (first crop) and ethyl acetate/ether/hexanes (second crop). The second crop was treated with 1.0M potassium carbonate (3 mL) and methanol(10 mL) for 2 hours. The solution became homogeneous. The reaction mixture was acidified to pH 7 with 1.0N HCl. The solvent was reduced, and the aqueous solution was extracted with ethyl acetate three times. The combined organic extracts were washed with brine, dried over magnesium sulfate and the solvent was removed in vacuo. In a similar fashion the first crop was treated with 1.0M potassium carbonate and methanol. A total of 1.20 g of the title compound (82% yield) was recovered as a white solid.

$R_f$=0.26 (silica gel, 20% ethyl acetate in dichloromethane).

Example 108

Preparation of 2-methyl-5-benzylsulfonylamino-6-oxo-1,6-dihydro-1-pyrimidinylacetic acid

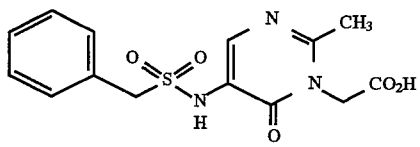

To the compound of Example 107 (1.15 g, 2.9 mmole) was treated with 50% trifluoroacetic acid/dichloromethane (10 mL). After 1 hour, the reaction mixture was concentrated, then diluted with diethyl ether (100 mL). The solution was allowed to stand overnight, then the solvent was removed under reduced pressure. The residue was partitioned between saturated sodium bicarbonate (25 mL) and ethyl acetate (10 mL). The aqueous layer was washed with ethyl acetate, then acidified with 2.3M HCl to pH 1. The preciptiate was filtered, washed with water and dried under vacuum to give the title compound (0.75 g, 76% yield) as a white solid. m.p. 244°–246° C. (decomp.).

Example 109

Preparation of 5-nitro-1-methyl-uracil

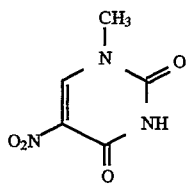

5-nitrouracil (10.00 g, 64 mmole) and potassium carbonate were stirred in dimethylformamide (50 mL) for 15 min. A solid formed. Iodomethane (5.3 mL, 85 mmol) was added and the flask was shaken until the solid dissolved. After the reaction mixture was stirred for 30 min., 2% NaOH (w/v) (200 mL) was added, followed by water (100 mL). The solution was washed with ethyl acetate (100 mL), and the aqueous layer was acidified to pH 3 with 1.0N HCl. A precipitate formed as the pH was lowered. After allowing the heterogeneous solution to stand for 16 hours, the product was filtered, washing with water, and air dried. The title compound was isolated in 77% yield as a yellow powder. m.p. 249°–250° C.

Example 110

Preparation of t-butyl(5-nitro-1-methyl-uracilyl)acetate

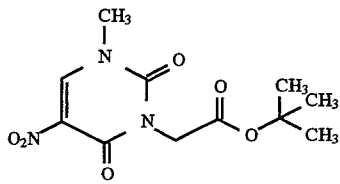

Sodium hydride (0.51 g of a 60% dispersion in mineral oil, 13 mmol) was washed with pentane three times (4 mL each). The compound of Example 109 (2.00 g, 12 mmole) was added portionwise. After the addition was complete, the reaction mixture was stirred for 30 minutes under a nitrogen atmosphere. t-Butyl bromoacetate (1.73 g, 12 mmole) was added in one portion, and the solution was stirred for 3 hours. The reaction mixture was diluted with water (200 mL), and extracted with ethyl acetate (3×50 mL). The combined organic extracts were washed with water (3×50 mL), then brine, dried over magnesium sulfate. The solvent was concentrated, hexanes were added and the solvent was removed in vacuo to afford the title compound (1.97 g) in 59% yield. Rf=0.38 (silica gel, 20% ethyl acetate in dichloromethane.

Example 111

Preparation of Ethyl 5-(benzylsulfonylamino-1-methyl-uracilyl)acetate

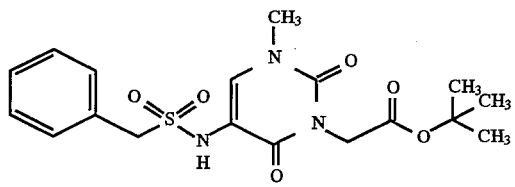

Using similar procedures to that described above in Example 6, but employing 3 equivalents of 4-methyl morpholine as base during the reaction with benzylsulfonyl chloride, the title compound was prepared from the compound of Example 110 in 48% yield. m.p. 165°–166° C.

Example 112

Preparation of 5-(benzylsulfonylamino-1-methyl-uracilyl)acetic acid

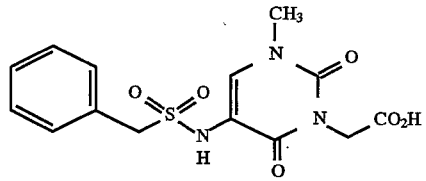

Using a similar procedure to that described above in Example 108, the title compound was prepared from the compound of Example 111 in 88% yield. m.p. 200°–201° C.

Example 113

General Procedure for Preparation of Compounds of the Present Invention

Following the three-step protocol outlined in Examples 8–10 (coupling, hydrogenation, hydrolysis) the intermediates of Examples 96, 108 and 112 were used to synthesize the following compounds of the present invention:

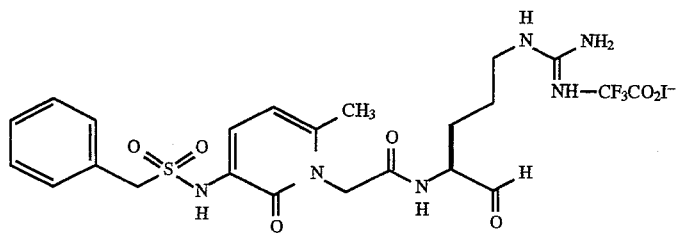

(3-benzylsulfonylamino-6-methyl-2-oxo-1,2-dihydro-1-pyridyl)acetyl-L-argininal, trifluoroacetate salt (Compound C).

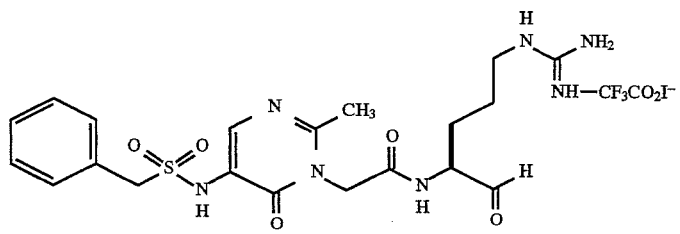

(5-benzylsulfonylamino-2-methyl-6-oxo-1,6-dihydro-1-pyrimidinyl)acetyl-L-argininal, trifluoroacetate salt (Compound D).

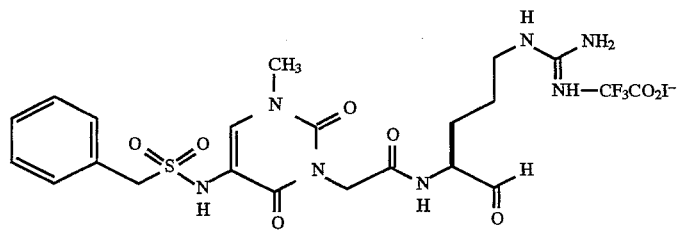

(5-benzylsulfonylamino-1-methyl-uracilyl)acetyl-L-argininal, trifluoroacetate salt (Compound E).

Example 114

Preparation of 4-(2-trimethylsiloxyphenethyl)-3-nitro-2-oxo-1,2-dihydro-1-pyridine

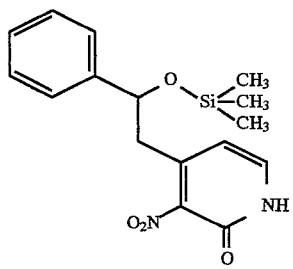

A suspension of 4-methyl-3-nitro-2-pyridone (3.08 g, 20 mmole) in tetrahydrofuran (50 mL) was cooled to 0° C. Lithium hexamethyldisilazide (21 mL of a 1M solution in tetrahydrofuran, 21 mmole) was added to the reaction over 15 minutes. After stirring for 45 minutes, trimethylsilyl chloride (2.7 mL, 21 mmole) was added. After an hour, another portion of lithium hexamethyldisilazide (21 mL of a 1M solution in tetrahydrofuran, 21 mmole) was added to the solution. After 30 minutes, freshly distilled benzaldehyde (2.1 mL, 21 mmole) was added. The reaction was allowed to warm to room temperature and after 18 hours, it was quenched with aqueous ammonium chloride (20 ml), extracted with ethyl acetate (150 ml), washed with brine (50 ml), and dried over magnesium sulfate. The product was purified by chromatography with silica gel, eluting with 2–10% methanol/dichloromethane. Recrystallization from toluene yielded 0.79 g (8.5%) of the title compound. $R_f$=0.25 (silica gel, 50% ethyl acetate/hexanes).

Example 115

Preparation of Ethyl[4-(2-trimethylsiloxyphenethyl)-3-nitro-2-oxo-1,2-dihydro-1-pyridyl]acetate

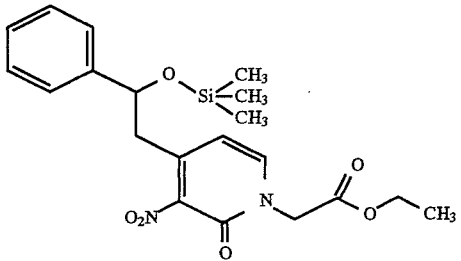

To a solution of the compound of Example 1 (0.79 g, 2.4 mmole) in tetrahydrofuran at 0° C. was added lithium hexamethyldisilazide (2.5 mL of a 1M in tetrahydrofuran. 2.5 mmole) over 5 minutes. After 30 minutes, ethyl bromoacetate (0.28 mL, 2.5 mmole) was added. The reaction was allowed to warm to room temperature and after 8 hours, it was quenched with aqueous ammonium chloride (5 mL), extracted with ethyl acetate (75 mL), washed with brine (30 mL), and dried over magnesium sulfate. The product was purified by chromotography with silica gel, eluting with (33%) ethyl acetate/hexanes to yield 0.76 g of the title compound (81% yield). $R_f$=0.45 (silica gel, 50% ethyl acetate/hexanes).

Example 116

Preparation of [3-acetamido-4-(2-hydroxyphenethyl)-2-oxo-1,2-dihydro-1-pyridyl]acetic acid

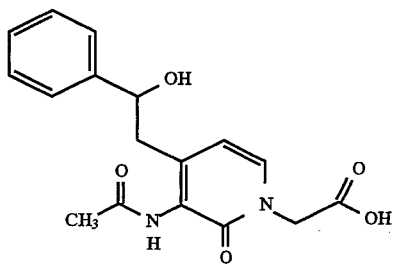

The compound of Example 2 (760 mg, 1.82 mmole) was dissolved in ethyl acetate (10 mL). Acetic anhydride (0.69 mL, 7.3 mmole) and 10% palladium on carbon (75 mg) were added and the reaction was stirred under a hydrogen balloon for 18 hours. The reaction was then filtered through celite and concentrated. The residue was dissolved in tetrahydrofuran (7.0 mL) and 1.0M lithium hydroxide was added (3.6 mL, 3.6 mmole). The reaction was stirred for 22 hours at which time additional 1.0M lithium hydroxide (2.0 mL, 2.0 mmole) and methanol (2.0 mL) were added. The reaction was stirred for 48 hours at room temperature, then was diluted with water (20 mL) and washed with ethyl acetate (20 mL). The aqueous layer was acidified with conc. HCl to pH~3, and the product was extracted into ethyl acetate (50 mL), washed with brine (40 mL), and dried over magnesium sulfate. Back extraction of the aqueous layer with 30% isopropanol/dichloromethane yielded a total of 440 mg (96%) of the title compound. $^1$H NMR (CD$_3$OD): delta 2.15 (3H, s), 2.81–2.94 (2H, m), 4.70 (2H, s), 4.9 (1H, dd, J=5.3, 8.2 Hz), 6.3 (1H, d, J=7.1 Hz), 7.22–7.36 (5H, m), 1.73 (1H, d, J=7.1 Hz).

Example 117

General Procedure for Preparation of Compounds of the Present Invention

Following the three-step protocol outlined in Examples 8–10 (coupling, hydrogenation, hydrolysis) the intermediates of Examples 101 and 116 are used to synthesize the following compounds of the present invention:

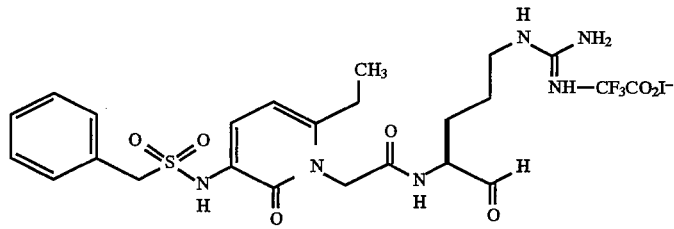

(3-benzylsulfonylamino-6-ethyl-2-oxo-1, 2-dihydro-1-pyridyl) acetyl-L-argininal, trifluroacetate salt.

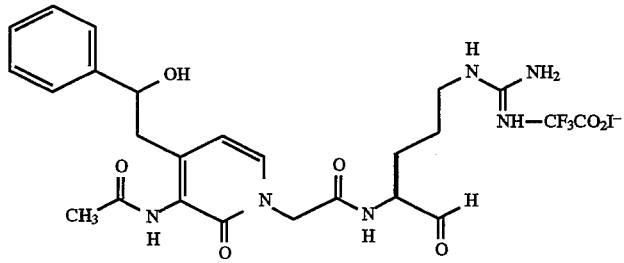

[3-acetamido-4-(2-hydroxyphenethyl)-2-oxo-1, 2-dihydro-1-pyridyl]acetyl-L-argininal, trifluoroacetate salt.

Example 118

(5-chloro-2-methoxy-phenylsulfonyl-3-amino-2-oxo-1,2-dihydropyridyl)acetyl-L-N$^g$-nitro-argininal-ethyl cyclol

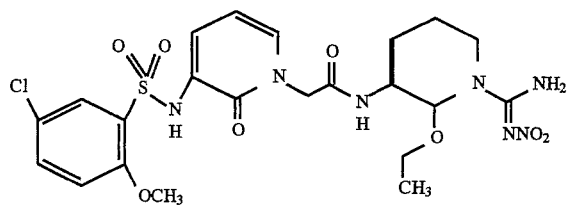

Following the two-step protocol outlined in Examples 7–8 (hydrolysis, coupling), the title compound is prepared from an intermediate of Example 89, ethyl(2-methoxy-5-chloro-benzenesulfonyl-3-amino-2-oxo-1,2-dihydropyridyl)acetate.

Example 119

Preparation of (5-chloro-2-methoxy-phenylsulfonyl-3-amino-2-oxo-1,2-dihydropyridyl)acetyl-L-Argininal, trifluoroacetate salt

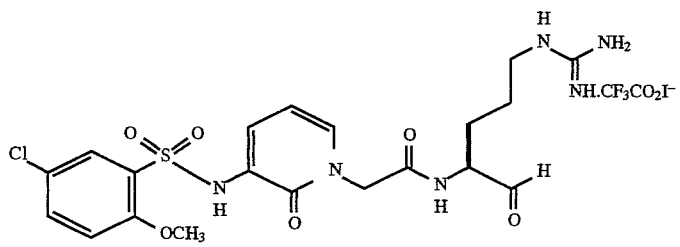

To a stirred solution of the compound of Example 118 (280 mg, 0.47 mmol) in ethyl alcohol (5 mL), a mixture of freshly made 20% titanium(III) chloride solution in water (3.7 mL, 4.7 mmol) and 4.0M ammonium acetate buffer, pH 5.0 (7.4 mL) was added. The reaction mixture was stirred at room temperature. After the reaction was complete (30–45 min.), the excess of titanium(III) chloride was oxidized by bubbling the air through the reaction mixture (30 min.). The solvent was removed in vacuo. The residual was taken into water (50 mL) and then centrifuged at 3,000 rpm for 10 minutes. The supernatant was decanted, and the solid was washed with water (30 mL) and centrifuged. The combined supernatants were concentrated to 25 mL. The solution was cooled down to 0° C. with ice bath. 12N hydrochloric acid (25 mL) was added, and the ice bath was removed. The reaction mixture was stirred at room temperature. After the reaction was complete (30–45 minutes), the reaction mixture was quenched with water (150 mL) and sodium acetate (40 g), and then filtered. The aqueous solution was purified by reverse phase HPLC with C-18 column using a gradient system of 17–35% acetonitrile in water with 0.1% of trifluoroacetic acid over 30 min. to afford 160 mg of the title compound (160 mg, 0.31 mmol). MS: 513 (M+H$^+$).

Example A

Kinetic analysis of [3-[(benzylsulfonyl)amino]-2-oxo-1,2-dihydropyridyl]acetyl-L-argininal in an in vitro thrombin inhibition assay The ability of a compound of a present invention, [3-[(benzylsulfonyl)amino]-2-oxo-1,2-dihydropyridyl]acetyl-L-argininal (Example 10), to act as an inhibitor of thrombin catalytic activity was assessed by determining its inhibition constant, Ki.

Enzyme activity was determined using the chromogenic substrate Pefachrome t-PA ($CH_3SO_2$-D-hexahydrotyrosine-glycyl-L-Arginine-p-nitroaniline), obtained from Pentapharm Ltd. The substrate was reconstituted in deionized water prior to use. Purified human alpha-thrombin (3000 U/mg specific activity) was obtained from Enzyme Research Laboratories, Inc. The buffer used for all assays was HBSA (10 mM HEPES, pH 7.5, 150 mM sodium chloride, 0.1% bovine serum albumin).

The assay for Ki determinations was conducted by combining in appropriate wells of a Corning microtiter plate, 50 microliters of HBSA, 50 microliters of the test compound at a specified concentration diluted in HBSA (or EBSA alone for $V_o$ (uninhibited velocity) measurement), and 50 microliters of the chromogenic substrate (250 micromolar, 5-times Km). At time zero, 50 microliters of alpha-thrombin diluted in HBSA, was added to the wells yielding a final concentration of 0.5 nM in a total volume of 200 microliters. Velocities of chromogenic substrate hydrolysis which occurred over 40 minutes was measured by the change in absorbance at 405 nm using a Thermo Max® Kinetic Microplate Reader. Ki values were determined for test compounds using the relationships developed by Williams and Morrison, Methods in Enzymology, 63:437 (1979) using steady state velocities (Vs) measured over 40 minutes. The extent of substrate hydrolysis was less than 5% over the course of this assay.

Table 1 below gives the Ki values for [3-[(benzylsulfonyl)amino]-2-oxo-1,2-dihydropyridyl]acetyl-L-argininal. The data shows the utility of this compound as potent in vitro inhibitors of human alpha-thrombin.

TABLE 1

Inhibitor constant of [3-[(benzylsulfonyl)amino]-2-oxo-1,2-dihydropyridyl]acetyl-L-argininal against human alpha-thrombin amidolytic activity.

| Compound | Ki (pM) |
|---|---|
| [3-[(benzylsulfonyl)amino]-2-oxo-1,2-dihydropyridyl]acetyl-L-argininal | 289 ± 32 |

Example B

In vitro enzyme Assays for specificity determination

The ability of compounds of the present invention to act as a selective inhibitor of thrombin catalytic activity was assessed by determining the concentration of compound which inhibited the activity of this enzyme by 50%, ($IC_{50}$), and comparing this value to that determined for all or some of the following related serine proteases: recombinant tissue plasminogen activator (rt-PA), plasmin, activated protein C, chymotrypsin, factor Xa and trypsin.

The buffer used for all assays was HBSA (10 mM HEPES, pH 7.5, 150 mM sodium chloride, 0.1% bovine serum albumin).

The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_o$ (uninhibited velocity) measurement), and 50 microliters of the enzyme diluted in HBSA. Following a 30 minute incubation at ambient temperature, 50 microliters of the substrate at the concentrations specified below, was added to the wells yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Thrombin (fIIa) Assay.

Enzyme activity was determined using the chromogenic substrate, Pefachrome t-PA ($CH_3SO_2$-D-hexahydrotyrosine-glycyl-L-Arginine-p-nitroaniline, obtained from Pentapharm Ltd.). The substrate was reconstituted in deionized water prior to use. Purified human a-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 mL), a-thrombin (50 µl) and inhibitor (50 µl) (covering a broad concentration range), were combined in appropriate wells and incubated for 30 minutes at room temperature prior to the addition of substrate Pefachrome-t-PA (50 µl). The initial velocity of Pefachrome t-PA hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Factor Xa

Factor Xa catalytic activity was determined using the chromogenic substrate S-2765 (N-benzyloxycarbonyl-D-arginine-L-glycine-L-arginine-p-nitroaniline), obtained from Kabi Pharmacia Hepar, Inc. (Franklin, Ohio). All substrates were reconstituted in deionized water prior to use. The final concentration of S-2765 was 250 µM (about 5-times Km). Purified human Factor X was obtained from Enzyme Research Laboratories, inc. (South Bend, Ind.) and Factor Xa (FXa) was activated and prepared from it as described [Bock, P. E., Craig, P. A., Olson, S. T., and Singh, P. Arch. Biochem. Biophys. 273:375–388 (1989)].

Recombinant tissue plasminogen activator (rt-PA) Assay.

rt-PA catalytic activity was determined using the substrate, Pefachrome t-PA ($CH_3SO_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay.

Plasmin catalytic activity was determined using the chromogenic substrate, S-2251 [D-valyl-L-leucyl-L-lysine-p-nitroanilide dihydrochloride], which was obtained from Kabi Diagnostica. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay.

aPC catalytic activity was determined using the chromogenic substrate, Pefachrome PC (delta-carbobenzloxy-D-lysine-L-prolyl-L-arginine-p-nitroaniline dihydrochloride), obtained from Pentapharm Ltd.). The substrate was made up in deionized water followed by dilution in HBSA prior to the assay in which the final concentration was 250 micromolar (about 3-times Km). Purified human aPC was obtained from Hematologic Technologies, Inc. The enzyme was diluted into HBSA prior to assay in which the final concentration was 1.0 nM.

Chymostrypsin Assay.

Chymotrypsin catalytic activity was determined using the chromogenic substrate, S-2586 (methoxy-succinyl-L-arginine-L-prolyl-L-tyrosyl-p-nitroanilide), which was obtained from Kabi Diagnostica. The substrate was made up in deionized water followed by dilution in HBSA prior to the assay in which the final concentration was 100 micromolar (about 9-times Km). Purified (3X-crystallized; CDI) bovine pancreatic alpha-chymotrypsin was obtained from Worthington Biochemical Corp. The enzyme was reconstituted in deionized water and diluted into HBSA prior to assay in which the final concentration was 1.0 nM.

Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from Kabi Diagnostica. The substrate was made up in deionized water followed by dilution in HBSA prior to the assay in which the final concentration was 250 micromolar (about 4-times Km). Purified (3X-crystallized; TRL3) bovine pancreatic trypsin was obtained from Worthington Biochemical Corp. The enzyme was reconstituted in deionized water and diluted into HBSA prior to assay in which the final concentration was 0.5 nM.

Tables 2 and 3 list the determined $IC_{50}$ values for certain of the enzymes listed above and demonstrate the high degree of specificity for the inhibition of alpha-thrombin compared to these related serine proteases.

TABLE 2

$IC_{50}$ values (nM) for the inhibition of human alpha thrombin amidolytic activity compared to selected serine proteases for compounds of Example 10 (column A), Example 90, compound B (column B), and Example 113, compounds C, D, and E (columns C, D, and E, respectively)

| Enzyme | A | B | C | D | E |
|---|---|---|---|---|---|
| Alpha-thrombin | 0.66 | 0.98 | 0.467 | 2.32 | 141 |
| rt-PA | NI* | NI* | ND | NI* | NI* |
| Plasmin | NI* | NI* | NI* | NI* | NI* |
| aPC | NI* | NI* | ND | NI* | NI* |

*-$IC_{50}$ value > 2500 nM.
ND - not determined

TABLE 3

IC$_{50}$ values (nM) for inhibition of human alpha thrombin amidolytic activity compared to inhibition of rt-PA, plasmin, and aPC for compounds made according to Examples 89 and 90 with the stated R$_1$ substitution

| R$_1$ substitution | Thrombin (IC$_{50}$) | rt-PA (IC$_{50}$) | Plasmin (IC$_{50}$) | aPC (IC$_{50}$) |
|---|---|---|---|---|
| 2-CF$_3$-phenyl | 5.6 | NI* | NI* | NI* |
| 3-CF$_3$-phenyl | 3.1 | NI* | NI* | NI* |
| 2-Me-phenyl | 1.4 | NI* | NI* | NI* |
| 3-Me-phenyl | 0.85 | NI* | NI* | NI* |
| 2-Me,5-F-phenyl | 1.97 | NI* | NI* | NI* |
| 2-OMe-phenyl | 1.98 | NI* | NI* | NI* |
| 3-OMe-phenyl | 0.65 | NI* | NI* | NI* |
| 2-OMe,5-Cl-phenyl | 1.16 | NI* | NI* | NI* |
| 2-NH$_2$-phenyl | 3.7 | NI* | NI* | NI* |

Example C

Ex vivo anticoagulant effects of [3-[(benzylsulfonyl)amino]-2-oxo-1,2-dihydropyridyl] acetyl-L-argininal in human plasma The ex vivo anticoagulant effect of [3-[(benzylsulfonyl)amino]-2-oxo-1,2-dihydropyridyl]acetyl-L-argininal was determined by measuring the prolongation of the activated partial thromboplastin time (APTT) over a broad concentration range of the added inhibitor, using pooled normal human plasma. Fresh frozen citrated pooled normal human plasma was obtained from George King Biomedical, Overland Park, Kans. Measurements APTT was made using the Coag-A-Mate RA4 automated coagulometer (General Diagnostics, Organon Technica, Oklahoma City, Okla.) using the Platelin® L reagent (Organon Technica, Durham, N.C.) as the initiator of clotting according to the manufacturers instructions. The assay was conducted by making a series of dilutions of the test compounds in rapidly thawed plasma followed by adding 200 microliters to the wells of the assay carousel. As shown in FIG. 5, a compound of the present invention, [3-[(benzylsulfonyl)amino]-2-oxo-1,2-dihydropyridyl]acetyl-L-argininal, prolonged the APTT in a dose dependent manner in human plasma demonstrating an anticoagulant effect in this species of mammals.

Example D

Evaluation of the antithrombotic potential of [3-[(benzylsulfonyl)amino]-2-oxo-1,2-dihydropyridyl] acetyl-L-argininal in an experimental rat model of thrombosis The demonstrated anticoagulant effects of a compound of the present invention, [3-[(benzylsulfonyl)amino]-2-oxo-1,2-dihydropyridyl]acetyl-L-argininal, in human citrated plasma indicated that this compound may have potent antithrombotic effects in an experimental model of thrombosis. To investigate this, the antithrombotic (prevention of thrombus formation) properties of this compound was evaluated using the following established experimental model of acute vascular thrombosis.

Rat model of FeCl$_3$-induced platelet-dependent arterial thrombosis

This is a well characterized model of platelet dependent, arterial thrombosis which has been used in the evaluation potential antithrombotic compounds such as direct thrombin inhibitors. Kurz, K. D., Main, B. W., and Sandusky, G. E., Thromb. Res., 60:269–280 (1990). In this model a platelet-rich, occlusive thrombus is formed in a segment of the rat carotid artery treated locally with a fresh solution of FeCl$_3$ absorbed to a piece of filter paper. The FeCl$_3$ is thought to diffuse into the treated segment of artery and causes de-endothelialization of the affected vessel surface. This results in the exposure of blood to subendothelial structures which in turn causes platelet adherence, thrombin formation and platelet aggregation resulting in occlusive thrombus formation. The effect of a test compound on the incidence of occlusive thrombus formation following the application of the FeCl$_3$ is monitored by ultrasonic flowtometry and is used as the primary end point. The use of flowtometry to measure carotid artery blood flow, is a modification of the original procedure in which thermal detection of clot formation was employed. Kurz, K. D., Main, B. W., and Sandusky, G. E., Thromb. Res., 60:269–280 (1990).

Male Harlan Sprague Dawley rats (420–450 g) were acclimated at least 72 hours prior to use and fasted for 12 hours prior to surgery with free access to water. The animals were prepared, anesthetized with Nembutal followed by the insertion of catheters for blood pressure monitoring, drug and anesthesia delivery. The left carotid artery was isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals were randomized in either a control (saline) or treatment group with test compound, [3-[(benzylsulfonyl)amino]-2-oxo-1,2-dihydropyridyl] acetyl-L-argininal, with at least 6 animals per group per dose. The test compound was administered as a single intravenous bolus at the doses outlined in Table 3 after placement of the flow probe and 5 minutes prior to the thrombogenic stimulus. At t=0, a 3 mm diameter piece of filter paper (Whatman #3) soaked with 10 microliters of a 35% solution of fresh FeCl$_3$ (made up in water) was applied the segment of isolated carotid artery distal to the flow probe. Blood pressure, blood flow, heart rate, and respiration were monitored for 60 minutes.

The incidence of occlusion (defined as the attainment of zero blood flow) was recorded as the primary end point.

The efficacy of the [3-[(benzylsulfonyl)amino]-2-oxo-1, 2-dihydropyridyl]acetyl-L-argininal as an antithrombotic agent in preventing thrombus formation in this in vivo model was demonstrated by the reduction in the incidence of thrombotic occlusion as shown in Table 4 below.

TABLE 4

Results of [3-[(benzylsulfonyl)amino]-2-oxo-1,2-dihydropyridyl]acetyl-L-argininal in the FeCl$_3$ Model of Thrombosis in Rats.

| Treatment Group | Dose (mg/kg) | n | Incidence of Occlusion |
|---|---|---|---|
| Saline | — | 6 | 6/6 |
| [3-[(benzylsulfonyl)amino]-2-oxo-1,2-dihydropyridyl]acetyl -L-argininal | 0.3 | 6 | 6/6 |
| [3-[(benzylsulfonyl)amino]- | 1.0 | 6 | 3/6 |

TABLE 4-continued

Results of [3-[(benzylsulfonyl)amino]-2-oxo-
1,2-dihydropyridyl]acetyl-L-argininal in the
FeCl₃ Model of Thrombosis in Rats.

| Treatment Group | Dose (mg/kg) | n | Incidence of Occlusion |
|---|---|---|---|
| 2-oxo-1,2-dihydropyridyl]acetyl-L-argininal | | | |
| [3-[(benzylsulfonyl)amino]-2-oxo-1,2-dihydropyridyl]acetyl-L-argininal | 3.0 | 6 | 1/6* |
| [3-[(benzylsulfonyl)amino]-2-oxo-1,2-dihydropyridyl]acetyl-L-argininal | 5.0 | 6 | 0/6* |

*-p ≦ 0.05 from saline control by Fishers test

The effective dose which prevents 50% of thrombotic occlusions in this model ($ED_{50}$) can be determined from the above data by plotting the incidence of occlusion versus the dose administered. This allows a direct comparison of the antithrombotic efficacy of [3-[(benzylsulfonyl)amino]-2-oxo-1,2-dihydropyridyl]acetyl-L-argininal, with other antithrombotic agents which have also been evaluated in this model as described above. Table 5 lists the $ED_{50}$ values for several well known anticoagulant agents in this model compared to [3-[(benzylsulfonyl)amino]-2-oxo-1,2-dihydropyridyl]acetyl-L-argininal.

TABLE 5

Efficacy of [3-[(benzylsulfonyl)amino]-2-oxo-
1,2-dihydropyridyl]acetyl-L-argininal compared
to other antithrombotic agents based on $ED_{50}$ for
thrombus prevention in the FeCl₃ model of arterial

| Compound | $ED_{50}$[a] |
|---|---|
| Standard Heparin | 200 U/kg |
| Argatroban | 3.8 mg/kg |
| Hirulog ™ | 3.0 mg/kg |
| [3-[(benzylsulfonyl)amino]-2-oxo-1,2-dihydropyridyl]acetyl-L-argininal | 1.0 mg/kg |

[a]$ED_{50}$ is defined as the dose that prevents the incidence of complete thrombotic occlusion in 50% of animals tested.

The data presented in Table 4 clearly demonstrates the effectiveness of a compound of the present invention, [3-[(benzylsulfonyl)amino]-2-oxo-1,2-dihydropyridyl]acetyl-L-argininal, in preventing occlusive thrombus formation in this experimental model. The relevance of this data to preventing human thrombosis can be inferred from the comparison to the other anticoagulant agents listed in Table 5 which have been evaluated in an identical manner in this experimental model and have demonstrated antithrombotic efficacy in preventing thrombus formation clinically as described in the following literature citations: Heparin-Hirsh, J., N. Engl. J. Med., 324:1565–1574 (1992) and Cairns, J. A. et al., Chest, 102:456S–481S (1992); Argatroban-Gold, H. K. et al., J. Am. Coll. Cardiol., 21:1039–1047 (1993); and Hirulog™-Sharma, G. V. R. K. et al., Am. J. Cardiol., 72: 1357–1360 (1993) and Lidón, R. M. et al., Circulation, 88:1495–1501 (1993). The in vivo comparison of [3-[(benzylsulfonyl)amino]-2-oxo-1,2-dihydropyridyl]acetyl-L-argininal with the clinically effective antithrombotic agents, Standard Heparin, Argatroban, and Hirulog™, in the same rodent model of experimental thrombosis coupled with the demonstrated anticoagulant effects of [3-[(benzylsulfonyl)amino]-2-oxo-1,2-dihydropyridyl]acetyl-L-argininal and [3-[(phenylsulfonyl)amino]-2-oxo-1,2-dihydropyridyl]acetyl-L-argininal in human plasma described above in Example B would lead one skilled in the art to conclude that the compounds of the present invention will be an effective antithrombotic agent in humans.

Example E

Multiple Extracorporeal Shunt Model in Rats Utilizing Oral Dosing

The compound of Example 10 was evaluated in a multi-chamber A-V shunt model in rats. The A-V shunt model is one of the most common and generally used systems to evaluate antithrombotic compounds. Smith, J. R. and White, A. M. Br. J. Pharmacol., 77: 29–38 (1982). In this model a localized clot made up of primarily fibrin with some platelet and macrophage involvement (Shand, R. A. and Smith, J. R. and Wallis, R. B. Thromb. Res., 36: 223–232 (1984)), is formed on an artificial thrombogenic surface (typically a segment of silk or cotton thread) contained in a sialstic cheer which is part of an exteriorized shunt between the carotid artery and jugular vein. The procedure described in this Example is a modified A-V shunt model that allows for oral dosing of test agents and subsequent evaluation of efficacy over a two to three hour window in time.

Briefly, male Harlan Sprague Dawley rats (420–450 g) were acclimated at least 72 hours prior to use. The animals were fasted for 12 hours prior to surgery with free access to water. Unanesthetized animals were grouped into four dosage groups (six or seven animals per group) and administered test agents orally via gavage needle, at doses of 1.0, 3.0, 10 and 50 mg/kg. Immediately after oral dosing, animals were anesthetized with sodium pentobarbital (Nembutal) given intraperitoneally at a dose of 50 mg/kg body weight, and placed on a isothermal pad to maintain body temperature. The level of anesthesia was monitored every 15 minutes by neuro-response to a tail pinch, respiration and core temperature. The desired depth of surgical anesthesia was maintained by administering subsequent doses (5 mg/kg) intravenously. The left femoral artery was catheterized using standard procedures for blood pressure monitoring and blood sampling, with polyethylene tubing (PE50). The left femoral vein was catheterized with PE50 tubing for delivery of anethestic.

The exteriorized shunts were assembled by connecting two pieces of saline filled 12.5 cm PE90 tubing with a 6 cm piece of PE160 tubing containing a 6 cm piece of silk suture size 3 and clamped with hemostats. A small 0.5 cm portion of the silk thread protrudes from the junction of the chamber with the shunt. The left jugular vein and right carotid artery were catheterized with the ends of the PE90 shunt. The shunt was unclamped and blood allowed to flow from the carotid artery, through the chamber, and exits the shunt via the jugular vein. After 15 minutes, both sides of the chamber were clamped and the suture containing the clot removed following detachment of the arterial end of the chamber. The clot was immediately weighed and recorded. This procedure takes place at predetermined intervals (60, 90, 120, and 150 minutes after oral dosing) to allow assessment of efficacy over a large window in time. Four shunts were placed with flow initiated at 45, 75, 105, and 135 minutes after oral compound administration. Clot weight from the four shunts was the primary endpoint of the protocol. Blood pressure, heart rate core temperature and respiration were monitored continuously. Following termination of the experiment the animals were euthanized with a 120 mg/kg dose of Nembutal. One experiment was performed per animal.

ED$_{50}$ values were calculated at 60, 90, 120, and 150 minutes after oral dosing of test compound. ED$_{50}$ is that dose that reduced the clot size by 50%. For the compound of Example 10, the ED$_{50}$ values were as shown in Table 6, below, and demonstrate the oral availability and efficacy of the compound.

TABLE 6

| Time after oral dose | ED$_{50}$ value |
| --- | --- |
| 60 min | <1.0 mg/kg |
| 90 min | 2.9 mg/kg |
| 120 min | 2.9 mg/kg |
| 150 min | 8.2 mg/kg |

We claim:
1. A compound of formula:

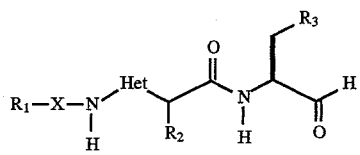

wherein
(a) X is selected from the group consisting of —S(O)$_2$—, —N(R')—S(O)$_2$—, —(C=O)—, —OC(=O)—, —NH—C(=O)—, —P(O)(R")— and a direct link, wherein R' is hydrogen, alkyl of 1 to about 4 carbon atoms, aryl of about 6 to about 14 carbon atoms or aralkyl of about 6 to about 16 carbon atoms, and R" is NR', OR', R', or SR', with the proviso that R" is not NH, OH, H, or SH, and;
(b) R$_1$ is selected from the group consisting of:
(1) alkyl of 1 to about 12 carbon atoms,
(2) alkyl of 1 to about 3 carbon atoms substituted with cyclic alkyl of about 5 to about 8 carbon atoms, which optionally is substituted in the ring carbons with hydroxyl, amino, guanidino, amidino, or alkoxyl or alkyl each of 1 to about 3 carbons,
(3) cyclic alkyl of 3 to about 15 carbon atoms, which optionally is substituted in the ring carbons with hydroxyl, amino, guanidino, amidino, or alkoxyl or alkyl each of 1 to about 3 carbons,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, optionally substituted in the ring carbons with hydroxyl, alkoxyl or alkyl of 1 to about 3 carbons, amino, guanidino, or amidino,
(5) heterocyclo of 4 to about 10 ring atoms with the ring atoms selected from carbon and heteroatoms, wherein the heteroatoms are selected from the group consisting of oxygen, nitrogen, and S(O)$_i$, wherein i is 0, 1 or 2, optionally substituted in the ring carbons with hydroxyl, alkoxyl or alkyl each of 1 to about 3 carbons, amino, guanidino, or amidino,
(6) alkenyl of about 3 to about 6 carbon atoms which is optionally substituted with cyclic alkyl of about 5 to about 8 carbon atoms, which optionally is substituted in the ring carbons with hydroxyl, amino, guanidino, amidino, or alkoxyl or alkyl each of 1 to about 3 carbons, (7) aryl of about 6 to about 14 carbon atoms which is optionally mono-, di- or tri-substituted with Y$_1$, Y$_2$, and/or Y$_3$, respectively,
(8) heteroaryl of 5 to 14 atoms with the ring atoms selected from carbon and heteroatoms, wherein the heteroatoms are selected from oxygen, nitrogen, and S(O)$_i$, wherein i is 0, 1 or 2, optionally mono-, di- or tri-substituted with Y$_1$, Y$_2$, and/or Y$_3$, respectively,
(9) aralkyl of about 7 to about 15 carbon atoms which is optionally mono-, di-, or tri-substituted in the aryl ring with Y$_1$, Y$_2$, and/or Y$_3$, respectively,
(10) heteroaralkyl of 6 to 11 atoms with the ring atoms selected from carbon and heteroatoms, wherein the heteroatoms are selected from oxygen, nitrogen, and S(O)$_i$, wherein i is 0, 1 or 2, optionally mono-, di- or tri-substituted with Y$_1$, Y$_2$, and/or Y$_3$, respectively,
(11) aralkenyl of about 8 to about 15 carbon atoms which is optionally mono-, di-, or tri-substituted in the aryl ring with Y$_1$, Y$_2$, and/or Y$_3$, respectively,
(12) heteroaralkenyl of 7 to 12 atoms with the ring atoms selected from carbon and heteroatoms, wherein the heteroatoms are selected from oxygen, nitrogen, and S(O)$_i$, wherein i is 0, 1 or 2, optionally mono-, di- or tri-substituted with Y$_1$, Y$_2$, and/or Y$_3$, respectively,

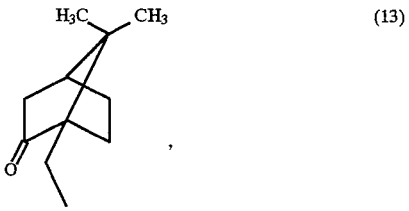
(13)

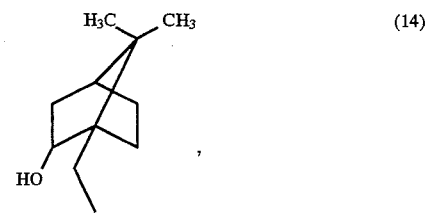
(14)

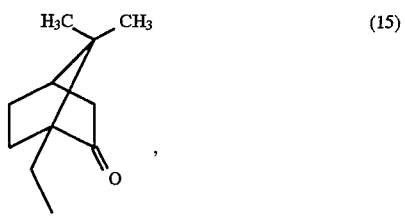
(15)

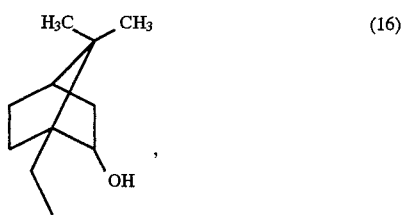
(16)

(17) perfluoroalkyl of 1 to about 12 carbon atoms,
(18) perfluoroaryl of about 6 to about 14 carbon atoms,
(19) perfluoroaralkyl of about 7 to about 15 carbon atoms,
(20) hydrogen, and (21)

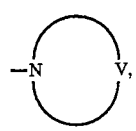

wherein

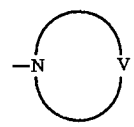

is a 5 to 7 member heterocycle of 3 to 6 ring carbon atoms, where V is —$CH_2$—, —O—, —S(=O)—, —S(O)$_2$— or —S—, wherein $Y_1$, $Y_2$, and $Y_3$ are (i) independently selected from the group consisting of hydrogen, halogen, cyano, tetrazolyl, amino, guanidino, amidino, methylamino, and methylguanidino, —$CF_3$, —$CF_2H$, —$CF_2CF_3$, —$CH(CF_3)_2$, —$C(OH)(CF_3)_2$, $OCF_3$, $OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)NH_2$, —$C(O)NHZ_1$, —$C(O)OZ_1$, —$P(O)_3H$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, and —$NZ_1Z_2$, wherein m is 0, 1 or 2, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or (ii) $Y_1$ and $Y_2$ are selected together to be —$OC(Z_3)(Z_4)O$, wherein $Z_3$ and $Z_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, (c) $R_2$ is selected from the group consisting of hydrogen, alkyl of 1 to about 4 carbon atoms, and alkenyl of about 2 to about 4 carbon atoms, (d) $R_3$ is

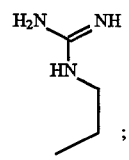

(e) Het is selected from the group consisting of

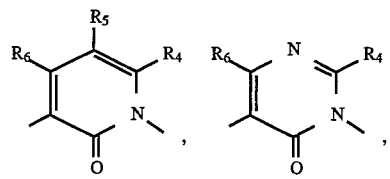

and

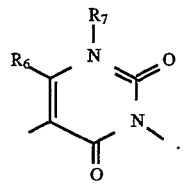

wherein
(1) $R_4$ is selected from the group consisting of $R_1$, —$OR_1$, —$NHR_1$, —$S(O)_nR_1$, and halogen, wherein n is 0, 1 or 2, and $R_1$ is independently selected,
(2) $R_5$ is selected from the group consisting of $R_1$, —$OR_1$, —$NHR_1$, —$S(O)_nR_1$, and halogen, wherein n is 0, 1 or 2, and $R_1$ is independently selected,
(3) $R_6$ is selected from the group consisting of $R_1$, —$OR_1$, —$NHR_1$, —$S(O)_nR_1$, or halogen, wherein n is 0, 1 or 2, and $R_1$ is independently selected, and
(4) $R_7$ is independently selected from the $R_1$ group of substituents, as defined above.

2. A compound according to claim 1, wherein X is selected from the group consisting of —$SO_2$—, —NH—S$(O)_2$—, and —N(R')—$S(O)_2$.

3. A compound according to claim 2, wherein X is —$SO_2$—.

4. A compound according to claim 1, wherein $R_1$ is selected from the group consisting of alkyl, aralkyl, and aryl.

5. A compound according to claim 4, wherein $R_1$ is selected from the group consisting of substituted or unsubstituted phenyl, benzyl, and naphthyl.

6. A compound according to claim 5, wherein $R_1$ is substituted with a substituent selected from the group consisting of methyl, methoxy, fluoro, chloro, trifluoromethyl, and —$OCF_3$.

7. A compound according to claim 4, wherein $R_1$ is cyclohexyl or cyclohexylmethyl.

8. A compound according to claim 1, wherein $R_2$ is hydrogen.

9. A compound according to claim 1, wherein $R_4$ is selected from the group consisting of:
(a) hydrogen,
(b) alkyl of 1 to 6 carbon atoms substituted with $Z_5$, wherein $Z_5$ is selected from the group consisting of hydrogen, —$CH_3$, halogen, —$C(O)OH$, —$C(O)OR_8$, —$S(O)_2OH$ and —$S(O)_pR_8$ wherein $R_8$ is alkyl of 1 to about 4 carbon atoms, and p is 0, 1 or 2,
(c) alkyl of 1 to 3 carbon atoms substituted with cyclic alkyl of 3–5 carbon atoms,
(d) alkenyl of about 3 to about 6 carbon atoms,
(e) alkyl substituted with $Z_6$, wherein $Z_6$ is selected from the group consisting of hydrogen, halogen, —$C(O)OH$, —$C(O)OR_9$, —$S(O)_2OH$ and —$S(O)_pR_9$ wherein $R_9$ is alkyl of 1 to about 6 carbon atoms, and n is 0, 1 or 2,
(f) cycloalkyl of about 3 to about 5 carbon atoms,
(g) heteroaryl having 1 to about 4 ring carbon atoms with the ring atoms selected from carbon and heteroatoms, wherein the heteroatoms are selected from oxygen, sulfur and nitrogen, and (h) heteroaralkyl of 2 to about 6 carbon atoms with the ring atoms selected from carbon and heteroatoms, wherein the heteroatoms are selected from oxygen, sulfur and nitrogen.

10. A compound according to claim 1, wherein $R_5$ is selected from the group consisting of hydrogen, alkyl of 1 to about 5 carbon atoms, trifluoromethyl, and —$OR_{10}$, wherein $R_{10}$ is an alkyl of 1–4 carbon atoms.

11. A compound according to claim 10, wherein $R_5$ is hydrogen.

12. A compound according to claim 1, wherein $R_6$ is selected from the group consisting of:

(a) hydrogen, (b) alkyl of 1 to about 12 carbon atoms substituted with $Z_7$, wherein $Z_7$ is selected from the group consisting of hydrogen, hydroxy, halogen, —$OR_{11}$, —$NHR_{11}$, —C(O)OH, —C(O)$OR_{11}$, —S(O)$_2$OH and —S(O)$_p$ $R_{11}$, wherein $R_{11}$ is alkyl of 1 to about 12 carbon atoms, aryl of about 6 to about 10 carbon atoms, aralkyl of about 7 to about 12 carbon atoms, heteroaryl of 1 to about 9 carbon atoms with the ring atoms selected from carbon and heteroatoms, wherein the heteroatoms are selected from oxygen, sulfur and nitrogen, optionally mono-, di- or tri-substituted with $Y_1$, $Y_2$ and/or $Y_3$, and heteroaralkyl of about 2 to about 10 carbon atoms with the ring atoms selected from carbon and heteroatoms, wherein the heteroatoms are selected from oxygen, sulfur and nitrogen, optionally mono-, di- or tri-substituted with $Y_1$, $Y_2$ and/or $Y_3$, and p is 0, 1 or 2, (c) alkyl of 1 to about 3 carbon atoms substituted with cyclic alkyl of about 5 to about 8 carbon atoms, (d) alkenyl of about 2 to about 6 carbon atoms which is optionally substituted with cyclic alkyl of about 3 to about 8 carbon atoms, aryl of about 6 to about 10 carbon atoms or heteroaryl of 1 to about 9 carbon atoms, (e) aralkyl of about 7 to about 15 carbon atoms which is optionally substituted on the alkyl chain with hydroxy or halogen, and optionally mono-, di- or tri-substituted on the ring with $Y_1$, $Y_2$ and/or $Y_3$, as defined above, (f) heteroaralkyl ring of about 5 to about 10 ring atoms with the ring atoms selected from carbon and heteroatoms, wherein the heteroatoms are selected from oxygen, sulfur and nitrogen, optionally substituted on the alkyl chain with hydroxy or halogen, and optionally mono-, di- or tri-substituted on the ring with $Y_1$, $Y_2$ and/or $Y_3$, (g) aralkenyl of about 6 to 15 carbon atoms which is optionally mono-, di- or tri-substituted on the ring with $Y_1$, $Y_2$ and/or $Y_3$, and (h) heteroaralkenyl ring of about 5 to about 10 ring atoms with the ring atoms selected from carbon and heteroatoms, wherein the heteroatoms are selected from oxygen, sulfur and nitrogen, optionally mono-, di- or tri-substituted with $Y_1$, $Y_2$ and/or $Y_3$.

13. A compound according to claim 12, wherein $R_4$ and $R_5$ are hydrogen or methyl and $R_6$ is selected from the group consisting of aralkyl of about 8 to about 13 carbon atoms, —O-aralkyl, —NH-aralkyl, and —S(O)$_p$-aralkyl of about 7 to about 12 carbon atoms.

14. A compound according to claim 13, wherein the aralkyl of the $R_6$ is selected from unsubstituted or substituted phenyl or naphthyl substituted with 1 to 3 independently selected substituents.

15. A compound according to claim 14, wherein said substituents are selected from the group consisting of methyl, methoxy, fluoro, chloro and trifluoromethyl.

16. A compound according to claim 12, wherein $R_6$ is selected from the group consisting of phenylethyl, phenylpropyl, cyclohexylethyl and cyclohexylpropyl.

17. A compound according to claim 1, wherein $R_7$ is selected from the group consisting of hydrogen, methyl, difluoromethyl and trifluoromethyl.

18. A compound according to claim 17, wherein $R_7$ is hydrogen.

19. A compound according to claim 1, wherein Het is

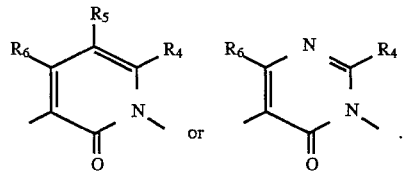

20. A compound according to claim 19, wherein $R_5$ and $R_6$ are independently selected from hydrogen and methyl and Het is

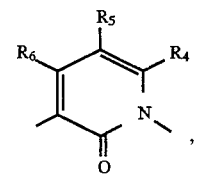

wherein $R_4$ is selected from the group consisting of hydrogen, methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrolyl, 3-pyrolyl, 1-hexyl, S-2-hexyl, R-2-hexyl, R-3-hexyl, and S-3-hexyl.

21. A compound according to claim 20, wherein $R_4$ is hydrogen or methyl.

22. A compound according to claim 1, wherein X is —S(O)$_2$—, $R_1$ is substituted or unsubstituted aralkyl or substituted or unsubstituted phenyl, and Het is

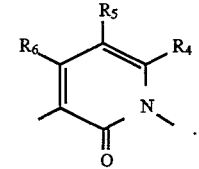

23. A compound according to claim 22, wherein $R_1$ is substituted or unsubstituted benzyl or phenyl.

24. A compound according to claim 1 wherein X is —S(O)$_2$—.

25. A compound according to claim 24 wherein $R_1$ is alkyl, aryl or aralkyl.

26. A compound according to claim 25 wherein $R_1$ is aryl or aralkyl and $Y_1$ and $Y_2$ are independently selected from —C(O)OH, —C(O)$OZ_1$, —OH, —S(O)$_m$Z, and —CF$_3$.

27. A compound according to claim 26 wherein $R_1$ is unsubstituted naphthyl, substituted naphthyl, unsubstituted phenyl, substituted phenyl, unsubstituted benzyl or substituted benzyl.

28. A compound according to claim 27 wherein $R_1$ is benzyl.

29. A compound according to claim 25 wherein $R_1$ is cyclohexyl or cyclohexylmethyl.

30. A compound according to claim 27 wherein Het is

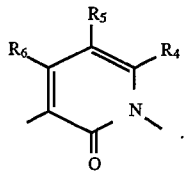

31. A compound selected from the group consisting of:
3-[(phenylsulfonyl)amino-2-oxo-1,2-dihydropyridylacetyl-L-argininal,
3-[(2-naphthylsulfonyl)amino]-2-oxo-1,2 dihydropyridylacetyl-L-argininal,
3-[(1-naphthylsulfonyl)amino]-2-oxo-1,2-dihydropyridylacetyl-L-argininal,
3-(cyclohexylaminosulfonylamino-2-oxo-1,2-dihydropyridyl)-acetyl-L-argininal,
3-(phenylaminosulfonylamino-2-oxo-1,2-dihydropyridylacetyl-L-argininal,
3-[(phenoxycarbonyl)amino]-2-oxo-1,2-dihydropyridylacetyl-L-argininal,
3-[(cyclohexylsulfonyl)amino]-2-oxo-1,2-dihydropyridylacetyl-L-argininal,
3-[(cyclohexylmethylsulfonyl)amino]-2-oxo-1,2 dihydropyridylacetyl-L-argininal,
3-[(phenethylsulfonyl)amino]-2-oxo-1,2-dihydropyridylacetyl-L-argininal,
3-[(2-methoxycarbonylphenylsulfonyl)amino]-2-oxo-1,2-dihydropyridylacetyl-L-argininal,
3-[(3-methoxycarbonylphenylsulfonyl)amino]-2-oxo-1,2-dihydropyridylacetyl-L-argininal,
3-[(4-methoxycarbonylphenylsulfonyl)amino]-2-oxo-1,2-dihydropyridylacetyl-L-argininal,
3-[(2-trifluoromethylphenylsulfonyl)amino]-2-oxo-1,2-dihydropyridylacetyl-L-argininal,
3-[(3-trifluoromethylphenylsulfonyl)amino]-2-oxo-1,2-dihydropyridylacetyl-L-argininal,
3-[(4-trifluoromethylphenylsulfonyl)amino]-2-oxo-1,2-dihydropyridylacetyl-L-argininal,
3-[(2-methoxycarbonylbenzylsulfonyl)amino]-2-oxo-1,2-dihydropyridylacetyl-L-argininal,
3-[(3-methoxycarbonylbenzylsulfonyl)amino]-2-oxo-1,2-dihydropyridylacetyl-L-argininal,
3-[(4-methoxycarbonylbenzylsulfonyl)amino]-2-oxo-1,2-dihydropyridylacetyl-L-argininal,
3-[(2-trifluoromethylbenzylsulfonyl)amino]-2-oxo-1,2-dihydropyridylacetyl-L-argininal,
3-[(3-trifluoromethylbenzylsulfonyl)amino]-2-oxo-1,2-dihydropyridylacetyl-L-argininal,
3-[(4-trifluoromethylbenzylsulfonyl)amino]-2-oxo-1,2-dihydropyridylacetyl-L-argininal,
[3-[(benzylsulfonyl)amino]-2-oxo-1,2-dihydropyridyl]acetyl-L-argininal,
[3-[(benzylsulfonyl)amino]-6-methyl-2-oxo-1,2-dihydropyridyl]acetyl-L-argininal,
5-benzylsulfonylamino-6-oxo-1,6-dihydro-1-pyrimidinylacetyl-L-argininal,
2-methyl-5-benzylsulfonylamino-6-oxo-1,6-dihydro-1-pyrimidinylacetyl-L-argininal,
5-benzylsulfonylamino-uracilylacetyl-L-argininal,
5-benzylsulfonylamino-1-methyl-uracilylacetyl-L-argininal and,
3-[(2-trifluoromethylbenzylsulfonyl)amino]-2-oxo-1,2-dihydropyridyl acetyl-L-argininal.

* * * * *

UNITED STATES PATENT AND TRADEMARK OFFICE
CERTIFICATE OF CORRECTION

PATENT NO. : 5,656,645
DATED : August 12, 1997
INVENTOR(S) :
Tamura et al.

It is certified that error appears in the above-identified patent and that said Letters Patent is hereby corrected as shown below:

Column 104, line 34: please add the following claims:

--32. A compound according to claim 31:

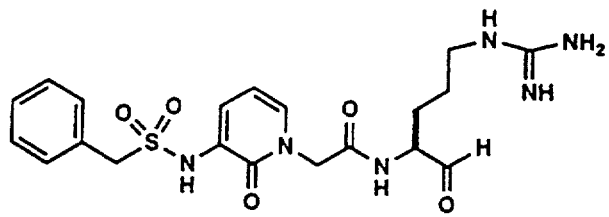

[3-[(benzylsulfonyl)amino]-2-oxo-1,2-dihydropyridyl]acetyl-L-argininal and pharmaceutically acceptable salts thereof.

33. The compound according to claims 31:

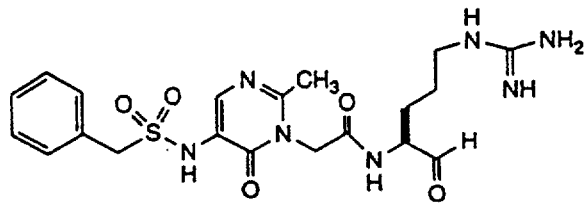

2-methyl-5-benzylsulfonylamino-6-oxo-1,6-dihydro-1-pyrimidinylacetyl-L-argininal and pharmaceutically acceptable salts thereof.

UNITED STATES PATENT AND TRADEMARK OFFICE
CERTIFICATE OF CORRECTION

PATENT NO. : 5,656,645  
DATED : August 12, 1997  
INVENTOR(S) : Tamura et al.

Page 2 of 4

It is certified that error appears in the above-identified patent and that said Letters Patent is hereby corrected as shown below:

34. A compound according to claim 31:

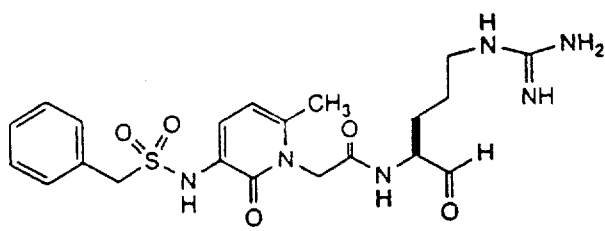

(3-benzylsulfonylamino-6-methyl-2-oxo-1,2-dihydro-1-pyridyl)acetyl-L-argininal and pharmaceutically acceptable salts thereof.

35. The compound according to claim 1:

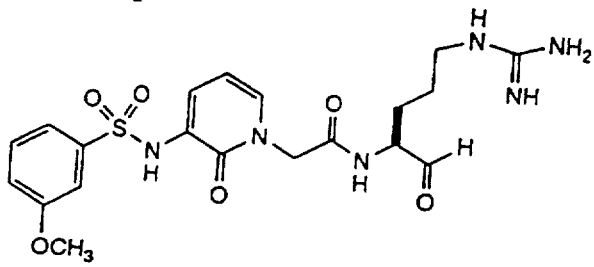

[3-(3-methoxyphenyl)sulfonylamino-2-oxo-1,2-dihydropyridyl]acetyl-L-argininal and pharmaceutically acceptable salts thereof.

UNITED STATES PATENT AND TRADEMARK OFFICE
CERTIFICATE OF CORRECTION

PATENT NO. : 5,656,645
DATED : August 12, 1997
INVENTOR(S) : Tamura et al.

It is certified that error appears in the above-identified patent and that said Letters Patent is hereby corrected as shown below:

36. A compound according to claim 1:

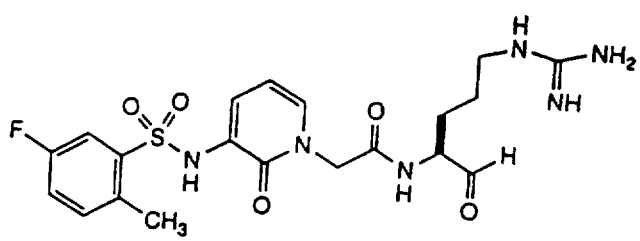

[3-(2-methyl-5-fluorophenyl)sulfonylamino-2-oxo-1,2-dihydro-pyridyl]acetyl-L-argininal and pharmaceutically acceptable salts thereof.

37. A compound according to claim 32 which is a trifluoroacetic acid salt.

38. A compound according to claim 33 which is a trifluoroacetic acid salt.

UNITED STATES PATENT AND TRADEMARK OFFICE
CERTIFICATE OF CORRECTION

PATENT NO. : 5,656,645
DATED : August 12, 1997
INVENTOR(S) : Tamura et al.

It is certified that error appears in the above-identified patent and that said Letters Patent is hereby corrected as shown below:

39. A compound according to claim 34 which is a trifluoroacetic acid salt.

40. A compound according to claim 35 which is a trifluoroacetic acid salt.

41. A compound according to claim 36 which is a trifluoroacetic acid salt.--

Signed and Sealed this

Twenty-fifth Day of August, 1998

Attest:

BRUCE LEHMAN

Attesting Officer

Commissioner of Patents and Trademarks